(12) United States Patent
Moriya et al.

(10) Patent No.: US 8,729,271 B2
(45) Date of Patent: May 20, 2014

(54) GLYCINE TRANSPORTER INHIBITING SUBSTANCES

(75) Inventors: Minoru Moriya, Toshima-ku (JP); Akito Yasuhara, Toshima-ku (JP); Kazunari Sakagami, Toshima-ku (JP); Hiroshi Ohta, Toshima-ku (JP); Kumi Abe, Toshima-ku (JP); Shuji Yamamoto, Toshima-ku (JP); Yuko Araki, Toshima-ku (JP); Hiroki Urabe, Toshima-ku (JP); Xiang-Min Sun, Toshima-ku (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 0 days.

(21) Appl. No.: 13/823,574

(22) PCT Filed: Sep. 16, 2011

(86) PCT No.: PCT/JP2011/071241
§ 371 (c)(1),
(2), (4) Date: Mar. 14, 2013

(87) PCT Pub. No.: WO2012/036278
PCT Pub. Date: Mar. 22, 2012

(65) Prior Publication Data
US 2013/0184460 A1   Jul. 18, 2013

(30) Foreign Application Priority Data
Sep. 17, 2010   (JP) .................................. 2010-209184

(51) Int. Cl.
| | | |
|---|---|---|
| *A01N 43/40* | (2006.01) | |
| *A61K 31/44* | (2006.01) | |
| *A01N 43/64* | (2006.01) | |
| *A61K 31/41* | (2006.01) | |
| *C07D 213/00* | (2006.01) | |
| *C07D 401/00* | (2006.01) | |
| *C07D 419/00* | (2006.01) | |

(52) U.S. Cl.
USPC .................. 546/268.4; 546/266.8; 546/272.4; 546/272.7; 546/274.7; 514/383; 514/336; 514/340; 514/341; 514/385

(58) Field of Classification Search
USPC ........................................ 514/383; 548/266.8
See application file for complete search history.

(56) References Cited

U.S. PATENT DOCUMENTS

| 8,623,898 B2 * | 1/2014 | Yasuhara et al. .............. 514/383 |
| 2012/0010414 A1 | 1/2012 | Yasuhara et al. |
| 2012/0116095 A1 * | 5/2012 | Yasuhara et al. ........... 548/266.8 |

FOREIGN PATENT DOCUMENTS

| WO | 2005037216 | 4/2005 |
| WO | 2006051063 | 5/2006 |
| WO | 2006106425 | 10/2006 |
| WO | 2007087906 | 8/2007 |
| WO | 2008065500 | 6/2008 |
| WO | 2010107115 | 9/2010 |
| WO | 2011007899 | 1/2011 |

OTHER PUBLICATIONS

Lars et al., Current Opinion in Pharmacology, (2007), vol. 7, pp. 48-55.*
Javitt, "Glutamate as a therapeutic target in psychiatric disorders", Molecular Psychiatry, 9:984-997 (2004).
Harsing Jr. et al., "Glycine transporter Type-1 and its Inhibitors", Current Medicinal Chemistry, 13:1017-1044 (2006).
Depoortére et al., "Neurochemical, Electrophysiological and Pharmaceutical Profiles of the selective inhibitor of the Glycine Transporter-I SSR504734, a Potential New Type of Antiphychotic", Neuropsychopharmacology, 30:1963-1985 (2005).
Slassi et al, "Recent progress in the use of glycine transporter-1 inhibitors for the treatment of central and peripheral nervous system disease", Expert Opinion on Therapeutic Patents, 14(2):201-214 (2004).
Lowe III et al., "The discovery of a structurally novel class of inhibitors of the type 1 glycine transporter", Bioorganic & Medicinal Chemistry Letters, 19:2974-2976 (2009).
Lowe III et al., "An octahydro-cyclopenta[c]pyrrole series of inhibitors of the type 1 glycine transporter", Bioorganic & Medicinal Chemistry Letters, 20:907-911 (2010).
International Preliminary Report on Patentability for PCT/JP2011/071241 dated Apr. 16, 2013, with Translation of Written Opinion dated Nov. 8, 2011.
Communication for EP 11825276.6 dated Jan. 24, 2014, with Supplementary European Search Report dated Jan. 16, 2014.

* cited by examiner

*Primary Examiner* — John Mabry
*Assistant Examiner* — Daniel Carcanague
(74) *Attorney, Agent, or Firm* — Sughrue Mion, PLLC

(57) ABSTRACT

The present invention aims to provide novel compounds of formula [I] or pharmaceutically acceptable salts thereof that are based on a glycine uptake inhibiting action and which are useful in the prevention or treatment of such diseases as schizophrenia, Alzheimer's disease, cognitive dysfunction, dementia, anxiety disorders (generalized anxiety disorder, panic disorder, obsessive-compulsive disorder, social anxiety disorder, posttraumatic stress disorder, specific phobia, acute stress disorder, etc.), depression, drug addiction, spasm, tremor, pain, and sleep disorder:

[Chem 1]

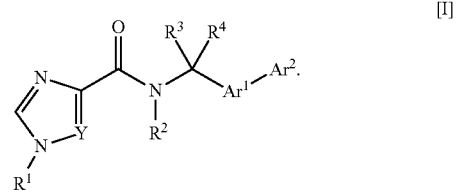

17 Claims, No Drawings

GLYCINE TRANSPORTER INHIBITING SUBSTANCES

CROSS REFERENCE TO RELATED APPLICATIONS

This application is a National Stage of International Application No. PCT/JP2011/071241, filed on Sep. 16, 2011, which claims priority from Japanese Patent Application No. 2010-209184, filed on Sep. 17, 2010, the contents of all of which are incorporated herein by reference in their entirety.

TECHNICAL FIELD

The present invention relates to compounds having a glycine transporter inhibiting action.

BACKGROUND ART

The NMDA receptor which is one of glutamate receptors is found on the nerve cell membranes in the brain and involved in various neurophysiologic events including the plasticity of nerves, as well as cognition, attention, and memory. The NMDA receptor has a plurality of allosteric binding sites, among which is the glycine binding site (NMDA receptor complex glycine binding site). It has been reported that the NMDA receptor complex glycine binding site takes part in the activation of the NMDA receptor (Non-Patent Document 1).

An action potential arriving at the presynaptic terminal of a glycinergic nerve triggers the release of glycine into the synaptic cleft. The released glycine binds to the postsynaptic receptor or the like and is thereafter carried away by the transporter to leave the synaptic cleft. Hence, it is postulated that the glycine transporter regulates the function of the NMDA receptor through regulation of the glycine level in the extracellular fluid.

The glycine transporter (GlyT) is a protein involved in the reuptake of extracellular glycine into the cell and two subtypes, GlyT1 and GlyT2, have so far been identified. GlyT1, which mainly develops in the cerebral cortex, hippocampus, thalamus, etc., has been reported to be associated with such diseases as schizophrenia, Alzheimer's disease, cognitive dysfunction, dementia, anxiety disorders (generalized anxiety disorder, panic disorder, obsessive-compulsive disorder, social anxiety disorder, posttraumatic stress disorder, specific phobia, acute stress disorder, etc.), depression, drug addiction, spasm, tremor, pain and sleep disorder (Non-Patent Documents 2-4).

Compounds featuring the GlyT1 inhibiting action and having a 5-membeed cyclic heteroarylamide structure have been reported in the following documents (Patent Documents 1-3 and Non-Patent Documents 5 and 6).

CITATION LIST

Patent Documents

Patent Document 1: WO2005/037216
Patent Document 2: WO2006/106425
Patent Document 3: WO2008/065500

Non-Patent Documents

Non-Patent Document 1: Molecular Psychiatry (2004) 9, 984-997

Non-Patent Document 2: Current Medicinal Chemistry, 2006, 13, 1017-1044

Non-Patent Document 3: Neuropsychopharmacology (2005), 30, 1963-1985

Non-Patent Document 4: Expert Opinion on Therapeutic Patents (2004) 14 (2) 201-214

Non-Patent Document 5: Bioorganic & Medicinal Chemistry Letters (2009) 19 2974-2976

Non-Patent Document 6: Bioorganic & Medicinal Chemistry Letters (2010) 20 907-911

SUMMARY OF INVENTION

Technical Problems

The present invention aims to provide novel compounds or pharmaceutically acceptable salts thereof that are based on a glycine uptake inhibiting action and which are useful in the prevention or treatment of such diseases as schizophrenia, Alzheimer's disease, cognitive dysfunction, dementia, anxiety disorders (generalized anxiety disorder, panic disorder, obsessive-compulsive disorder, social anxiety disorder, posttraumatic stress disorder, specific phobia, acute stress disorder, etc.), depression, drug addiction, spasm, tremor, pain, and sleep disorder.

Solution to Problems

The present inventors made intensive studies on compounds with a novel skeleton featuring an inhibitory action against GlyT1; as a result, they found that compounds represented by the following formula are superior GlyT1 inhibiting substances and this finding has eventually led to the accomplishment of the present invention.

Hereinbelow, the present invention will be described in detail. Embodiments of the present invention (hereinafter referred to as "the inventive compounds") are as set forth below.

(1) A compound of the formula [I] or a pharmaceutically acceptable salt thereof:

[Chem 1]

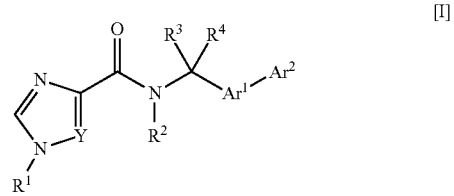

wherein $R^1$ represents a hydrogen atom or a $C_{1-6}$ alkyl group, $R^2$ represents a $C_{1-6}$ alkyl group optionally substituted by 1 to 3 substituents selected from among Group 1 of substituents, or represents a $C_{3-6}$ cycloalkyl group, a haloC$_{3-6}$ cycloalkyl group, or a group of the formula [II]

[Chem 2]

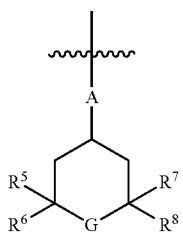

[II]

Group 1 of substituents is a group consisting of a $C_{1-6}$ alkoxyl group, a halogen atom, a $C_{3-6}$ cycloalkyl group, and a halo$C_{1-6}$ alkoxy group, A represents a single bond or a $C_{1-3}$ alkylene group, $R^5$, $R^6$, $R^7$ and $R^8$ are the same or different, and each represent a hydrogen atom or a $C_{1-6}$ alkyl group, G represents an oxygen atom, a sulfur atom, or the formula $SO_2$, $R^3$ and $R^4$ are the same or different, and each represent a hydrogen atom or a $C_{1-6}$ alkyl group, Y represents a nitrogen atom or the formula CH, $Ar^1$ represents a phenylene group or a divalent monocyclic heteroaryl group, provided that the phenylene group or the divalent monocyclic heteroaryl group may be substituted by 1 to 3 substituents selected from Group 2 of substituents, Group 2 of substituents is a group consisting of a $C_{1-6}$ alkoxyl group, a halogen atom, a $C_{1-6}$ alkyl group, a halo$C_{1-6}$ alkoxy group, and a halo$C_{1-6}$ alkyl group, $Ar^2$ represents a phenyl group, a naphthyl group, a monocyclic or bicyclic heteroaryl group, a pyridonyl group, or a group of the formula [III]

[Chem 3]

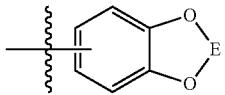

[III]

E represents a $C_{1-3}$ alkylene group, provided that the phenyl group, the naphthyl group, the monocyclic or bicyclic heteroaryl group, the pyridonyl group, or the group of the formula [III] may be substituted by 1 to 5 substituents selected from Group 3 of substituents, Group 3 of substituents is a group consisting of a $C_{1-6}$ alkyl group (which $C_{1-6}$ alkyl group may be substituted by 1 to 3 substituents selected from among a $C_{1-6}$ alkoxy group, a halogen atom, and a hydroxy group), a $C_{1-6}$ alkoxy group, a halogen atom, a halo$C_{1-6}$ alkoxy group, a $C_{1-6}$ alkylthio group, a halo$C_{1-6}$ alkylthio group, a cyano group, a carbamoyl group, the formula —$SF_5$, and the formula —$NR^9R^{10}$ (where $R^9$ and $R^{10}$ are the same or different, and each represent a hydrogen atom or a $C_{1-6}$ alkyl group or, taken together with the nitrogen atom to which they bind, represent a 4- to 6-membered cyclic structure), when $Ar^1$ is the phenylene group which may be substituted by 1 to 3 substituents selected from Group 2 of substituents, $Ar^2$ is the monocyclic or bicyclic heteroaryl group which may be substituted by 1 to 5 substituents selected from Group 3 of substituents (which monocyclic or bicyclic heteroaryl group includes a pyridyl group, a pyrazolyl group or an imidazolyl group substituted by 1 to 5 substituents selected from Group 3 of substituents), the pyridonyl group which may be substituted by 1 to 4 substituents selected from Group 3 of substituents, or the group of the formula [III] which may be substituted by 1 to 5 substituents selected from Group 3 of substituents (with the exception of 1-methyl-N-[3-(pyridin-2-yl)benzyl]-N-(tetrahydro-2H-pyran-4-yl)-1H-1,2,4-triazole-3-carboxamide, 1-methyl-N-[3-(pyridin-3-yl)benzyl]-N-(tetrahydro-2H-pyran-4-yl)-1H-1,2,4-triazole-3-carboxamide, 1-methyl-N-[3-(pyridin-4-yl)benzyl]-N-(tetrahydro-2H-pyran-4-yl)-1H-1,2,4-triazole-3-carboxamide, N-[3-(1H-imidazol-1-yl)benzyl]-1-methyl-N-(tetrahydro-2H-pyran-4-yl)-1H-1,2,4-triazole-3-carboxamide, and 1-methyl-N-[3-(1H-pyrazol-4-yl)benzyl]-N-(tetrahydro-2H-pyran-4-yl)-1H-1,2,4-triazole-3-carboxamide).

(2) The compound or the pharmaceutically acceptable salt thereof according to (1), wherein $R^2$ is a $C_{1-6}$ alkyl group optionally substituted by 1 to 3 substituents selected from Group 1 of substituents, or represents a $C_{3-6}$ cycloalkyl group, a halo$C_{3-6}$ cycloalkyl group, or the group of the formula [II]

A is a single bond or a $C_{1-3}$ alkylene group, $R^5$, $R^6$, $R^7$ and $R^8$ are each a hydrogen atom, G is an oxygen atom, $Ar^1$ is a phenylene group, a pyridine-diyl group, a pyrimidine-diyl group, an isoxazole-diyl group, an oxadiazole-diyl group, a thiazole-diyl group, or a pyrazole-diyl group, provided that the phenylene group, the pyridine-diyl group, the pyrimidine-diyl group, the isoxazole-diyl group, the oxadiazole-diyl group, the thiazole-diyl group, or the pyrazole-diyl group may be substituted by 1 to 3 halogen atoms, and $Ar^2$ is a phenyl group, a naphthyl group, a pyridyl group, a pyrimidyl group, a pyrazyl group, a pyrazolyl group, a thiazolyl group, an imidazolyl group, an isoxazolyl group, a thienyl group, a triazolyl group, an indolyl group, a benzofuryl group, a quinolyl group, an isoquinolyl group, a pyridonyl group, an imidazopyridyl group, or the group of the formula [III], provided that the phenyl group, the naphthyl group, the pyridyl group, the pyrimidyl group, the pyrazyl group, the pyrazolyl group, the thiazolyl group, the imidazolyl group, the isoxazolyl group, the thienyl group, the triazolyl group, the indolyl group, the benzofuryl group, the quinolyl group, the isoquinolyl group, the pyridonyl group, the imidazopyridyl group, or the group of the formula [III] may be substituted by 1 to 5 substituents selected from Group 3 of substituents.

(3) The compound or the pharmaceutically acceptable salt thereof according to (1) or (2), wherein $R^2$ is a) a $C_{1-6}$ alkyl group optionally substituted by 1 to 3 substituents selected from among a $C_{1-6}$ alkoxyl group, a halogen atom, and a $C_{3-6}$ cycloalkyl group, or b) a $C_{3-6}$ cycloalkyl group.

(4) The compound or the pharmaceutically acceptable salt thereof according to (1) or (2), wherein $R^2$ is a $C_{3-6}$ branched chain alkyl group, or a $C_{4-6}$ cycloalkyl group.

(5) The compound or the pharmaceutically acceptable salt thereof according to any one of (1) to (4), wherein Y is the formula CH.

(6) The compound or the pharmaceutically acceptable salt thereof according to (1), wherein $Ar^1$ is a phenylene group optionally substituted by 1 to 3 substituents selected from Group 2 of substituents.

(7) The compound or the pharmaceutically acceptable salt thereof according to any one of (1) to (5), wherein $Ar^1$ is a 1,3-phenylene group which may be substituted by a halogen atom, a pyridine-2,4-diyl group (with the carbon atom adjacent to the nitrogen atom binding to Ar²), a pyrimidine-2,4-diyl group, an isoxazole-3,5-diyl group, an oxadiazole-3,5-diyl group, a thiazole-2,4-diyl group, or a pyrazole-1,4-diyl group.

(8) The compound or the pharmaceutically acceptable salt thereof according to any one of (1) to (5), wherein Ar¹ is a 1,3-phenylene group which has been substituted by a halogen atom, or a pyridine-2,4-diyl group (with the carbon atom adjacent to the nitrogen atom binding to Ar²).

(9) The compound or the pharmaceutically acceptable salt thereof according to any one of (1) to (8), wherein Ar² is a phenyl group, a naphthyl group, a pyridyl group, a pyrimidyl group, a pyrazyl group, a pyrazolyl group, an imidazolyl group, a thienyl group, an imidazo[1,2-a]pyridyl group, or a quinolyl group, provided that the phenyl group, the naphthyl group, the pyridyl group, the pyrimidyl group, the pyrazyl group, the pyrazolyl group, the imidazolyl group, the thienyl group, the imidazo[1,2-a]pyridyl group, or the quinolyl group may be substituted by 1 to 5 substituents selected from Group 3 of substituents.

(10) The compound or the pharmaceutically acceptable salt thereof according to any one of (1) to (5) and (7) to (8), wherein Ar² is a phenyl group which may be substituted by 1 to 5 substituents selected from Group 3 of substituents.

(11) The compound or the pharmaceutically acceptable salt thereof according to any one of (1) to (8), wherein Ar² is a phenyl group optionally substituted by 1 to 5 substituents selected from Group 4 of substituents, a pyridyl group optionally substituted by 1 to 4 substituents selected from Group 5 of substituents, a pyrimidyl group optionally substituted by 1 to 3 substituents selected from Group 5 of substituents, or a pyrazyl group optionally substituted by 1 to 3 substituents selected from Group 5 of substituents, Group 4 of substituents is a group consisting of a $C_{1-6}$ alkyl group optionally substituted by 1 to 3 halogen atoms, a halogen atom, and a haloC$_{1-6}$ alkoxy group, and Group 5 of substituents is a group consisting of a $C_{1-6}$ alkyl group optionally substituted by 1 to 3 halogen atoms, a $C_{1-6}$ alkoxy group, a halogen atom, a haloC$_{1-6}$ alkoxy group, a cyano group, and the formula —NR⁹R¹⁰.

(12) The compound or the pharmaceutically acceptable salt thereof according to any one of (1) to (8), wherein Ar² is a phenyl group optionally substituted by 1 to 5 substituents selected from the group 4 of substituents, or a pyridyl group optionally substituted by 1 to 4 substituents selected from Group 5 of substituents.

(13) The compound or the pharmaceutically acceptable salt thereof according to any one of (1) to (5) and (7) to (8), wherein Ar² is a phenyl group substituted by 1 to 5 haloC$_{1-6}$ alkoxy groups.

(14) The compound or the pharmaceutically acceptable salt thereof according to any one of (1) to (13), wherein R¹ is a $C_{1-6}$ alkyl group, and
R³ and R⁴ are each a hydrogen atom.

(15) The compound or the pharmaceutically acceptable salt thereof according to (1), which is selected from the following group of compounds:

N-[4-fluoro-3-(6-fluoropyridin-3-yl)benzyl]-1-methyl-N-(propan-2-yl)-1H-imidazole-4-carboxamide
N-[4-fluoro-3-(pyridin-2-yl)benzyl]-1-methyl-N-(propan-2-yl)-1H-imidazole-4-carboxamide
1-Methyl-N-(propan-2-yl)-N-({2-[4-trifluoromethoxy)phenyl]pyridin-4-yl}methyl)-1H-imidazole-4-carboxamide
N-{[2-(4-fluorophenyl)pyridin-4-yl]methyl}-1-methyl-N-(propan-2-yl)-1H-imidazole-4-carboxamide
1-Methyl-N-(propan-2-yl)-N-({2-[4-(trifluoromethyl)phenyl]pyridin-4-yl}methyl)-1H-imidazole-4-carboxamide
1-Methyl-N-[(2-phenylpyridin-4-yl)methyl]-N-(propan-2-yl)-1H-imidazole-4-carboxamide
N-{[2-(3-fluorophenyl)pyridin-4-yl]methyl}-1-methyl-N-(propan-2-yl)-1H-imidazole-4-carboxamide
N-cyclobutyl-N-{[2-(4-fluorophenyl)pyridin-4-yl]methyl}-1-methyl-1H-imidazole-4-carboxamide
N-{[2-(3,4-difluorophenyl)pyridin-4-yl]methyl}-1-methyl-N-(propan-2-yl)-1H-imidazole-4-carboxamide
N-{[2-(3,5-difluorophenyl)pyridin-4-yl]methyl}-1-methyl-N-(propan-2-yl)-1H-imidazole-4-carboxamide
1-Methyl-N-(propan-2-yl)-N-({2-[3-(trifluoromethoxy)phenyl]pyridin-4-yl}methyl)-1H-imidazole-4-carboxamide
N-{[2-(2,4-difluorophenyl)pyridin-4-yl]methyl}-1-methyl-N-(propan-2-yl)-1H-imidazole-4-carboxamide
1-Methyl-N-(propan-2-yl)-N-{[2-(3,4,5-trifluorophenyl)pyridin-4-yl]methyl}-1H-imidazole-4-carboxamide
1-Methyl-N-(propan-2-yl)-N-{[2-(2,3,4-trifluorophenyl)pyridin-4-yl]methyl}-1H-imidazole-4-carboxamide
N-{[2-(4-chlorophenyl)pyridin-4-yl]methyl}-1-methyl-N-(propan-2-yl)-1H-imidazole-4-carboxamide
N-[4-fluoro-3-(1H-pyrazol-1-yl)benzyl]-1-methyl-N-(propan-2-yl)-1H-imidazole-4-carboxamide
N-{[2-(2-fluorophenyl)pyridin-4-yl]methyl}-1-methyl-N-(propan-2-yl)-1H-imidazole-4-carboxamide
N-{[2-(3-chlorophenyl)pyridin-4-yl]methyl}-1-methyl-N-(propan-2-yl)-1H-imidazole-4-carboxamide
N-{[2-(2,3-difluorophenyl)pyridin-4-yl]methyl}-1-methyl-N-(propan-2-yl)-1H-imidazole-4-carboxamide
N-[4-fluoro-3-(3-fluoropyridin-2-yl)benzyl]-1-methyl-N-(propan-2-yl)-1H-imidazole-4-carboxamide
N-{[2-(3-chloro-4-fluorophenyl)pyridin-4-yl]methyl}-1-methyl-N-(propan-2-yl)-1H-imidazole-4-carboxamide
N-{[2-(3-fluoro-4-methylphenyl)pyridin-4-yl]methyl}-1-methyl-N-(propan-2-yl)-1H-imidazole-4-carboxamide
N-{[2-(4-fluoro-3-methylphenyl)pyridin-4-yl]methyl}-1-methyl-N-(propan-2-yl)-1H-imidazole-4-carboxamide
N-{[2-(3-chloro-5-fluorophenyl)pyridin-4-yl]methyl}-1-methyl-N-(propan-2-yl)-1H-imidazole-4-carboxamide
N-{[2-(2,5-difluorophenyl)pyridin-4-yl]methyl}-1-methyl-N-(propan-2-yl)-1H-imidazole-4-carboxamide
1-Methyl-N-(propan-2-yl)-N-{[2-(2,4,5-trifluorophenyl)pyridin-4-yl]methyl}-1H-imidazole-4-carboxamide
N-cyclobutyl-1-methyl-N-({2-[3-(trifluoromethoxy)phenyl]pyridin-4-yl}methyl)-1H-imidazole-4-carboxamide
N-cyclobutyl-1-methyl-N-({2-[4-(trifluoromethoxy)phenyl]pyridin-4-yl}methyl)-1H-imidazole-4-carboxamide
N-{[2-(3-fluoro-5-methylphenyl)pyridin-4-yl]methyl}-1-methyl-N-(propan-2-yl)-1H-imidazole-4-carboxamide
1-Methyl-N-(propan-2-yl)-N-({2-[3-trifluoromethyl)phenyl]pyridin-4-yl}methyl)-1H-imidazole-4-carboxamide
N-{[2-(3,4-dichlorophenyl)pyridin-4-yl]methyl}-1-methyl-N-(propan-2-yl)-1H-imidazole-4-carboxamide
N-{[2-(3,5-dichlorophenyl)pyridin-4-yl]methyl}-1-methyl-N-(propan-2-yl)-1H-imidazole-4-carboxamide
N-{[2-(2-chlorophenyl)pyridin-4-yl]methyl}-1-methyl-N-(propan-2-yl)-1H-imidazole-4-carboxamide
N-cyclobutyl-N-[4-fluoro-3-(6-fluoropyridin-3-yl)benzyl]-1-methyl-1H-imidazole-4-carboxamide
N-({2-[4-(difluoromethoxy)phenyl]pyridin-4-yl}methyl)-1-methyl-N-(propan-2-yl)-1H-imidazole-4-carboxamide
N-({2-[3-fluoro-4-(trifluoromethoxy)phenyl]pyridin-4-yl}methyl)-1-methyl-N-(propan-2-yl)-1H-imidazole-4-carboxamide
N-({2-[3-(difluoromethoxy)phenyl]pyridin-4-yl}methyl)-1-methyl-N-(propan-2-yl)-1H-imidazole-4-carboxamide N-({2-[4-fluoro-3-(trifluoromethoxy)phenyl]pyridin-4-yl}methyl)-1-methyl-N-(propan-2-yl)-1H-imidazole-4-carboxamide N-cyclobutyl-N-{[2-(3,4-difluorophenyl)pyridin-4-yl]methyl}-1-methyl-1H-imidazole-4-carboxamide N-cyclobutyl-N-{[2-(3,5-difluorophenyl)pyridin-4-yl]methyl}-1-methyl-1H-imidazole-4-carboxamide N-cyclobutyl-N-({2-[4-(difluoromethoxy)phenyl]pyridin-4-yl}methyl)-1-methyl-1H-imidazole-4-carboxamide N-cyclobutyl-N-({2-[3-(difluoromethoxy)phenyl]pyridin-4-yl}methyl)-1-methyl-1H-imidazole-4-carboxamide N-cyclobutyl-1-methyl-N-({2-[4-(trifluoromethoxy)phenyl]pyridin-4-yl}methyl)-1H-1,2,4-triazole-3-carboxamide N-cyclobutyl-1-methyl-N-({2-[3-(trifluoromethoxy)phenyl]pyridin-4-yl}methyl)-1H-1,2,4-triazole-3-carboxamide N-cyclobutyl-1-methyl-N-{[2-(2,4,5-trifluorophenyl)pyridin-4-yl]methyl}-1H-imidazole-4-carboxamide N-cyclobutyl-N-{[2-(2,3-difluorophenyl)pyridin-4-yl]methyl}-1-methyl-1H-imidazole-4-carboxamide N-cyclobutyl-N-{[2-(2,4-difluorophenyl)pyridin-4-yl]methyl}-1-methyl-1H-imidazole-4-carboxamide N-cyclobutyl-N-{[2-(2,5-difluorophenyl)pyridin-4-yl]methyl}-1-methyl-1H-imidazole-4-carboxamide N-cyclobutyl-N-[4-fluoro-3-(3-fluoropyridin-2-yl)benzyl]-1-methyl-1H-imidazole-4-carboxamide N-cyclobutyl-N-({2-[3-(difluoromethoxy)-4-fluorophenyl]pyridin-4-yl}methyl)-1-methyl-1H-imidazole-4-carboxamide N-cyclobutyl-N-({2-[4-(difluoromethoxy)-3-fluorophenyl]pyridin-4-yl}methyl)-1-methyl-1H-imidazole-4-carboxamide

(16) A medicament comprising, as an active ingredient, the compound or the pharmaceutically acceptable salt thereof according to any one of (1) to (15).

(17) An agent for preventing or treating a disease selected from among schizophrenia, Alzheimer's disease, cognitive dysfunction, dementia, anxiety disorders, depression, drug addiction, spasm, tremor, pain, and sleep disorder, which comprises as an active ingredient, the compound or the pharmaceutically acceptable salt thereof according to any one of (1) to (15).

Advantageous Effects of Invention

The inventive compounds have a glycine transporter (GlyT1) inhibiting activity. The inventive compounds also have high membrane permeability as shown in the Test Examples to be described later. Thus, they are expected to be excellent in intestinal absorption which is important for medicaments that are to be administered orally. Furthermore, the inventive compounds are not recognized as a substrate for P-glycoprotein which is a discharge transporter controlling the migration of a drug into the brain, as shown in the Test Examples described later. Hence, they are expected to provide satisfactory migration of the drug into the brain.

DESCRIPTION OF EMBODIMENTS

The term "$C_{x-y}$ (x and y each denote a natural number)" as used herein means that the number of carbon atoms is x to y.

The term "$C_{1-6}$ alkyl group" as used herein refers to a straight-chain or branched-chain alkyl group having 1 to 6 carbon atoms, and includes, for example, a methyl group, an ethyl group, a propyl group, an isopropyl group, a butyl group, an isobutyl group, a tert-butyl group, a pentyl group, an isopentyl group, and a hexyl group.

The term "$C_{1-6}$ alkylthio group" as used herein refers to a straight-chain or branched-chain alkylthio group having 1 to 6 carbon atoms, and the preferred number of substituting halogen atoms is 1 to 3. Examples of the $C_{1-6}$ alkylthio group are a methylthio group, an ethylthio group, a propylthio group, an isopropylthio group, a butylthio group, an isobutylthio group, a tert-butylthio group, a pentylthio group, an isopentylthio group, and a hexylthio group.

The term "$C_{3-6}$ cycloalkyl group" as used herein refers to a cycloalkyl group having 3 to 6 carbon atoms, and includes, for example, a cyclopropyl group, a cyclobutyl group, a cyclopentyl group, and a cyclohexyl group.

The term "$C_{1-6}$ alkoxy group" as used herein refers to a straight-chain or branched-chain alkoxy group having 1 to 6 carbon atoms, and includes, for example, a methoxy group, an ethoxy group, a propoxy group, an isopropoxy group, a butoxy group, an isobutoxy group, a pentyloxy group, an isopentyloxy group, and a hexyloxy group.

The term "halogen atom (halo)" as used herein refers to a fluorine atom, a chlorine atom, a bromine atom, or an iodine atom.

The term "halo$C_{1-6}$ alkyl group" as used herein refers to a straight-chain or branched-chain alkyl group having 1 to 6 carbon atoms which has been substituted by a halogen atom or halogen atoms. The preferred number of the substituting halogen atoms is 1 to 3. Examples of the halo$C_{1-6}$ alkyl group are a fluoromethyl group, a difluoromethyl group, a trifluoromethyl group, and a trichloromethyl group.

The term "halo$C_{1-6}$ alkylthio group" as used herein refers to a straight-chain or branched-chain alkylthio group having 1 to 6 carbon atoms which has been substituted by a halogen atom or halogen atoms. The preferred number of the substituting halogen atoms is 1 to 3. Examples of the halo$C_{1-6}$ alkylthio group are a fluoromethylthio group, a difluoromethylthio group, a trifluoromethylthio group, and a trichloromethylthio group.

The term "halo$C_{1-6}$ alkoxy group" as used herein refers to a straight-chain or branched-chain alkoxy group having 1 to 6 carbon atoms which has been substituted by a halogen atom or halogen atoms. The preferred number of the substituting halogen atoms is 1 to 3. Examples of the halo$C_{1-6}$ alkoxy group are a fluoromethoxy group, a difluoromethoxy group, and a trifluoromethoxy group.

The term "halo$C_{3-6}$ cycloalkyl group" as used herein refers to a cycloalkyl group having 3 to 6 carbon atoms which has been substituted by a halogen atom or halogen atoms. The preferred number of the substituting halogen atoms is 1 to 3. Examples of the halo$C_{3-6}$ cycloalkyl group are a fluorocyclopropyl group, a fluorocyclobutyl group, a fluorocyclopentyl group, a fluorocyclohexyl group, a difluorocyclopropyl group, and a difluorocyclobutyl group.

In the definition of $R^9$ and $R^{10}$ herein, "taken together with the nitrogen atom to which they bind represent a 4- to 6-membered cyclic structure", an azetidine ring, a pyrrolidine ring, and a piperidine ring are named as examples of the 4- to 6-membered cyclic structure. Moreover, a ring structure containing a hetero atom in the ring, such as a morpholine ring or a thiomorpholine ring, is also included in the examples.

The term "$C_{1-3}$ alkylene group" as used herein refers to a straight-chain or branched-chain alkylene group having 1 to 3 carbon atoms, and includes, for example, a methylene group, an ethylene group, and a propylene group.

The term "monocyclic or bicyclic heteroaryl group" as used herein refers to a monocyclic or bicyclic heteroaryl group having in the ring at least one atom selected from a group consisting of a nitrogen atom, an oxygen atom, and a sulfur atom.

The monocyclic heteroaryl group is preferably a 5- or 6-membered heteroaryl group which includes, for example, a pyridyl group, a pyrimidyl group, a pyrazyl group, a pyrazolyl group, a thiazolyl group, an imidazolyl group, an oxazolyl group, an isoxazolyl group, a thienyl group, a triazolyl group, and an oxadiazolyl group. The "divalent monocyclic heteroaryl group" as used herein includes, for example, groups formed by eliminating any one hydrogen atom from each of the aforementioned groups.

The bicyclic heteroaryl group is preferably a 9- or 10-membered heteroaryl group, its examples including an indolyl group, a benzofuranyl group, a quinolyl group, and an isoquinolyl group.

The term "pharmaceutically acceptable salt" as used herein refers to "an acid addition salt which can be accepted in pharmaceutical terms. Examples of the acid to be used are inorganic acids such as sulfuric acid, hydrochloric acid, hydrobromic acid, nitric acid and phosphoric acid, or organic acids such as acetic acid, oxalic acid, lactic acid, citric acid, malic acid, gluconic acid, tartaric acid, fumaric acid, maleic acid, methanesulfonic acid, ethanesulfonic acid, benzenesulfonic acid, and p-toluenesulfonic acid. Conversion from the free form to the salt of interest can be performed by conventional methods.

In connection with the inventive compounds, preferred embodiments will be mentioned below.

Compounds wherein $R^1$ is a $C_{1-6}$ alkyl group are preferred. Compounds wherein $R^1$ is a methyl group are more preferred.

Compounds wherein $R^2$ is a) a $C_{1-6}$ alkyl group which may be substituted by 1 to 3 substituents selected from among a $C_{1-6}$ alkoxyl group, a halogen atom, and a $C_{3-6}$ cycloalkyl group, or b) a $C_{3-6}$ cycloalkyl group are preferred. Compounds wherein $R^2$ is a branched-chain $C_{3-6}$ alkyl group or a $C_{4-8}$ cycloalkyl group are more preferred.

Compounds wherein $R^3$ and $R^4$ are each a hydrogen atom are preferred.

Compounds wherein Y is the formula CH are preferred.

Compounds wherein $Ar^1$ is a 1,3-phenylene group, a pyridine-2,4-diyl group (with the carbon atom adjacent to the nitrogen atom binding to $Ar^2$), a pyrimidine-2,4-diyl group, an isoxazole-3,5-diyl group, an oxadiazole-3,5-diyl group, a thiazole-2,4-diyl group, or a pyrazole-1,4-diyl group, any of which may be substituted by a halogen atom, are preferred.

Compounds are preferred, wherein $Ar^2$ is a phenyl group, a naphthyl group, a pyridyl group, a pyrimidyl group, a pyrazyl group, a pyrazolyl group, an imidazolyl group, a thienyl group, an imidazo[1,2-a]pyridyl group, or a quinolyl group, provided that the phenyl group, the naphthyl group, the pyridyl group, the pyrimidyl group, the pyrazyl group, the pyrazolyl group, the imidazolyl group, the thienyl group, the imidazo[1,2-a]pyridyl group, or the quinolyl group may be substituted by 1 to 5 substituents selected from Group 3 of substituents. Compounds are more preferred, wherein $Ar^2$ is a phenyl group which may be substituted by 1 to 5 substituents selected from Group 4 of substituents, a pyridyl group which may be substituted by 1 to 4 substituents selected from Group 5 of substituents, a pyrimidyl group which may be substituted by 1 to 3 substituents selected from Group 5 of substituents, or a pyrazyl group which may be substituted by 1 to 3 substituents selected from Group 5 of substituents. Even more preferred are compounds wherein $Ar^2$ is a phenyl group substituted by 1 to 5 halo$C_{1-6}$ alkoxy groups.

The inventive compounds can contain a plurality of asymmetric centers. The aforementioned compounds, therefore, can be present not only in optically active forms, but also in their racemic modifications. Further, a plurality of diastereomers can also be present. All of these forms are included in the scope of the present invention. Respective isomers can be obtained by known methods, for example, the use of optically active starting materials or intermediates, an optically selective reaction or a diastereoselective reaction in the manufacture of an intermediate or a final product, or a chromatographic separation in the manufacture of an intermediate or a final product. If the inventive compounds form hydrates or solvates, they are also included in the scope of the present invention. Likewise, pharmaceutically acceptable salts of the hydrates or solvates of the inventive compounds are also included in the scope of the present invention.

The compounds according to the present invention can be administered orally or parenterally. Their administration dosage forms are tablets, capsules, granules, dispersions, powders, lozenges, ointments, creams, emulsions, suspensions, suppositories, injections, etc. All of them can be produced by conventional pharmaceutical technologies (for example, methods set forth in the 15$^{th}$ revised Japanese Pharmacopoeia). These administration dosage forms can be selected, as appropriate, according to the symptoms and age of the patient and the purpose of treatment.

These preparations can be produced from the composition containing the compound of the present invention by incorporating in it one or more pharmacologically acceptable carriers, namely, an excipient (for example, microcrystalline cellulose, starch, lactose or mannitol), a binder (for example, hydroxypropyl cellulose or polyvinyl pyrrolidone), a lubricant (for example, magnesium stearate, or talc), a disintegrant (for example, carboxymethylcellulose calcium), and various other pharmacologically acceptable additives.

The inventive compound may be used in combination with 1 or more other therapeutics, namely various antipsychotics, antidepressants, for example, 5HT3 antagonists, 5HT2 antagonists, serotonin agonists, NK-1 antagonists, selective serotonin reuptake inhibitors (SSRI), serotonin noradrenaline reuptake inhibitors (SNRI), tricyclic antidepressants, dopaminergic antidepressants, H3 antagonists, 5HT1A antagonists, 5HT1B antagonists, 5HT1D antagonists, D1 agonists, M1 agonists, anticonvulsants, cognitive enhancement drugs, and other psychoactive drugs.

Examples of other drugs which may be used in combination with the compounds of the present invention are ondansetron, granisetron, metoclopramide, sumatriptan, rauwolscine, yohimbine, metoclopramide, fluoxetine, citalopram, escitalopram, femoxetine, fluvoxamine, paroxetine, indalpine, sertraline, zimeldine, venlafaxine, reboxetine, Milnacipran, duloxetine, imipramine, amitriptiline, chlomipramine, nortriptiline, bupropion, aimineptine, divalproex, carbamazepine, diazepam, risperidone, olanzapine, ziprasidone, aripiprazole, quetiapine, perospirone, clozapine, haloperidol, pimozide, droperidol, chlorpromazine, thioridazine, mesoridazine, trifluoperazine, perphenazine, fluphenazine, thiflupromazine, prochlorperazine, acetophenazine, thiothixene, chlorprothixene, lamotrigine, loxapine, and molindone. Such combinations may be administered simultaneously (in the same pharmaceutical formula or in different pharmaceutical formulations), separately or sequentially.

Particular advantages associated with the use of, and methods for treatment with, combinations of the inventive compounds include, for example, comparable or improved effects achieved in smaller doses than the usually used doses of individual ingredients. Such combined use and treatment methods are also expected to further enhance therapeutic effects on positive symptoms and/or negative symptoms of psychiatric disorder and/or cognitive dysfunction. The use of and methods for treatment with combinations of the inventive compounds can provide advantage in the treatment of patients who do not sufficiently respond to, or who are resistant to, treatment with certain neuroleptics.

The compounds according to the present invention may be administered in doses which, in the case of treating adults, range from 1 to 2000 mg per day, either once daily or in divided portions. The dose may be appropriately adjusted depending on the age, body weight and symptom of the patient.

The compounds of formula [I] can be produced by various methods of synthesis. The methods described below are only illustrative of the process for producing the inventive compounds and should not be taken as limiting.

In the general production processes, the "inert solvent" may be exemplified by alcohols such as methanol, ethanol, isopropanol, n-butanol, and ethylene glycol; ethers such as diethyl ether, t-butyl methyl ether, diisopropyl ether, tetrahydrofuran, 1,4-dioxane, and 1,2-dimethoxyethane; hydrocarbons such as pentane, hexane, heptane, toluene, benzene, and xylene; esters such as ethyl acetate and ethyl formate; ketones such as acetone and methyl ethyl ketone; halogenated carbon-based solvents such as chloroform and dichloromethane; amides such as dimethylformamide and N-methylpyrrolidone; acetonitrile; dimethyl sulfoxide; water; and mixed solvents thereof.

The "base" may be exemplified by alkali metal or alkaline earth metal hydrides such as lithium hydride, sodium hydride, potassium hydride, and calcium hydride; alkali metal or alkaline earth metal amides such as lithium amide, sodium amide, lithium diisopropylamide, lithium dicyclohexylamide, lithium hexamethyldisilazide, sodium hexamethyldisilazide, and potassium hexamethyldisilazide; alkali metal or alkaline earth metal lower alkoxides such as sodium methoxide, sodium ethoxide, and potassium tert-butoxide; alkyl lithium compounds such as butyl lithium, sec-butyl lithium, tert-butyl lithium, and methyl lithium; alkali metal or alkaline earth metal hydroxides such as sodium hydroxide, potassium hydroxide, lithium hydroxide, and barium hydroxide; alkali metal or alkaline earth metal carbonates such as sodium carbonate, potassium carbonate, and cesium carbonate; alkali metal or alkaline earth metal hydrogencarbonates such as sodium hydrogen carbonate, and potassium hydrogen carbonate; amines such as triethylamine, N-methylmorpholine, N,N-diisopropylethylamine, 1,8-diazabicyclo[5.4.0]undec-7-ene (DBU), 1,5-diazabicyclo[4.3.0]non-5-ene (DBN), and N,N-dimethylaniline; and basic heterocyclic compounds such as pyridine, imidazole, and 2,6-lutidine. These bases may be selected, as appropriate, depending on various reaction conditions known to skilled artisans.

The "acid" may be exemplified by inorganic acids such as hydrochloric acid, hydrobromic acid, sulfuric acid, nitric acid and phosphoric acid; and organic acids such as p-toluenesulfonic acid, methanesulfonic acid, trifluoroacetic acid, formic acid, acetic acid, citric acid, and oxalic acid. These acids may be selected, as appropriate, depending on various reaction conditions known to skilled artisans.

The "Lewis acid" may be exemplified by boron trifluoride, aluminum trichloride, titanium tetrachloride, iron trichloride, zinc chloride, and tin tetrachloride.

In the formula, $X^1$ represents a halogen atom such as a fluorine atom, a chlorine atom, a bromine atom, or an iodine atom, or an organosulfonyloxy group such as a methanesulfonyloxy group, a phenylsulfonyloxy group, a p-toluenesulfonyloxy group, or a trifluoromethanesulfonyloxy group; $X^2$ represents a halogen atom or a hydroxy group; M represents a substituent generally used in a coupling reaction (the substituent being exemplified by a group containing an atom such as boron, tin, zinc, silicon or magnesium, more preferably exemplified by a borate group, a diethylboryl group, a 4,4,5,5-tetramethyl-[1,3,2]dioxaborolanyl group, or a tri-n-butyl-stannyl group; Z represents a group having a carbonyl group, such as a carboxylic acid or an ester, and preferably represents an ester; $R^a$ represents a $C_{1-6}$ alkyl group; $R^b$ and $R^c$ independently represent a $C_{1-5}$ alkyl group, a hydrogen atom, or a $C_{3-6}$ cycloalkyl group, provided that the $C_{1-5}$ alkyl group may be substituted by 1 to 3 substituents selected from among a $C_{1-6}$ alkoxy group, a halogen atom, a $C_{3-6}$ cycloalkyl group, and a halo$C_{1-6}$ alkoxy group; or $R^b$ and $R^c$ may, together with the carbon atom to which they are bound, form a $C_{3-6}$ cycloalkyl ring, a halo$C_{3-6}$ cycloalkyl ring, or the formula [II]; $Ar^a$ represents an imidazolyl group optionally having a substituent, a pyrazolyl group optionally having a substituent, or a triazolyl group optionally having a substituent; and the other symbols are as defined above.

General Production Process 1

[Chem 4]

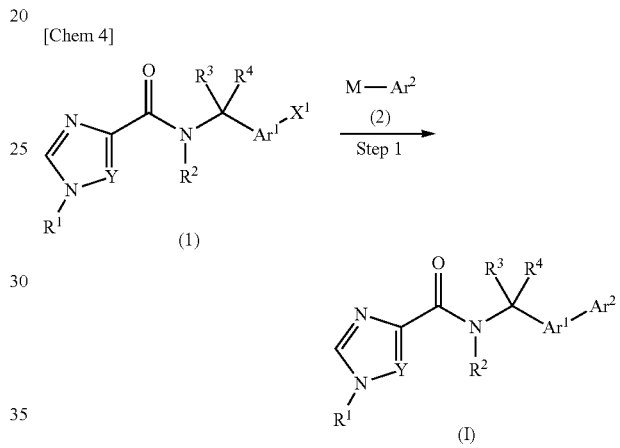

Step 1: Compound (2) may be reacted with compound (1) by using a palladium catalyst, and if desired a ligand for the palladium catalyst, in an inert solvent in the presence or absence of a base, to thereby obtain the inventive compound (I).

The palladium catalyst here mentioned may be exemplified by palladium acetate, tris(dibenzylideneacetone)dipalladium, tetraquistriphenylphosphine palladium, (1,3-diisopropylimidazol-2-ylidene)(3-chloropyridyl)palladium(II) dichloride, [1,3-bis(2,6-diisopropylphenyl)imidazol-2-ylidene](3-chloropyridyl)palladium(II) dichloride, and chloro[1,1'-bis(diphenylphosphino)ferrocene]palladium. The ligand here mentioned may be exemplified by triphenylphosphine, 2,2-bis(diphenylphosphino)-1,1-binaphthyl (BINAP), 2-(di-tert-butylphosphino)biphenyl, and 9,9-dimethyl-4,5-bis(diphenylphosphino)xanthene (Xantphos).

General Production Process 2

[Chem 5]

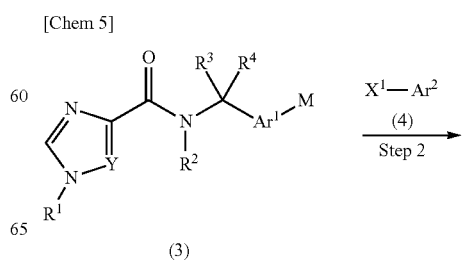

-continued

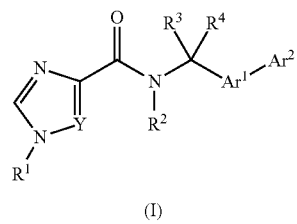

(I)

Step 2: The inventive compound (I) may be obtained from compound (3) and compound (4) in the same manner as in step 1 of the general production process 1.

General Production Process 3

[Chem 6]

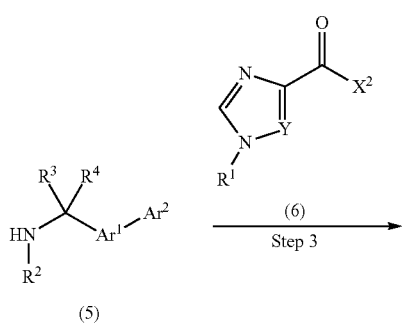

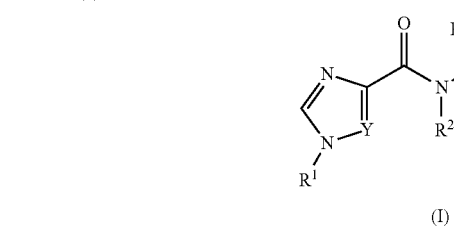

(I)

Step 3: Compound (5) and compound (6) where $X^2$ is a halogen atom may be reacted in an inert solvent in the presence or absence of a base to obtain the inventive compound (I). Alternatively, compound (5) and compound (6) where $X^2$ is a hydroxyl group are subjected to various types of amidation reaction known to skilled artisans, to thereby obtain the inventive compound (I). The amidation reaction here mentioned may be exemplified by amidation reaction as performed in an inert solvent in the presence or absence of a base using a condensing agent such as O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU), N,N'-dicyclohexylcarbodiimide (DCC), 1-ethyl-3-(3-dimethylaminopropyl)carbodiimide hydrochloride (EDC.HCl), 4-(4,6-dimethoxy-1,3,5-triazin-2-yl)-4-methylmorpholinium chloride (DMT-MM), diphenylphosphorylazide (DPPA), or carbonyldiimidazole (CDI); and amidation reaction via mixed acid anhydride as performed by use of ethyl chlorocarbonate, isobutyl chlorocarbonate or trimethylacetyl chloride. To perform the above amidation reaction using a condensing agent, an additive such as 1-hydroxybenzotriazole (HOBt) or hydroxysuccinimide (HOSu) may also be employed depending on the need.

General Production Process 4

[Chem 7]

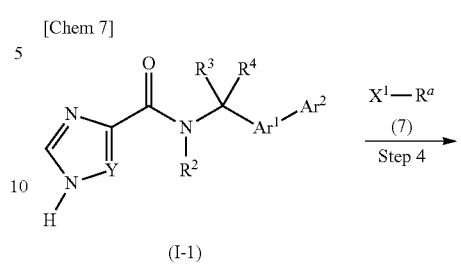

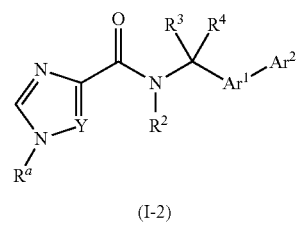

Step 4: Compound (I-1) according to the present invention and compound (7) may be reacted in an inert solvent in the presence or absence of a base, to thereby obtain the inventive compound (I-2).

General Production Process 5

[Chem 8]

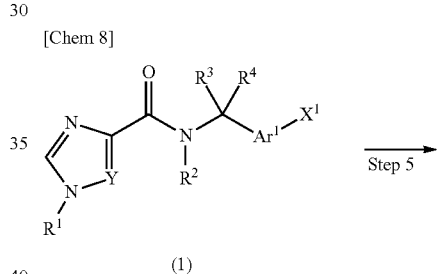

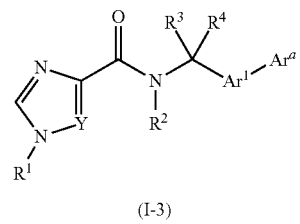

Step 5: Imidazole optionally having a substituent, pyrazole optionally having a substituent, or triazole optionally having a substituent may be reacted with compound (1) in the presence of a copper catalyst and an amine ligand in an inert solvent in the presence or absence of a base, to thereby obtain the inventive compound (I-3).

The copper catalyst here mentioned may be exemplified by copper(I) oxide, copper(I) iodide, copper(I) bromide, and copper(I) acetate. The amine ligand here mentioned may be exemplified by N,N-dimethylethylenediamine, 1,2-cyclohexanediamine, phenanthroline, and L-proline.

General Production Process 6
[Chem 9]
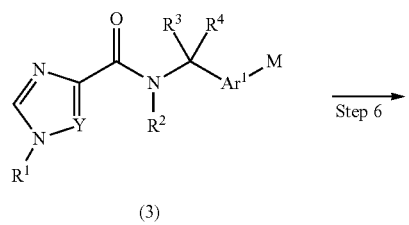
Step 6: The inventive compound (I-3) may be obtained from compound (3) in the same manner as in step 5 of the general production process 5.
General Production Process 7
[Chem 10]
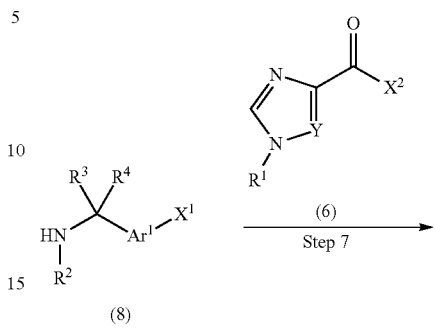
Step 7: Compound (1) may be synthesized from compound (8) and compound (6) in the same manner as in step 3 of the general production process 3.
General production process 8
[Chem 11]
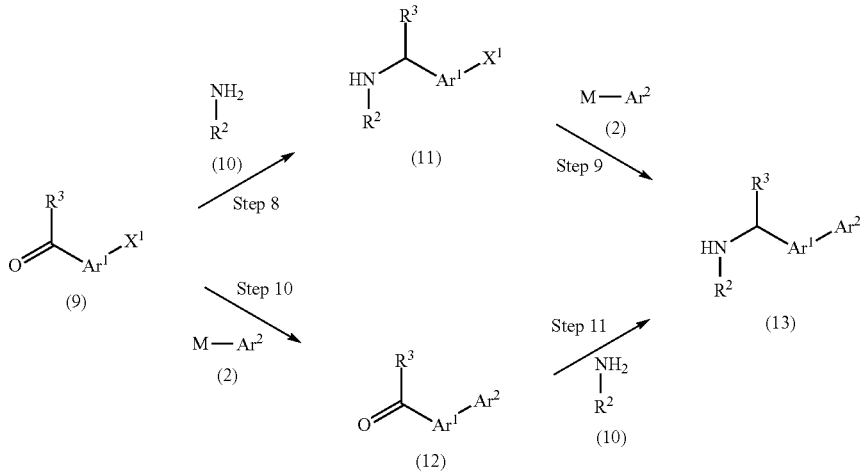

Step 8: Compound (9) and compound (10) may be subjected to reductive amination reaction using a reducing agent in an inert solvent in the presence or absence of an acid and in the presence or absence of a base, to thereby obtain compound (11). The reducing agent here mentioned may be exemplified by sodium triacetoxyborohydride, sodium cyanoborohydride, and sodium borohydride.

Step 9: Compound (13) may be synthesized from compound (11) and compound (2) in the same manner as in step 1 of the general production process 1.

Step 10: Compound (12) may be synthesized from compound (9) and compound (2) in the same manner as in step 1 of the general production process 1.

Step 11: Compound (13) may be synthesized from compound (12) and compound (10) in the same manner as in step 8 of the general production process 8.

General Production Process 9

[Chem 12]

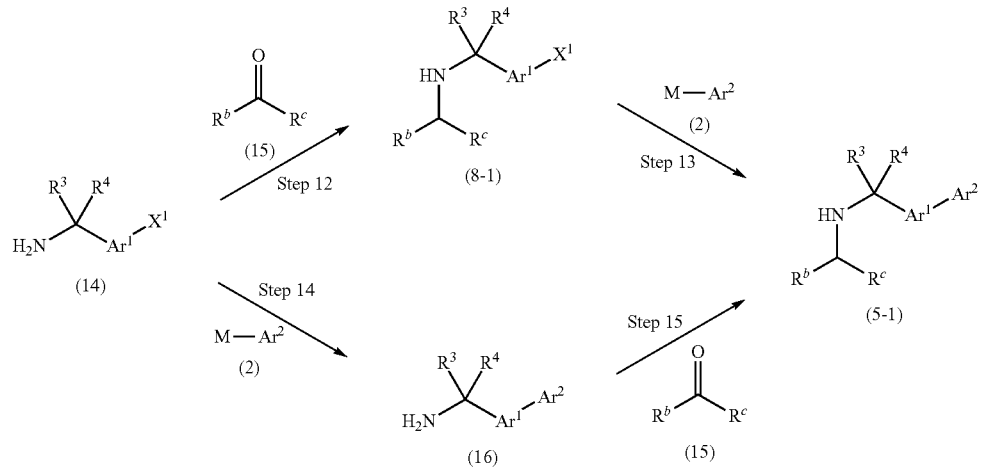

Step 12: Compound (8-1) may be synthesized from compound (14) and compound (15) in the same manner as in step 8 of the general production process 8. Compound (8-1) is a compound which is included in compounds expressed as compound (8).

Step 13: Compound (5-1) may be synthesized from compound (8) and compound (2) in the same manner as in step 1 of the general production process 1. Compound (5-1) is a compound which is included in compounds expressed as compound (5).

Step 14: Compound (16) may be synthesized from compound (14) and compound (2) in the same manner as in step 1 of the general production process 1.

Step 15: Compound (5-1) may be synthesized from compound (16) and compound (15) in the same manner as in step 8 of the general production process 8.

General Production Process 10.

[Chem 13]

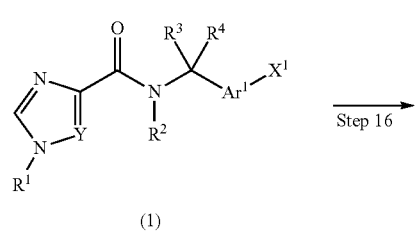

-continued

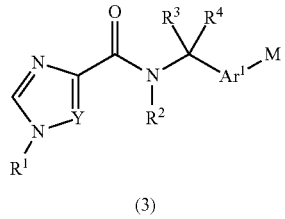

Step 16: Compound (3) may be synthesized from compound (1) by the method described in J. Org. Chem., 60, 7508-7510 (1995).

General Production Process 11

[Chem 14]

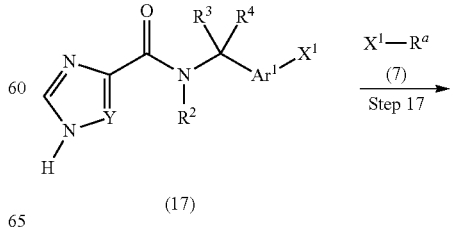

-continued

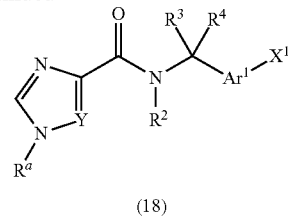

(18)

Step 17: Compound (18) may be synthesized from compound (17) and compound (7) in the same manner as in step 4 of the general production process 4.

General Production Process 12

[Chem 15]

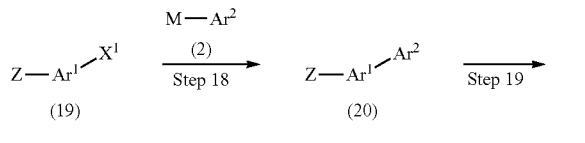

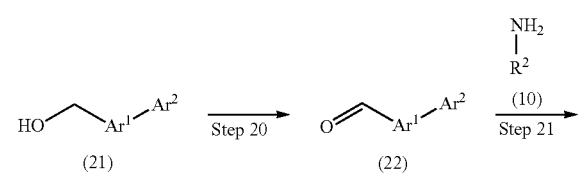

Step 18: Compound (20) may be synthesized from compound (19) and compound (2) in the same manner as in step 1 of the general production process 1.

Step 19: Compound (20) may be subjected to conventional reduction reaction for conversion into an alcohol, with the use of a reducing agent in an inert solvent in the presence or absence of an acid, to thereby obtain compound (21). The reducing agent here mentioned may be exemplified by lithium aluminum hydride, diisopropyl aluminum hydride, diisobutyl aluminum hydride, and lithium borohydride.

Step 20: Compound (21) may be subjected to conventional oxidation reaction for conversion from an alcohol into an aldehyde with the use of an oxidizing agent in an inert solvent, to thereby obtain compound (22). The oxidizing agent here mentioned may be exemplified by manganese dioxide, 2-iodoxybenzoic acid, and 1,1,1-triacetoxy-1,1-dihydro-1,2-benziodoxol-3(1H)-one.

The present compound (22) may also be produced from compound (20) by a one-stage reaction.

Step 21: Compound (23) may be synthesized from compound (22) and compound (10) in the same manner as in step 8 of the general production process 8.

General Production Process 13

[Chem 16]

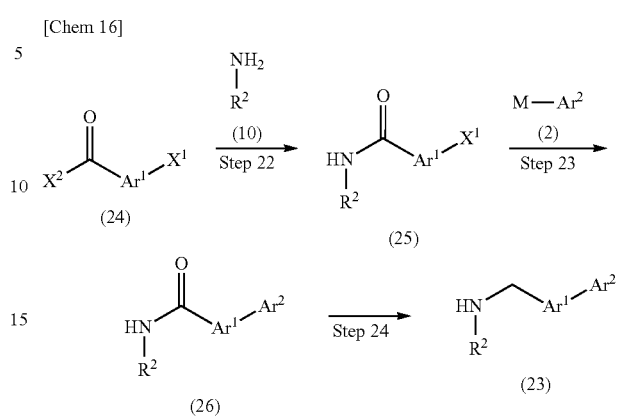

Step 22: Compound (25) may be synthesized from compound (24) and compound (10) in the same manner as in step 3 of the general production process 3.

Step 23: Compound (26) may be synthesized from compound (25) and compound (2) in the same manner as in step 1 of the general production process 1.

Step 24: Compound (26) as amide may be reduced for conversion into an amine in an inert solvent using a reducing agent, to thereby synthesize compound (23). The reducing agent herein mentioned may be exemplified by lithium aluminum hydride, diborane, and sodium borohydride (in the presence or absence of Lewis acid).

EXAMPLES

Next, the present invention will be described in greater detail by means of Production Examples, Working Examples and Test Examples, but it should be understood that those Examples are by no means intended to limit the present invention.

The "NH2 cartridge" used in post-reaction treatment was Waters (registered trademark) Sep-Pak Amino Propyl (NH2).

The microwave reaction apparatus used in Production Examples and Working Examples described below was Initiator from Biotage.

In the case of purification by column chromatography in Production Examples and Working Examples below, SNAP Cartridge KP-NH from Biotage was used as the "NH silica gel cartridge", SNAP Cartridge KP-Sil or HP-Sil both from Biotage was used as the "silica gel cartridge", and Purif-Pack ODS from MORITEX was used as the "reversed-phase silica gel cartridge".

In the case of purification by means of preparative thin-layer chromatography (PTLC) in Production Examples and Working Examples below, NH2 Silica Gel 60F254 Plate Wako (20 cm×20 cm) from Wako Pure Chemical Industries, Ltd. was used as the "NH silica gel", and Silica Gel 60F254 (20 cm×20 cm) from Merck was used as the "silica gel".

In Production Examples and Working Examples below, the purification by preparative high performance liquid chromatography (HPLC) was performed under the following conditions. When trifluoroacetic acid was used in the main procedure for producing compounds having a basic functional group, neutralization or a like operation was conducted as appropriate for obtaining the compounds in their free form.

Apparatus: Preparative HPLC System, from Gilson

Column: Capcelpak C18 MGII 5 μm 20×150 mm, from Shiseido

Solvent: A-liquid; 0.1% trifluoroacetic acid-containing water, B-liquid; 0.1% trifluoroacetic acid-containing acetonitrile Gradient: 0 min (A-liquid/B-liquid=90/10), 22 min (A-liquid/B-liquid=20/80), 25 min (A-liquid/B-liquid=10/90)

Flow rate: 20 mL/min, Detectoin method: UV 254 nm

Nuclear magnetic resonance spectra (NMR) were used for the structure confirmation in Production Examples and Working Examples below. The nuclear magnetic resonance spectra (NMR) were measured under the following conditions.

NMR measurement apparatus: JNM-ECA600 (600 MHz) from JEOL, JNM-ECA500 (500 MHz) from JEOL, UNITYNOVA300 (300 MHz) from Varian, GEMINI2000/200 (200 MHz) from Varian In Production Examples and Working Examples below, mass spectra (MS) were measured under the following conditions.

MS measurement apparatus: LCMS-2010EV from Shimazu or Platform LC from Micromass In Production Examples and Working Examples below, high-performance liquid chromatography mass spectra (LCMS) were measured under the following conditions.

Measurement apparatus: Platform LC from Micromass and Agilent 1100 from Agilent

Column: SunFire C18 2.5 μm 4.6×50 mm from Waters

Solvent: 0.1% trifluoroacetic acid-containing water, B-liquid; 0.1% trifluoroacetic acid-containing acetonitrile Gradient: 0 min (A-liquid/B-liquid=90/10), 0.5 min (A-liquid/B-liquid=90/10), 5.5 min (A-liquid/B-liquid=20/80), 6.0 min (A-liquid/B-liquid=1/99), 6.3 min (A-liquid/B-liquid=1/99)

Flow rate: 1 mL/min, Detection method: 254 nM

Ionization method: electron ionization (ESI: Electron Spray Ionization)

In Production Examples and Working Examples below, compounds were named in accordance with the ACD/Name (ACD/Labs 12.01, Advanced Chemistry Development Inc.)

In Production Examples and Working Examples below, compounds with basic functional groups may be converted into salts using various acids under various reaction conditions known to skilled artisans.

Production Example 1

6-Bromo-5-fluoropyridine-2-carbaldehyde

[Chem 17]

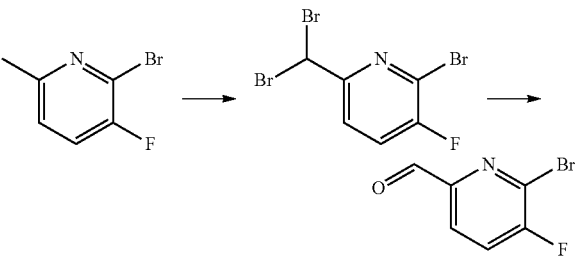

(1) To a solution of 2-bromo-3-fluoro-6-picoline (500 mg) in carbon tetrachloride (10 mL) were added N-bromosuccinimide (940 mg) and benzoyl peroxide (102 mg), and the mixture was stirred while heating at 80° C. for 5 hr. After stirring at room temperature for 16.5 hr, additional N-bromosuccinimide (90 mg) and benzoyl peroxide (20 mg) were added, and the mixture was stirred while heating at 80° C. for 5 hr. After stirring at room temperature for 18 hr, the insoluble matter was filtered off and washed with chloroform. The solvent was distilled off under reduced pressure, and the resulting residue was purified by column chromatography (silica gel cartridge, hexane:ethyl acetate=98:2-82:18) and (silica gel cartridge and NH silica gel cartridge, hexane:ethyl acetate=98:2-82:18) to afford 2-bromo-6-(dibromomethyl)-3-fluoropyridine (663 mg).

1H NMR (600 MHz, CHLOROFORM-d) d ppm 6.59 (s, 1H), 7.48-7.54 (m, 1H), 7.84 (dd, J=8.3, 3.2 Hz, 1H)

(ESI pos.) m/z: 345([M+H]+), 347([M+3]+), 349([M+5]+), 351([M+7]+)

(2) After a solution of 2-bromo-6-(dibromomethyl)-3-fluoropyridine (615 mg) and calcium carbonate (391 mg) in dimethylsulfoxide (6.5 mL) was stirred while heating at 150° C. for 4.5 hr, the reaction mixture was reverted to room temperature and stirred for 15.5 hr. After water was added thereto, the mixtue was stirred and then extracted with ethyl acetate. The organic phase was washed with water and brine, and the solvent was then distilled off under reduced pressure. The resulting residue was purified by column chromatography (silica gel cartridge, hexane:ethyl acetate=98:2-82:18) to afford the title compound (240 mg).

1H NMR (600 MHz, CHLOROFORM-d) d ppm 7.48-7.77 (m, 1H), 7.79-8.18 (m, 1H), 9.98 (s, 1H)

(ESI pos.) m/z: 204([M+H]+), 206([M+3]+)

Production Example 2

6-Bromo-5-fluoropyridine-2-carbaldehyde

[Chem 18]

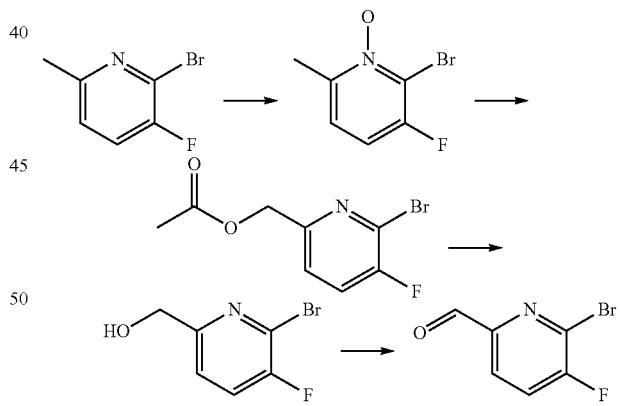

(1) To an ice-cold solution of 2-bromo-3-fluoro-6-picoline (1.00 g) in chloroform (25 mL) was added 3-chloroperoxybenzoic acid (1.77 g), and the mixture was stirred while warming to room temperature for 22 hr. After cooling in ice again, additional 3-chloroperoxybenzoic acid (590 mg) was added and the mixture was stirred while warming to room temperature for 21 hr. An aqueous sodium thiosulfate solution was added to the reaction mixture, and the resulting mixture was then stirred. Thereafter, saturated aqueous sodium hydrogen carbonate solution and water were added thereto, followed by extraction with chloroform. The organic phase was washed with brine, and the solvent was then distilled off under reduced pressure. The resulting residue was purified by column chromatography (silica gel cartridge, hexane:ethyl acetate=98:2-0:100) to afford 2-bromo-3-fluoro-6-methylpyridine 1-oxide (604 mg).

1H NMR (600 MHz, CHLOROFORM-d) d ppm 2.55 (s, 3H), 6.99-7.03 (m, 1H), 7.17-7.22 (m, 1H)

(ESI pos.) m/z: 206([M+H]+), 208([M+3]+)

(2) A solution of 2-bromo-3-fluoro-6-methylpyridine 1-oxide (585 mg) in acetic anhydride (4.98 mL) was stirred while heating at 120° C. for 4 hr. After returning the solution to room temperature, methanol (25 mL) was gradually added dropwise thereto. After the solvent was distilled off under reduced pressure, the acetic anhydride was evaporated with methanol. The resulting residue was purified by column chromatography (silica gel cartridge, hexane:ethyl acetate=88:12-0:100) to afford (6-bromo-5-fluoropyridin-2-yl)methyl acetate (269 mg).

1H NMR (600 MHz, CHLOROFORM-d) d ppm 2.16 (s, 3H), 5.17 (s, 2H), 7.33 (dd, J=8.3, 3.7 Hz, 1H), 7.43 (dd, J=8.3, 7.3 Hz, 1H)

(ESI pos.) m/z: 248([M+H]+), 250([M+3]+)

(3) To a solution of (6-bromo-5-fluoropyridin-2-yl)methyl acetate (240 mg) in methanol (2.50 mL) was added an aqueous solution of 1M potassium carbonate (1.64 mL) and the mixture was stirred at room temperature for 20.5 hr. After the solvent was distilled off under reduced pressure, water was added, followed by exraction with chloroform. The organic phase was separated out and the solvent was distilled off under reduced pressure to afford (6-bromo-5-fluoropyridin-2-yl)methanol (215 mg) as the residue.

1H NMR (600 MHz, CHLOROFORM-d) d ppm 2.75 (t, J=5.7 Hz, 1H), 4.75 (d, J=5.5 Hz, 2H), 7.29-7.33 (m, 1H), 7.41-7.46 (m, 1H)

(ESI pos.) m/z: 206([M+H]+), 208([M+3]+)

(4) Manganese dioxide (695 mg) was added to a solution of (6-bromo-5-fluoropyridin-2-yl)methanol (200 mg) in chloroform (3.00 mL) and the mixture was stirred while heating at 70° C. for 12 hr. After stirring at room temperature for 13 hr, the reaction mixture was filtered through Celite. The solvent was distilled off under reduced pressure, and the resulting residue was purified by column chromatography (silica gel cartridge, hexane:ethyl acetate=98:2-82:18) to afford the title compound (81 mg).

1H NMR (600 MHz, CHLOROFORM-d) d ppm 7.57-7.61 (m, 1H), 7.96-8.00 (m, 1H), 9.98 (s, 1H)

Production Example 3

4-Iodo-1-methylpyridin-2(1H)-one

[Chem 19]

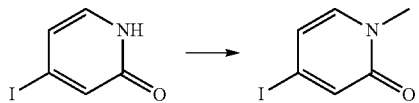

A solution of 4-iodo-2-pyridone (500 mg), sodium hydride (109 mg) and methyl iodide (482 mg) in dimethylformamide (5.0 mL) was stirred at room temperature for 4 hr. Additional sodium hydride (109 mg) and methyl iodide (482 mg) were added and the mixture was stirred at room temperature for 2 hr. The reaction mixture was diluted with chloroform and washed with saturated aqueous sodium hydrogen carbonate solution. After extraction with chloroform, the organic phase was dried over anhydrous magnesium sulfate. The desiccant was filtered off, and the solvent was then distilled off under reduced pressure. The resulting residue was purified by column chromatography (silica gel cartridge, chloroform:methanol=98:2-96:4) to afford the title compound (341 mg).

1H NMR (600 MHz, CHLOROFORM-d) d ppm 3.48 (s, 3H), 6.45-6.49 (m, 1H), 6.96 (d, J=6.9 Hz, 1H), 7.09 (d, J=1.8 Hz, 1H)

(ESI pos.) m/z: 236([M+H]+)

Production Example 4

2-[4-Fluoro-3-(trifluoromethoxy)phenyl]-4,4,5,5-tetramethyl-1,3,2-dioxaborolane

[Chem 20]

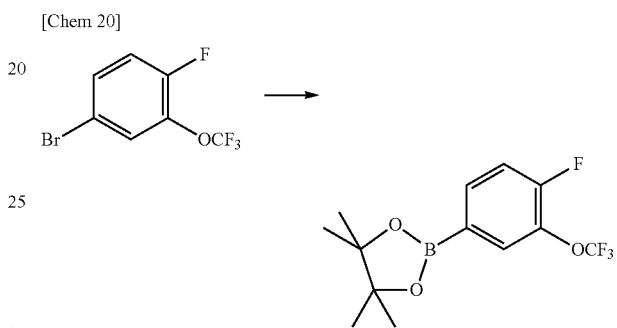

A solution of 2-fluoro-5-bromo-trifluoromethoxybenzene (500 mg), bis(pinacolate)diborane (600 mg), [1,1'-bis(diphenylphosphino)ferrocene]dichloropalladium (II) (158 mg) and potassium acetate (586 mg) in dimethyl sulfoxide (5.0 mL) was stirred under nitrogen atmosphere while heating at 100° C. for 3 hr. Water was added to the reaction mixture, which was then filtered through Celite and extracted with ethyl acetate. The organic phase was separated out and the solvent was distilled off under reduced pressure. The resulting residue was purified by column chromatography (silica gel cartridge, hexane:ethyl acetate=95:5-60:40) to afford the title compound (330 mg).

1H NMR (600 MHz, CHLOROFORM-d) d ppm 1.34 (br. s, 12H), 7.18 (dd, J=10.3, 8.5 Hz, 1H), 7.69-7.75 (m, 2H)

The following compound was synthesized according to the similar procedure. 4,4,5,5-Tetramethyl-2-[4-(pentafluoro-λ6-sulfanyl)phenyl]-1,3,2-dioxaborolane Production Example 5

N-[(2-Bromopyridin-4-yl)methyl]propan-2-amine

[Chem 21]

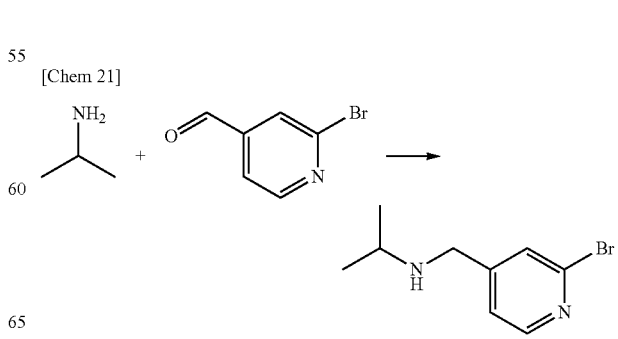

After a mixture of isopropylamine (2.8 mL), 2-bromopyridine-4-carboxaldehyde (3.00 g), and chloroform (60 mL) was stirred at room temperature, sodium triacetoxyborohydride (10.00 g) was added thereto and the mixture was stirred for 21 hr. Saturated aqueous sodium hydrogen carbonate solution was added to the reaction mixture, and the resulting mixture was then stirred for a while and extracted with chloroform. The organic phase was separated out and the solvent was distilled off under reduced pressure. The resulting residue was purified by column chromatography (silica gel cartridge, hexane:ethyl acetate=88:12-0:100) and (NH silica gel cartridge, hexane:ethyl acetate=90:10-0:100) to afford the title compound (2.64 g).

1H NMR (600 MHz, CHLOROFORM-d) d ppm 1.09 (s, 3H), 1.10 (s, 3H), 2.79-2.86 (m, 1H), 3.78 (s, 2H), 7.23 (dd, J=5.0, 0.9 Hz, 1H), 7.50 (d, J=0.9 Hz, 1H), 8.28 (d, J=5.0 Hz, 1H)

(ESI pos.) m/z: 229([M+H]+), 231([M+3]+)

The following compounds were synthesized according to the similar procedure.

N-[(6-Bromopyridin-2-yl)methyl]propan-2-amine

1H NMR (600 MHz, CHLOROFORM-d) d ppm 1.10 (s, 3H), 1.11 (s, 3H), 2.80-2.88 (m, 1H), 3.88 (s, 2H), 7.29 (d, J=7.3 Hz, 1H), 7.34 (d, J=7.8 Hz, 1H), 7.47-7.52 (m, 1H) (ESI pos.) m/z: 229([M+H]+), 231([M+3]+)

N-[(6-Bromo-5-fluoropyridin-2-yl)methyl]propan-2-amine

1H NMR (600 MHz, CHLOROFORM-d) d ppm 1.10 (s, 3H), 1.11 (s, 3H), 2.80-2.87 (m, 1H), 3.87 (s, 2H), 7.29-7.33 (m, 1H), 7.34-7.39 (m, 1H)

(ESI pos.) m/z: 247([M+H]+), 249([M+3]+)

N-[(6-Bromopyridin-2-yl)methyl]propan-1-amine

1H NMR (600 MHz, CHLOROFORM-d) d ppm 0.94 (t, J=7.3 Hz, 3H), 1.50-1.61 (m, 2H), 2.60-2.64 (m, 2H), 3.89 (s, 2H), 7.29 (d, J=7.3 Hz, 1H), 7.36 (d, J=7.8 Hz, 1H), 7.48-7.53 (m, 1H)

(ESI pos.) m/z: 229([M+H]+), 231([M+3]+)

N-[(6-Bromopyridin-2-yl)methyl]-2-methoxyethaneamine

1H NMR (600 MHz, CHLOROFORM-d) d ppm 2.81-2.85 (m, 2H), 3.36 (s, 3H), 3.50-3.54 (m, 2H), 3.92 (s, 2H), 7.31-7.36 (m, 2H), 7.50 (t, J=7.8 Hz, 1H)

(ESI pos.) m/z: 245([M+H]+), 247([M+3]+)

N-[(2-Bromopyridin-4-yl)methyl]propan-1-amine

1H NMR (600 MHz, CHLOROFORM-d) d ppm 0.94 (t, J=7.3 Hz, 3H), 1.47-1.57 (m, 2H), 2.54-2.60 (m, 2H), 3.79 (s, 2H), 7.23 (dd, J=5.0, 1.4 Hz, 1H), 7.48-7.51 (m, 1H), 8.29 (d, J=5.0 Hz, 1H)

(ESI pos.) m/z: 229([M+H]+), 231([M+3]+)

N-[(2-Bromopyridin-4-yl)methyl]-2-methylpropan-1-amine

1H NMR (600 MHz, CHLOROFORM-d) d ppm 0.93 (s, 3H), 0.93 (s, 3H), 1.71-1.79 (m, 1H), 2.39-2.42 (m, 2H), 3.78 (s, 2H), 7.22-7.24 (m, 1H), 7.50 (d, J=0.9 Hz, 1H), 8.29 (d, J=5.0 Hz, 1H)

(ESI pos.) m/z: 243([M+H]+), 245([M+3]+)

N-[(2-Bromopyridin-4-yl)methyl]pentan-3-amine

1H NMR (600 MHz, CHLOROFORM-d) d ppm 0.87-0.92 (m, 6H), 1.38-1.50 (m, 4H), 2.35-2.45 (m, 1H), 3.76 (s, 2H), 7.25 (d, J=5.0 Hz, 1H), 7.52 (s, 1H), 8.28 (d, J=5.0 Hz, 1H)

(ESI pos.) m/z: 257([M+H]+), 259([M+3]+)

N-[(2-Bromopyridin-4-yl)methyl]-2-methoxyethaneamine

1H NMR (600 MHz, CHLOROFORM-d) d ppm 2.77-2.80 (m, 2H), 3.37 (s, 3H), 3.50-3.53 (m, 2H), 3.81 (s, 2H), 7.21-7.25 (m, 1H), 7.51 (s, 1H), 8.26-8.31 (m, 1H)

(ESI pos.) m/z: 245([M+H]+), 247([M+3]+)

N-[(2-Bromopyridin-4-yl)methyl]-1,1,1-trifluoropropan-2-amine

1H NMR (600 MHz, CHLOROFORM-d) d ppm 1.28-1.31 (m, 3H), 3.07-3.26 (m, 1H), 3.91-3.96 (m, 2H), 7.25 (dd, J=5.0, 0.9 Hz, 1H), 7.52 (s, 1H), 8.31 (d, J=5.0 Hz, 1H)

(ESI pos.) m/z: 283([M+H]+), 285([M+3]+)

N-[(2-Bromopyridin-4-yl)methyl]-3,3,3-trifluoropropan-1-amine

1H NMR (600 MHz, CHLOROFORM-d) d ppm 2.28-2.39 (m, 2H), 2.85-2.91 (m, 2H), 3.81 (s, 2H), 7.23 (dd, J=5.0, 1.4 Hz, 1H), 7.50 (s, 1H), 8.31 (d, J=5.0 Hz, 1H)

(ESI pos.) m/z: 283([M+H]+), 285([M+3]+)

1-(2-Bromopyridin-4-yl)-N-(cyclopropylmethyl)methaneamine

1H NMR (600 MHz, CHLOROFORM-d) d ppm 0.10-0.14 (m, 2H), 0.47-0.53 (m, 2H), 0.92-1.00 (m, 1H), 2.46-2.50 (m, 2H), 3.82 (s, 2H), 7.21-7.25 (m, 1H), 7.51 (s, 1H), 8.29 (d, J=5.0 Hz, 1H)

(ESI pos.) m/z: 241([M+H]+), 243([M+3]+)

N-[(2-Bromopyridin-4-yl)methyl]cyclobutaneamine

1H NMR (600 MHz, CHLOROFORM-d) d ppm 1.57-1.77 (m, 4H), 2.18-2.27 (m, 2H), 3.22-3.29 (m, 1H), 3.70 (s, 2H), 7.19-7.24 (m, 1H), 7.49 (s, 1H), 8.28 (d, J=5.0 Hz, 1H)

(ESI pos.) m/z: 241([M+H]+), 243([M+3]+)

N-[(2-Bromopyridin-4-yl)methyl]cyclopentaneamine

1H NMR (600 MHz, CHLOROFORM-d) d ppm 1.21-1.89 (m, 8H), 3.06-3.12 (m, 1H), 3.77 (s, 2H), 7.22 (dd, J=5.0, 1.4 Hz, 1H), 7.48-7.51 (m, 1H), 8.28 (d, J=5.0 Hz, 1H)

(ESI pos.) m/z: 255([M+H]+), 257([M+3]+)

N-[(2-Bromopyridin-4-yl)methyl]cyclohexaneamine

1H NMR (600 MHz, CHLOROFORM-d) d ppm 1.03-1.95 (m, 10H), 2.40-2.47 (m, 1H), 3.81 (s, 2H), 7.23 (d, J=5.0 Hz, 1H), 7.50 (s, 1H), 8.28 (d, J=5.0 Hz, 1H)

(ESI pos.) m/z: 269([M+H]+), 271([M+3]+)

N-[(2-Bromopyridin-4-yl)methyl]tetrahydro-2H-pyran-4-amine

1H NMR (600 MHz, CHLOROFORM-d) d ppm 1.38-1.48 (m, 2H), 1.79-1.90 (m, 2H), 2.64-2.73 (m, 1H), 3.33-3.45 (m, 2H), 3.83 (s, 2H), 3.93-4.03 (m, 2H), 7.23-7.25 (m, 1H), 7.52 (s, 1H), 8.29 (d, J=4.6 Hz, 1H)

(ESI pos.) m/z: 271([M+H]+), 273([M+3]+)

1-(2-Bromopyridin-4-yl)-N-(tetrahydro-2H-pyran-4-ylmethyl)methaneamine

1H NMR (200 MHz, CHLOROFORM-d) d ppm 1.17-1.83 (m, 5H), 2.42-2.57 (m, 2H), 3.29-3.50 (m, 2H), 3.79 (s, 2H), 3.86-4.07 (m, 2H), 7.20-7.25 (m, 1H), 7.47-7.51 (m, 1H), 8.29 (d, J=4.4 Hz, 1H)

(ESI pos.) m/z: 285([M+H]+), 287([M+3]+)

N-[(2-Bromo-1,3-thiazol-4-yl)methyl]cyclobutaneamine

1H NMR (600 MHz, CHLOROFORM-d) d ppm 1.55-2.43 (m, 6H), 3.28-3.34 (m, 1H), 3.81 (s, 2H), 6.98-7.14 (m, 1H)

(ESI pos.) m/z: 247([M+H]+), 249([M+3]+)

N-[(2-Bromo-1,3-thiazol-4-yl)methyl]-2-methoxyethaneamine

1H NMR (600 MHz, CHLOROFORM-d) d ppm 2.81-2.84 (m, 2H), 3.34-3.38 (m, 3H), 3.49-3.53 (m, 2H), 3.91 (s, 2H), 7.09 (s, 1H)

(ESI pos.) m/z: 251([M+H]+), 253([M+3]+)

N-[(2-Bromo-1,3-thiazol-4-yl)methyl]tetrahydro-2H-pyran-4-amine

1H NMR (200 MHz, CHLOROFORM-d) d ppm 1.38-1.66 (m, 2H), 1.77-1.96 (m, 2H), 2.67-2.89 (m, 1H), 3.39 (td, J=11.8, 2.0 Hz, 2H), 3.86-4.10 (m, 4H), 7.09-7.22 (m, 1H)

(ESI pos.) m/z: 277([M+H]+), 279([M+3]+)

N-[(4-Bromo-1,3-thiazol-2-yl)methyl]tetrahydro-2H-pyran-4-amine

1H NMR (200 MHz, CHLOROFORM-d) d ppm 1.32-1.54 (m, 2H), 1.76-1.94 (m, 2H), 2.67-2.85 (m, 1H), 3.38 (td, J=11.6, 2.2 Hz, 2H), 3.91-4.05 (m, 2H), 4.14 (s, 2H), 7.15-7.24 (m, 1H)

(ESI pos.) m/z: 277([M+H]+), 279([M+3]+)

N-(3-Bromo-4-fluorobenzyl)cyclobutaneamine

1H NMR (200 MHz, CHLOROFORM-d) d ppm 1.54-1.83 (m, 4H), 2.09-2.30 (m, 2H), 3.14-3.37 (m, 1H), 3.65 (s, 2H), 6.98-7.10 (m, 1H), 7.16-7.25 (m, 1H), 7.53 (dd, J=6.6, 2.2 Hz, 1H)

(ESI pos.) m/z: 258([M+H]+), 260([M+3]+)

N-(3-Bromo-4-fluorobenzyl)tetrahydro-2H-pyran-4-amine

1H NMR (200 MHz, CHLOROFORM-d) d ppm 1.30-1.56 (m, 2H), 1.72-1.94 (m, 2H), 2.59-2.79 (m, 1H), 3.39 (td, J=11.6, 2.2 Hz, 2H), 3.78 (s, 2H), 3.90-4.04 (m, 2H), 7.00-7.11 (m, 1H), 7.18-7.29 (m, 1H), 7.55 (dd, J=6.6, 2.2 Hz, 1H)

(ESI pos.) m/z: 288([M+H]+), 290([M+3]+)

N-(3-Bromo-4-fluorobenzyl)propan-2-amine

1H NMR (200 MHz, CHLOROFORM-d) d ppm 1.07 (s, 3H), 1.11 (s, 3H), 2.70-2.94 (m, 1H), 3.73 (s, 2H), 7.00-7.10 (m, 1H), 7.18-7.25 (m, 1H), 7.53 (dd, J=6.6, 2.2 Hz, 1H)

(ESI pos.) m/z: 246([M+H]+), 248([M+3]+)

N-[(4-Bromo-1,3-thiazol-2-yl)methyl]cyclobutaneamine

1H NMR (200 MHz, CHLOROFORM-d) d ppm 1.51-2.44 (m, 6H), 3.27-3.68 (m, 1H), 4.02 (s, 2H), 7.14-7.22 (m, 1H)

(ESI pos.) m/z: 247([M+H]+), 249([M+3]+)

N-[(2-Bromopyridin-4-yl)methyl]-3,3-difluorocyclobutaneamine

1H NMR (600 MHz, CHLOROFORM-d) d ppm 2.27-2.37 (m, 2H), 2.76-2.87 (m, 2H), 3.21-3.30 (m, 1H), 3.73 (s, 2H), 7.20-7.24 (m, 1H), 7.50 (d, J=0.9 Hz, 1H), 8.31 (d, J=5.0 Hz, 1H)

(ESI pos.) m/z: 277([M+H]+), 279([M+3]+)

Production Example 6

N-(3-Bromo-4-fluorobenzyl)tetrahydro-2H-pyran-4-amine

[Chem 22]

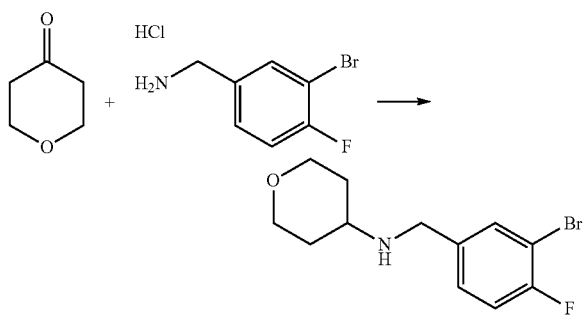

Triethylamine (2.52 g) was added to a suspension of 3-bromo-4-fluorobenzylamine hydrochloride (2.79 g) in chloroform (50 mL), and the mixture was stirred at room temperature for 10 min. Tetrahydro-4H-pyran-4-one (2.29 g) was added thereto and the mixture was stirred at room temperature for 30 min. Sodium triacetoxyborohydride (4.85 g) was added thereto, followed by further stirring for 1 hr. Saturated aqueous sodium hydrogen carbonate solution was added to the reaction mixture, and the resulting mixture was then stirred for a while and extracted with chloroform. The organic phase was separated out and the solvent was distilled off under reduced pressure. The resulting residue was purified by column chromatography (NH silica gel cartridge, hexane: ethyl acetate=100:0-90:10) to afford the title compound (2.70 g).

1H NMR (200 MHz, CHLOROFORM-d) d ppm 1.20-1.54 (m, 2H), 1.77-1.92 (m, 2H), 2.61-2.78 (m, 1H), 3.39 (td, J=11.6, 2.2 Hz, 2H), 3.78 (s, 2H), 3.91-4.04 (m, 2H), 7.01-7.12 (m, 1H), 7.18-7.29 (m, 1H), 7.55 (dd, J=6.6, 2.2 Hz, 1H)

Production Example 7

N-[(2-Bromopyridin-4-yl)methyl]-1-methyl-N-(propan-2-yl)-1H-imidazole-4-carboxamide

[Chem 23]

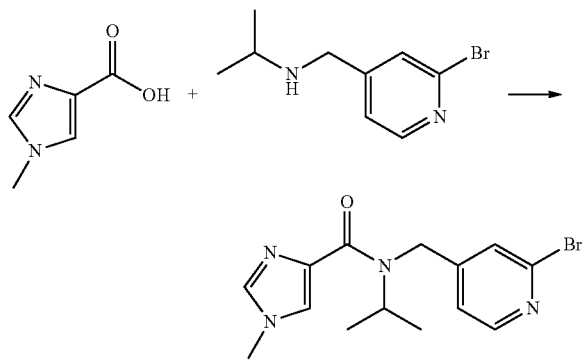

After a solution of methyl-1H-imidazole-4-carboxylic acid (1.45 g), 1-hydroxybenzotriazole hydrate (HOBT.H$_2$O) (2.08 g) and 1-(3-dimethylaminopropyl)-3-ethylcarbodiimide hydrochloride (EDC.HCl) (2.60 g) in acetonitrile (35 mL) was stirred at room temperature for 10 min, a solution of N-[(2-bromopyridin-4-yl)methyl]propan-2-amine (2.59 g) in acetonitrile (15 mL) was added thereto, and the resulting solution was then stirred at room temperature for 23 hr. The solvent was distilled off under reduced pressure, and the residue was then diluted with chloroform and washed with saturated aqueous sodium hydrogen carbonate solution. After extracting with chloroform, the solvent was distilled off under reduced pressure. The resulting residue was purified by column chromatography (silica gel cartridge, chloroform:methanol=98:2-82:18) and (the same column, chloroform:methanol=98:2-85:15) to afford the title compound (3.72 g).

1H NMR (600 MHz, CHLOROFORM-d) d ppm 1.10-1.24 (m, 6H), 3.57-3.80 (m, 3H), 4.45-5.91 (m, 3H), 7.12-7.62 (m, 4H), 8.20-8.27 (m, 1H)

(ESI pos.) m/z: 337([M+H]+), 339([M+3]+)

The following compounds were synthesized according to the similar procedure.

N-[(6-Bromopyridin-2-yl)methyl]-1-methyl-N-(propan-2-yl)-1H-imidazole-4-carboxamide 1H NMR (600 MHz, CHLOROFORM-d) d ppm 1.01-1.33 (m, 6H), 3.60-3.80 (m, 3H), 4.61-5.80 (m, 3H), 7.19-7.60 (m, 5H)

(ESI pos.) m/z: 337([M+H]+), 339([M+3]+)

N-[(6-Bromo-5-fluoropyridin-2-yl)methyl]-1-methyl-N-(propan-2-yl)-1H-imidazole-4-carboxamide 1H NMR (600 MHz, CHLOROFORM-d) d ppm 1.09-1.24 (m, 6H), 3.59-3.81 (m, 3H), 4.58-5.84 (m, 3H), 7.27 (s, 4H)

(ESI pos.) m/z: 355([M+H]+), 357([M+3]+)

N-[(6-Bromopyridin-2-yl)methyl]-1-methyl-N-propyl-1H-imidazole-4-carboxamide

1H NMR (600 MHz, CHLOROFORM-d) d ppm 0.83-0.93 (m, 3H), 1.61-1.71 (m, 2H), 3.34-4.05 (m, 5H), 4.72-5.51 (m, 2H), 7.29-8.11 (m, 5H)

(ESI pos.) m/z: 337([M+H]+), 339([M+3]+)

N-[(6-Bromopyridin-2-yl)methyl]-N-(2-methoxyethyl)-1-methyl-1H-imidazole-4-carboxamide 1H NMR (600 MHz, CHLOROFORM-d) d ppm 3.24-3.32 (m, 3H), 3.59-3.74 (m, 6H), 4.24-4.33 (m, 1H), 4.83-4.94 (m, 1H), 5.46-5.61 (m, 1H), 7.19-7.64 (m, 5H)

(ESI pos.) m/z: 353([M+H]+), 355([M+3]+)

N-[(2-Bromopyridin-4-yl)methyl]-1-methyl-N-propyl-1H-imidazole-4-carboxamide

1H NMR (600 MHz, CHLOROFORM-d) d ppm 0.84-0.97 (m, 3H), 1.59-1.73 (m, 2H), 3.29-4.04 (m, 5H), 4.60-4.73 (m, 1H), 5.30-5.50 (m, 1H), 7.12-7.64 (m, 4H), 8.28 (d, J=5.0 Hz, 1H)

(ESI pos.) m/z: 337([M+H]+), 339([M+3]+)

N-(3-Bromo-4-fluorobenzyl)-1-methyl-N-(propan-2-yl)-1H-imidazole-4-carboxamide

1H NMR1H NMR (200 MHz, CHLOROFORM-d) d ppm 1.05-1.30 (m, 6H), 3.71 (s, 3H), 4.44-5.90 (m, 3H), 6.93-7.63 (m, 5H)

(ESI pos.) m/z: 354([M+H]+), 356([M+3]+)

N-(3-Bromo-4-fluorobenzyl)-1-methyl-N-(tetrahydro-2H-pyran-4-yl)-1H-imidazole-4-carboxamide 1H NMR (600 MHz, CHLOROFORM-d) d ppm 1.50-1.89 (m, 4H), 3.35-3.55 (m, 2H), 3.72 (br. s., 3H), 3.89-4.07 (m, 2H), 4.53-5.70 (m, 3H), 6.95-7.69 (m, 5H) (ESI pos.) m/z: 396([M+H]+), 398([M+3]+)

Production Example 8

N-[(2-Bromopyridin-4-yl)methyl]-N-cyclobutyl-1-methyl-1H-imidazole-4-carboxamide

[Chem 24]

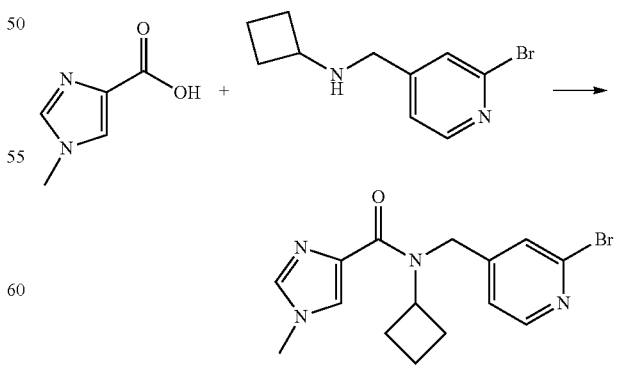

After a solution of methyl-1H-imidazole-4-carboxylic acid (300 mg), 2-(1H-7-azabenzotriazol-1-yl)-1,1,3,3-tetramethyl uronium hexafluorophosphate methanaminium (HATU) (1.27 g) and diisopropylethylamine (431 mg) in dimethylformamide (7 mL) was stirred at room temperature for 15 min, N-[(2-bromopyridin-4-yl)methyl]cyclobutanamine (574 mg) was added thereto and the mixture was stirred at room temperature overnight. The reaction mixture was diluted with chloroform, and washed with saturated aqueous sodium hydrogen carbonate solution. After extraction with chloroform, the organic phase was dried over anhydrous magnesium sulfate. After the desiccant was filtered off, the solvent was distilled off under reduced pressure. The resulting residue was purified by column chromatography (silica gel cartridge, hexane:ethyl acetate=80:20-50:50) to afford the title compound (1.46 g).

1H NMR (600 MHz, CHLOROFORM-d) d ppm 1.55-2.26 (m, 6H), 3.60-3.81 (m, 3H), 4.56-6.50 (m, 3H), 7.04-8.29 (m, 5H)

(ESI pos.) m/z: 349([M+H]+), 351([M+3]+)

The following compounds were synthesized according to the similar procedure.

N-[(2-Bromopyridin-4-yl)methyl]-1-methyl-N-(propan-2-yl)-1H-imidazole-4-carboxamide 1H NMR (600 MHz, CHLOROFORM-d) d ppm 1.10-1.28 (m, 6H), 3.62-3.79 (m, 3H), 4.49-5.88 (m, 3H), 7.12-7.61 (m, 4H), 8.20-8.28 (m, 1H)

(ESI pos.) m/z: 337([M+H]+), 339([M+3]+)

N-[(2-Bromopyridin-4-yl)methyl]-N-(propan-2-yl)-1H-imidazole-4-carboxamide

1H NMR (600 MHz, CHLOROFORM-d) d ppm 1.02-1.43 (m, 6H), 4.43-5.94 (m, 3H), 7.09-8.38 (m, 5H), 9.41-10.50 (m, 1H)

(ESI pos.) m/z: 323([M+H]+), 325([M+3]+)

N-[(2-Bromopyridin-4-yl)methyl]-1-methyl-N-(2-methylpropyl)-1H-imidazole-4-carboxamide 1H NMR (600 MHz, CHLOROFORM-d) d ppm 0.84-1.00 (m, 6H), 1.92-2.15 (m, 1H), 3.13-5.57 (m, 7H), 7.04-8.32 (m, 5H)

(ESI pos.) m/z: 351([M+H]+), 353([M+3]+)

N-[(2-Bromopyridin-4-yl)methyl]-N-(2-methoxyethyl)-1-methyl-1H-imidazole-4-carboxamide 1H NMR (600 MHz, CHLOROFORM-d) d ppm 3.21-3.36 (m, 3H), 3.54-3.83 (m, 6H), 4.21 (br. s., 1H), 4.80 (br. s., 1H), 5.54 (br. s., 1H), 7.12-7.65 (m, 4H), 8.27 (d, J=5.0 Hz, 1H)

(ESI pos.) m/z: 353([M+H]+), 355([M+3]+)

N-[(2-Bromopyridin-4-yl)methyl]-1-methyl-N-(3,3,3-trifluoropropyl)-1H-imidazole-4-carboxamide 1H NMR (600 MHz, CHLOROFORM-d) d ppm 2.43-2.75 (m, 2H), 3.51-3.83 (m, 4H), 4.11-4.28 (m, 1H), 4.60-4.74 (m, 1H), 5.37-5.53 (m, 1H), 7.11-8.08 (m, 4H), 8.31 (d, J=5.0 Hz, 1H)

(ESI pos.) m/z: 391([M+H]+), 393([M+3]+)

N-[(2-Bromopyridin-4-yl)methyl]-N-cyclobutyl-1H-1,2,4-triazole-3-carboxamide 1H NMR (600 MHz, CHLOROFORM-d) d ppm 1.45-2.34 (m, 6H), 4.78-6.10 (m, 3H), 7.06-8.24 (m, 3H), 8.30 (t, J=5.0 Hz, 1H)

(ESI pos.) m/z: 336([M+H]+), 338([M+3]+)

N-[(2-Bromopyridin-4-yl)methyl]-1-methyl-N-(tetrahydro-2H-pyran-4-yl)-1H-imidazole-4-carboxamide 1H NMR (600 MHz, CHLOROFORM-d) d ppm 1.58-1.95 (m, 4H), 3.43-3.51 (m, 2H), 3.66-3.78 (m, 3H), 3.93-4.00 (m, 2H), 4.55-6.35 (m, 3H), 7.12-8.27 (m, 5H)

(ESI pos.) m/z: 379([M+H]+), 381([M+3]+)

N-[(2-Bromopyridin-4-yl)methyl]-1-methyl-N-(tetrahydro-2H-pyran-4-ylmethyl)-1H-imidazole-4-carboxamide 1H NMR (600 MHz, CHLOROFORM-d) d ppm 1.16-2.15 (m, 5H), 3.11-6.22 (m, 11H), 7.02-8.35 (m, 5H)

(ESI pos.) m/z: 393([M+H]+), 395([M+3]+)

N-[(2-Bromo-1,3-thiazol-4-yl)methyl]-N-cyclobutyl-1-methyl-1H-imidazole-4-carboxamide 1H NMR (600 MHz, CHLOROFORM-d) d ppm 1.51-2.27 (m, 6H), 3.57-3.84 (m, 3H), 4.55-5.88 (m, 3H), 6.91-7.43 (m, 2H), 7.50 (s, 1H)

(ESI pos.) m/z: 355([M+H]+), 357([M+3]+)

N-[(2-Bromo-1,3-thiazol-4-yl)methyl]-N-(2-methoxyethyl)-1-methyl-1H-imidazole-4-carboxamide 1H NMR (600 MHz, CHLOROFORM-d) d ppm 3.24-3.82 (m, 9H), 4.30 (br. s., 1H), 4.86 (br. s., 1H), 5.52 (br. s., 1H), 7.14-7.19 (m, 1H), 7.31-7.38 (m, 1H), 7.56-7.58 (m, 1H) (ESI pos.) m/z: 359([M+H]+), 361([M+3]+)

N-[(2-Bromo-1,3-thiazol-4-yl)methyl]-1-methyl-N-(tetrahydro-2H-pyran-4-yl)-1H-imidazole-4-carboxamide 1H NMR (200 MHz, CHLOROFORM-d) d ppm 1.49-1.98 (m, 4H), 3.37-3.56 (m, 2H), 3.71 (s, 3H), 3.99 (dd, J=10.8, 4.6 Hz, 2H), 4.48-5.71 (m, 3H), 7.05-7.42 (m, 2H), 7.55 (d, J=1.3 Hz, 1H)

(ESI pos.) m/z: 385([M+H]+), 387([M+3]+)

N-[(4-Bromo-1,3-thiazol-2-yl)methyl]-1-methyl-N-(tetrahydro-2H-pyran-4-yl)-1H-imidazole-4-carboxamide 1H NMR (200 MHz, CHLOROFORM-d) d ppm 1.55-2.09 (m, 4H), 3.34-3.56 (m, 2H), 3.73 (s, 3H), 4.00 (dd, J=11.4, 4.4 Hz, 2H), 4.76-6.20 (m, 3H), 7.14 (s, 1H), 7.32-7.39 (m, 1H), 7.59-7.64 (m, 1H)

(ESI pos.) m/z: 385([M+H]+), 387([M+3]+)

N-(3-Bromo-4-fluorobenzyl)-1-methyl-N-(propan-2-yl)-1H-imidazole-4-carboxamide 1H NMR (600 MHz, CHLOROFORM-d) d ppm 1.02-1.33 (m, 6H), 3.71 (br. s., 3H), 4.46-5.84 (m, 3H), 6.94-7.61 (m, 5H)

N-(3-Bromo-4-fluorobenzyl)-N-(propan-2-yl)-1H-imidazole-4-carboxamide

1H NMR (600 MHz, CHLOROFORM-d) d ppm 1.04-1.35 (m, 6H), 4.51-5.20 (m, 3H), 6.98-7.71 (m, 5H)

(ESI pos.) m/z: 340([M+H]+), 342([M+3]+)

N-(3-Bromo-4-fluorobenzyl)-N-cyclobutyl-1-methyl-1H-imidazole-4-carboxamide

1H NMR (600 MHz, CHLOROFORM-d) d ppm 1.50-1.74 (m, 2H), 1.99-2.22 (m, 4H), 3.57-3.80 (m, 3H), 4.43-5.80 (m, 3H), 6.98-8.04 (m, 5H)

(ESI pos.) m/z: 366([M+H]+), 368([M+3]+)

N-(3-Bromo-4-fluorobenzyl)-1-methyl-N-(tetrahydro-2H-pyran-4-yl)-1H-imidazole-4-carboxamide 1H NMR (600 MHz, CHLOROFORM-d) d ppm 1.49-1.98 (m, 4H), 3.36-3.52 (m, 2H), 3.64-3.80 (m, 3H), 3.90-4.03 (m, 2H), 4.54-5.66 (m, 3H), 6.94-7.64 (m, 5H)

(ESI pos.) m/z: 396([M+H]+), 398([M+3]+)

N-(3-Bromo-4-fluorobenzyl)-N-(tetrahydro-2H-pyran-4-yl)-1H-1,2,4-triazole-3-carboxamide 1H NMR (600 MHz, CHLOROFORM-d) d ppm 1.58-1.89 (m, 4H), 3.41-3.52 (m, 2H), 3.95-4.04 (m, 2H), 4.61-5.71 (m, 3H), 7.04-8.18 (m, 4H)

N-[(4-Bromo-1,3-thiazol-2-yl)methyl]-N-cyclobutyl-1-methyl-1H-imidazole-4-carboxamide 1H NMR (600 MHz, CHLOROFORM-d) d ppm 1.58-1.76 (m, 2H), 1.97-2.38 (m, 4H), 3.71 (s, 3H), 4.58-5.95 (m, 3H), 7.13 (s, 1H), 7.37 (br. s., 1H), 7.57 (s, 1H)

(ESI pos.) m/z: 355([M+H]+), 357([M+3]+)

N-[(2-Bromopyridin-4-yl)methyl]-N-(3,3-difluorocyclobutyl)-1-methyl-1H-imidazole-4-carboxamide 1H NMR (600 MHz, CHLOROFORM-d) d ppm 2.36-3.09 (m, 4H), 3.72 (s, 3H), 4.61-5.72 (m, 3H), 7.00-8.37 (m, 5H)

(ESI pos.) m/z: 385([M+H]+), 387([M+3]+)

Production Example 9

N-(3-Bromo-4-fluorobenzyl)-N-cyclobutyl-1-methyl-1H-imidazole-4-carboxamide

[Chem 25]

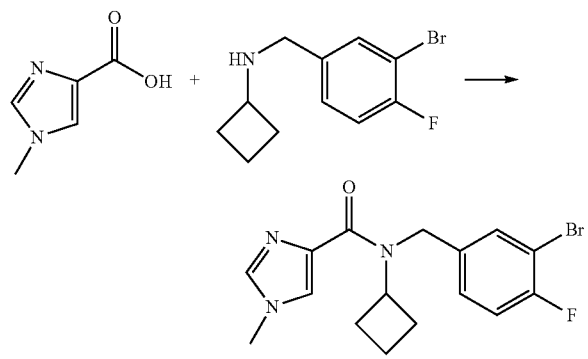

A solution of methyl-1H-imidazole-4-carboxylic acid (1.17 g), N-(3-bromo-4-fluorobenzyl)cyclobutanamine (2.40 g) and 4-(4,6-dimethoxy-1,3,5-triazin-2-yl)-4-methylmorpholinium chloride (DMT-MM) (3.09 g) in methanol (25 mL) was stirred at room temperature for 4 hr. After the reaction mixture was concentrated under reduced pressure, the resulting residue was diluted with chloroform and washed with saturated aqueous sodium hydrogen carbonate solution. After extraction with chloroform, the organic phase was dried over anhydrous magnesium sulfate. The desiccant was filtered off and the solvent was then distilled off under reduced pressure. The resulting residue was purified by column chromatography (silica gel cartridge, chloroform:methanol=98:2-92:8) to afford the title compound (469 mg).

1H NMR (600 MHz, CHLOROFORM-d) d ppm 1.50-1.76 (m, 2H), 1.98-2.26 (m, 4H), 3.65-3.80 (m, 3H), 4.47-5.94 (m, 3H), 6.93-7.56 (m, 5H)

(ESI pos.) m/z: 366([M+H]+), 368([M+3]+)

The following compounds were synthesized according to the similar procedure.

N-[(2-Bromopyridin-4-yl)methyl]-N-(propan-2-yl)-1H-imidazole-4-carboxamide

1H NMR (600 MHz, CHLOROFORM-d) d ppm 1.01-1.51 (m, 6H), 4.46-5.92 (m, 3H), 7.08-8.43 (m, 5H), 9.66-10.46 (m, 1H)

(ESI pos.) m/z: 323([M+H]+), 235([M+3]+)

N-[(2-Bromopyridin-4-yl)methyl]-1-methyl-N-(pentan-3-yl)-1H-imidazole-4-carboxamide 1H NMR (200 MHz, CHLOROFORM-d) d ppm 0.71-0.99 (m, 6H), 1.30-1.71 (m, 4H), 3.65-3.81 (m, 3H), 4.37-5.67 (m, 3H), 7.07-8.34 (m, 5H)

(ESI pos.) m/z: 365([M+H]+), 367([M+3]+)

N-[(2-Bromopyridin-4-yl)methyl]-N-cyclopentyl-1-methyl-1H-imidazole-4-carboxamide 1H NMR (600 MHz, CHLOROFORM-d) d ppm 1.29-2.05 (m, 8H), 3.60-3.84 (m, 3H), 4.43-5.93 (m, 3H), 7.11-7.62 (m, 4H), 8.16-8.34 (m, 1H) (ESI pos.) m/z: 363([M+H]+), 365([M+3]+)

N-[(2-Bromopyridin-4-yl)methyl]-N-cyclohexyl-1-methyl-1H-imidazole-4-carboxamide 1H NMR (200 MHz, CHLOROFORM-d) d ppm 0.96-1.98 (m, 10H), 3.64-3.77 (m, 3H), 4.43-5.44 (m, 3H), 7.06-8.36 (m, 5H)

(ESI pos.) m/z: 377([M+H]+), 379([M+3]+)

N-[(2-Bromopyridin-4-yl)methyl]-N-(cyclopropylmethyl)-1-methyl-1H-imidazole-4-carboxamide 1H NMR (600 MHz, CHLOROFORM-d) d ppm 0.13-0.28 (m, 2H), 0.42-0.57 (m, 2H), 0.93-1.13 (m, 1H), 3.35 (br. s., 1H), 3.64-3.80 (m, 3H), 3.92-4.04 (m, 1H), 4.81 (br. s., 1H), 5.53 (br. s., 1H), 7.11-7.68 (m, 4H), 8.21-8.36 (m, 1H)

(ESI pos.) m/z: 349([M+H]+), 351([M+3]+)

Production Example 10

N-[4-Fluoro-3-(4,4,5,5-tetramethyl-1,3,2-dioxaborolan-2-yl)benzyl]-1-methyl-N-(propan-2-yl)-1H-imidazole-4-carboxamide

[Chem 26]

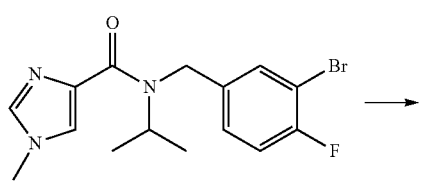

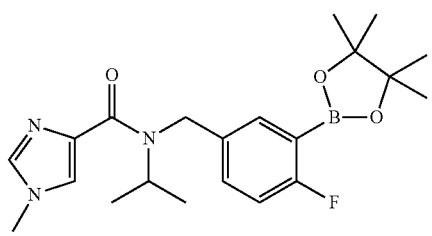

A solution of N-(3-bromo-4-fluorobenzyl)-1-methyl-N-(propan-2-yl)-1H-imidazole-4-carboxamide (5.0 g), bis(pinacolate)diborane (4.3 g), [1,1'-bis(diphenylphosphino)ferrocene]dichloropalladium(II) (1.15 g) and potassium acetate (4.16 g) in dimethylsulfoxide (20 mL) was stirred while heating at 100° C. for 5 hr. The reaction mixture was filtered through Celite, then washed with water and extracted with ethyl acetate. The organic phase was separated out and the solvent was distilled off under reduced pressure. The resulting residue was purified by column chromatography (silica gel cartridge, chloroform:methanol=98:2-80:20) to afford the title compound (3.0 g).

(ESI pos.) m/z: 402([M+H]+)

The following compounds were synthesized according to the similar procedure. N-Cyclobutyl-N-[4-fluoro-3-(4,4,5,5-tetramethyl-1,3,2-dioxaborolan-2-yl)benzyl]-1-methyl-1H-imidazole-4-carboxamide 1H NMR (600 MHz, CHLOROFORM-d) d ppm 1.22-1.24 (m, 12H), 1.49-2.22 (m, 6H), 3.61-3.77 (m, 3H), 4.44-5.87 (m, 3H), 6.87-7.63 (m, 5H)

(ESI pos.) m/z: 414([M+H]+)

N-[4-Fluoro-3-(4,4,5,5-tetramethyl-1,3,2-dioxaborolan-2-yl)benzyl]-1-methyl-N-(tetrahydro-2H-pyran-4-yl)-1H-imidazole-4-carboxamide 1H NMR (600 MHz, CHLOROFORM-d) d ppm 1.21-1.26 (m, 12H), 1.47-2.15 (m, 4H), 3.33-3.50 (m, 2H), 3.62-3.80 (m, 3H), 3.94 (dd, J=11.2, 3.9 Hz, 2H), 4.60-5.63 (m, 3H), 6.87-7.66 (m, 5H)

(ESI pos.) m/z: 444([M+H]+)

Production Example 11

N-[(2-Bromopyridin-4-yl)methyl]-N-cyclobutyl-1-methyl-1H-1,2,4-triazole-3-carboxamide

[Chem 27]

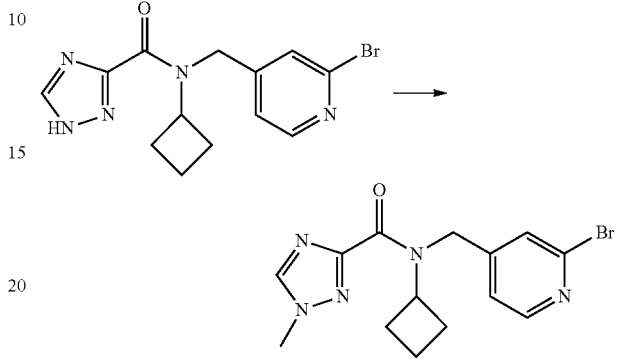

Sodium hydride (186 mg) was added to a solution of N-[(2-bromopyridin-4-yl)methyl]-N-cyclobutyl-1H-1,2,4-triazole-3-carboxamide (1.3 g) in dimethylformamide (10 mL), and the mixture was stirred at room temperature for 15 min. Methyl iodide (0.25 mL) was added thereto and the mixture was stirred at room temperature for 17.5 hr. Saturated aqueous sodium hydrogen carbonate solution and water were added to the reaction mixture, followed by extraction with ethyl acetate, and the solvent was distilled off under reduced pressure. The resulting residue was purified by column chromatography (NH silica gel cartridge, hexane:ethyl acetate=75:25-0:100) to afford the title compound (748 mg).

1H NMR (600 MHz, CHLOROFORM-d) d ppm 1.43-1.80 (m, 2H), 1.94-2.29 (m, 4H), 3.81-4.08 (m, 3H), 4.73-5.12 (m, 3H), 7.06-8.35 (m, 4H)

(ESI pos.) m/z: 350([M+H]+), 352([M+3]+)

The following compound was synthesized according to the similar procedure.

N-(3-Bromo-4-fluorobenzyl)-1-methyl-N-(tetrahydro-2H-pyran-4-yl)-1H-1,2,4-triazole-3-carboxamide 1H NMR (600 MHz, CHLOROFORM-d) d ppm 1.59-1.86 (m, 4H), 3.21-4.91 (m, 10H), 7.01-8.13 (m, 4H)

(ESI pos.) m/z: 397([M+H]+), 399([M+3]+)

Production Example 12

N-{[2-(4-Fluorophenyl)pyridin-4-yl]methyl}propan-2-amine

[Chem 28]

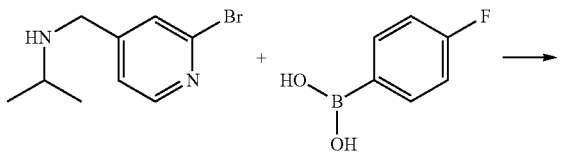

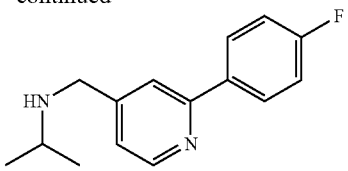

A mixture of N-[(2-bromopyridin-4-yl)methyl]propan-2-amine (2.00 g), 4-fluorophenylboronic acid (1.34 g), cesium carbonate (4.26 g), tetrakis(triphenylphosphine)palladium (1.01 g), toluene (4.5 mL), ethanol (4.5 mL) and water (3.0 mL) was stirred under irradiation with microwave while heating at 150° C. for 30 min. Saturated aqueous sodium hydrogen carbonate solution and ethyl acetate were added to the reaction mixture, and the resulting mixture was then filtered through Celite and extracted with ethyl acetate. The whole organic phase was collected and dried over magnesium sulfate. After the desiccant was filtered off, the solution was concentrated under reduced pressure. The resulting residue was purified by column chromatography (silica gel cartridge, chloroform:methanol=96:4-92:8) and (NH silica gel cartridge, hexane:ethyl acetate=90:10-60:40) to afford the title compound (1.13 g).

1H NMR (600 MHz, CHLOROFORM-d) d ppm 1.05-1.19 (m, 6H), 2.81-2.94 (m, 1H), 3.86 (s, 2H), 7.12-7.22 (m, 3H), 7.67 (s, 1H), 7.93-8.03 (m, 2H), 8.59 (d, J=5.0 Hz, 1H)

(ESI pos.) m/z: 245([M+H]+)

Production Example 13

1,1,1-Trifluoro-N-{[2-(4-fluorophenyl)pyridin-4-yl]methyl}propan-2-amine

[Chem 29]

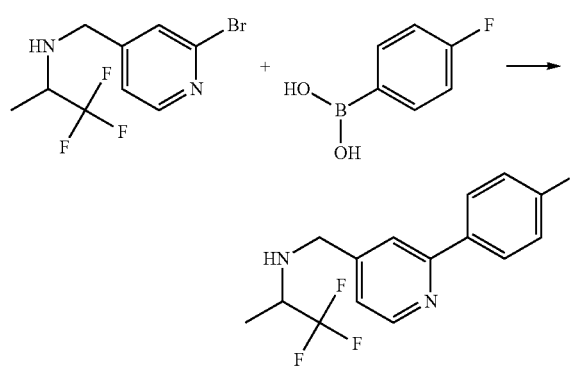

A mixture of N-[(2-bromopyridin-4-yl)methyl]-1,1,1-trifluoropropan-2-amine (150 mg), 4-fluorophenylboronic acid (111 mg), cesium carbonate (345 mg), tetrakis(triphenylphosphine)palladium (61 mg), toluene (0.6 mL), ethanol (0.6 mL) and water (4.0 mL) was stirred while heating at 100° C. for 3 hr. The supernatant of the reaction mixture was purified by column chromatography (silica gel cartridge, hexane:ethyl acetate=95:5-60:40) to afford the title compound (143 mg).

1H NMR (600 MHz, CHLOROFORM-d) d ppm 1.29-1.32 (m, 3H), 1.51 (br. s., 1H), 3.17-3.25 (m, 1H), 3.97-4.05 (m, 2H), 7.11-7.24 (m, 3H), 7.69 (s, 1H), 7.95-8.02 (m, 2H), 8.61 (d, J=5.0 Hz, 1H)

(ESI pos.) m/z: 299([M+H]+)

Production Example 14

{1-[4-(Trifluoromethoxy)phenyl]-1H-pyrazol-4-yl}methanol

[Chem 30]

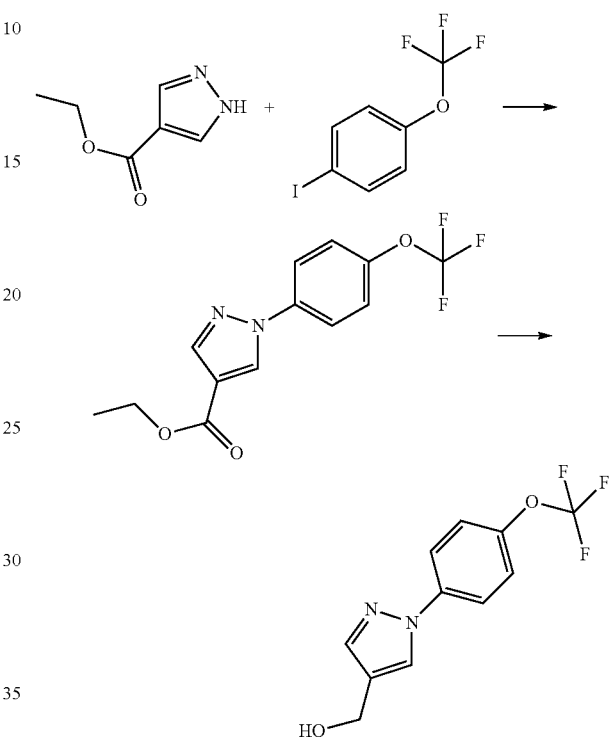

(1) A solution of ethyl 4-pyrazolecarboxylate (500 mg), 4-(trifluoromethoxy)iodobenzene (1.00 g), trans-1,2-bis(methylamino)cyclohexane (100 mg), copper iodide (70 mg) and cesium carbonate (1.7 g) in dioxane (5.0 mL) was stirred while heating at 100° C. for 5 hr. The reaction mixture was filtered through Celite and the solvent was then distilled off under reduced pressure. The resulting residue was purified by column chromatography (silica gel cartridge, hexane:ethyl acetate=98:2-80:20) to afford ethyl 1-[4-(trifluoromethoxy)phenyl]-1H-pyrazole-4-carboxylate (100 mg).

1H NMR (600 MHz, CHLOROFORM-d) d ppm 1.38 (t, J=7.1 Hz, 3H), 4.35 (q, J=7.0 Hz, 2H), 7.32-7.37 (m, 2H), 7.73-7.78 (m, 2H), 8.10 (s, 1H), 8.39 (s, 1H)

(ESI pos.) m/z: 301([M+H]+)

The following compound was synthesized according to the similar procedure.

Ethyl 1-[3-(trifluoromethoxy)phenyl]-1H-pyrazole-4-carboxylate

1H NMR (200 MHz, CHLOROFORM-d) d ppm 1.34-1.43 (m, 3H), 4.35 (q, J=7.3 Hz, 2H), 7.13-7.73 (m, 4H), 8.11 (s, 1H), 8.42 (s, 1H)

(ESI pos.) m/z: 301([M+H]+)

(2) Diisobutylaluminum hydride (0.99 M solution in hexane) (0.7 mL) was added to an ice-cold solution of ethyl 1-[4-(trifluoromethoxy)phenyl]-1H-pyrazole-4-carboxylate (100 mg) in tetrahydrofuran (5.0 mL), and the mixture was stirred at room temperature for 1 hr. Additional diisobutylaluminum hydride (0.99 M solution in hexane) (0.7 mL) was added, and the mixture was further stirred at room temperature for 1 hr. An aqueous potassium sodium tartrate solution was added to the reaction mixture, and the mixture was then stirred at room temperature for 10 hr and extracted with chloroform, and the solvent was distilled off under reduced pressure. The resulting residue was purified by PTLC (silica gel, ethyl acetate) to afford the title compound (50 mg).

(ESI pos.) m/z: 259([M+H]+)

The following compound was synthesized according to the similar procedure.

{1-[3-(Trifluoromethoxy)phenyl]-1H-pyrazol-4-yl}methanol

1H NMR (200 MHz, CHLOROFORM-d) d ppm 4.58-4.79 (m, 2H), 7.09-7.64 (m, 4H), 7.73 (s, 1H), 7.91-7.97 (m, 1H)
(ESI pos.) m/z: 259([M+H]+)

Production Example 15

{2-[4-(Trifluoromethoxy)phenyl]-1,3-thiazol-4-yl}methanol

[Chem 31]

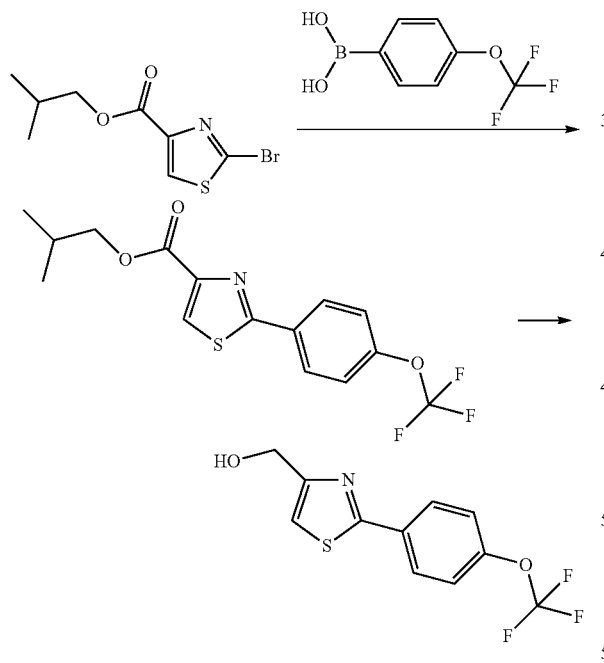

(1) According to the similar procedure as in Production Example 13, 2-methylpropyl 2-[4-(trifluoromethoxy)phenyl]-1,3-thiazole-4-carboxylate (881 mg) was obtained from 2-methylpropyl 2-bromo-1,3-thiazole-4-carboxylate (935 mg) and 4-trifluoromethoxyphenylboronic acid (960 mg).

1H NMR (200 MHz, CHLOROFORM-d) d ppm 1.02 (s, 3H), 1.05 (s, 3H), 2.01-2.23 (m, 1H), 4.10-4.24 (m, 2H), 7.21-7.38 (m, 2H), 7.98-8.20 (m, 3H)
(ESI pos.) m/z: 346([M+H]+)

The following compound was synthesized according to the similar procedure.

Ethyl 2-[4-(trifluoromethoxy)phenyl]-1,3-thiazole-5-carboxylate

1H NMR (600 MHz, CHLOROFORM-d) d ppm 1.41 (t, J=7.1 Hz, 3H), 4.40 (q, J=6.9 Hz, 2H), 7.29-7.34 (m, 2H), 7.98-8.08 (m, 2H), 8.42 (s, 1H)
(ESI pos.) m/z: 318([M+H]+)

(2) Lithium aluminum hidride (2.0 M solution in tetrahydrofuran) (2.81 mL) was added to a solution of 2-methylpropyl 2-[4-(trifluoromethoxy)phenyl]-1,3-thiazole-4-carboxylate (881 mg) in tetrahydrofuran (15 mL), and the mixture was stirred at room temperature for 30 min. Sodium sulfate decahydrate was added portionwise and an additional amount of tetrahydrofuran was added, and the mixture was stirred for 1.5 hr. The reaction mixture was filtered through Celite and the solvent was then distilled off under reduced pressure. The resulting residue was purified by column chromatography (NH silica gel cartridge, hexane:ethyl acetate=98:2-25:75) to afford the title compound (361 mg).

1H NMR (200 MHz, CHLOROFORM-d) d ppm 4.83 (s, 2H), 7.09-7.40 (m, 3H), 7.89-8.06 (m, 2H)
(ESI pos.) m/z: 276([M+H]+)

The following compound was synthesized according to the similar procedure.

{2-[4-(Trifluoromethoxy)phenyl]-1,3-thiazol-5-yl}methanol

1H NMR (200 MHz, CHLOROFORM-d) d ppm 1.88-2.02 (m, 1H), 4.92 (d, J=5.3 Hz, 2H), 7.16-7.39 (m, 2H), 7.73 (s, 1H), 7.89-8.04 (m, 2H)
(ESI pos.) m/z: 276([M+H]+)

Production Example 16

{2-[4-(Trifluoromethoxy)phenyl]pyrimidin-4-yl}methanol

[Chem 32]

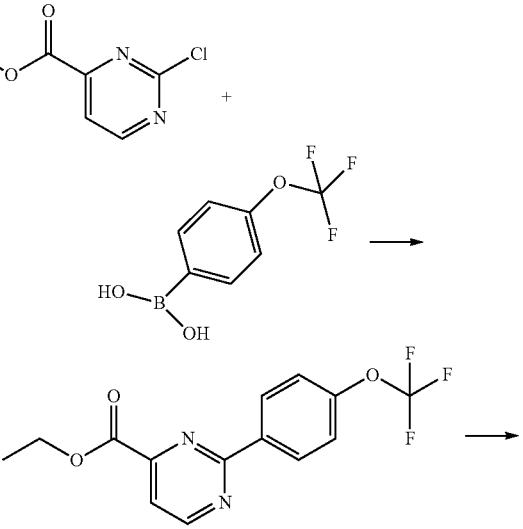

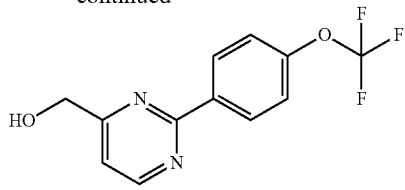

(1) According to the similar procedure as in Production Example 13, ethyl 2-[4-(trifluoromethoxy)phenyl]pyrimidine-4-carboxylate (29 mg) was obtained from methyl 2-chloro-6-methylpyrimidine-4-carboxylate (100 mg) and 4-trifluoromethoxyphenylboronic acid (131 mg).

1H NMR (600 MHz, CHLOROFORM-d) d ppm 1.48 (t, J=7.1 Hz, 3H), 4.52 (q, J=6.9 Hz, 2H), 7.30-7.36 (m, 2H), 7.86 (d, J=5.0 Hz, 1H), 8.55-8.60 (m, 2H), 9.02 (d, J=5.0 Hz, 1H)

(ESI pos.) m/z: 313([M+H]+)

(2) After lithium borohydride (3.0 M solution in tetrahydrofuran) (0.05 mL) and methanol (0.006 mL) was added dropwise to an ice-cold solution of ethyl 2-[4-(trifluoromethoxy)phenyl]pyrimidine-4-carboxylate (29 mg) in tetrahydrofuran (3.0 mL), the mixture was stirred for 1 hr, then returned to room temperature and stirred for 30 min. After the solvent was distilled off under reduced pressure, the residue was dissolved in ethyl acetate. After washing with 2N hydrochloric acid, saturated sodium hydrogen carbonate solution and brine, the organic phase was separated out. The solvent was distilled off under reduced pressure to afford the title compound (13 mg) as the residue.

1H NMR (600 MHz, CHLOROFORM-d) d ppm 3.34-3.44 (m, 1H), 4.83 (d, J=5.0 Hz, 2H), 7.18-7.37 (m, 3H), 8.47-8.54 (m, 2H), 8.77 (d, J=5.0 Hz, 1H)

(ESI pos.) m/z: 271([M+H]+)

Production Example 17

{3-[4-(Trifluoromethoxy)phenyl]-1,2-oxazol-5-yl}methanol

[Chem 33]

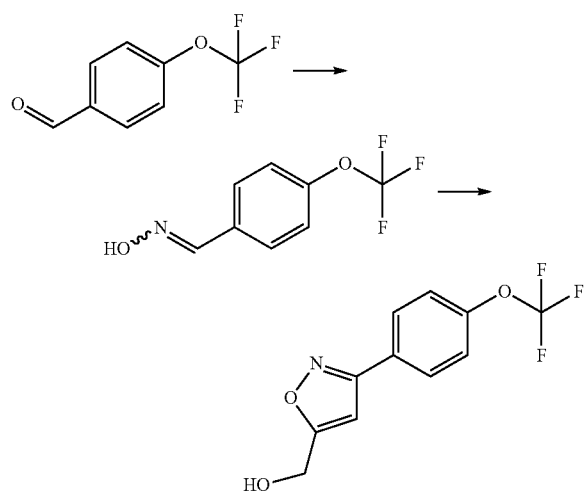

(1) A mixture of 4-(trifluoromethoxy)benzaldehyde (2.00 g), 50% hydroxylamine (4.0 mL) and ethanol (25 mL) was heated to reflux for 3 hr. The solvent was distilled off under reduced pressure to afford N-hydroxy-1-[4-(trifluoromethoxy)phenyl]methaneimine (2.5 g) as the residue.

1H NMR (200 MHz, CHLOROFORM-d) d ppm 7.13-7.33 (m, 2H), 7.56-7.65 (m, 2H), 8.13 (s, 1H)

The following compound was synthesized according to the similar procedure.

N-Hydroxy-1-{4-[(trifluoromethyl)sulfanyl]phenyl}methaneimine

1H NMR (200 MHz, CHLOROFORM-d) d ppm 7.58-7.74 (m, 4H), 8.15 (s, 1H)

(2) N-Chlorosuccinimide (1.5 g) was added to a solution of N-hydroxy-1-[4-(trifluoromethoxy)phenyl]methaneimine (2.5 g) in chloroform (50 mL) and the mixture was stirred at room temperature for 1 hr. Propargylalcohol (0.8 mL) was added thereto, triethylamine (1.8 mL) was then added slowly, and the mixture was stirred at room temperature overnight. The solvent was distilled off under reduced pressure, and the resulting residue was then purified by column chromatography (silica gel cartridge, hexane:ethyl acetate=94:6-50:50) to afford the title compound (1.3 g).

1H NMR (200 MHz, CHLOROFORM-d) d ppm 4.81-4.88 (m, 2H), 6.54-6.58 (m, 1H), 7.27-7.37 (m, 2H), 7.79-7.89 (m, 2H)

The following compounds were synthesized according to the similar procedure.

(3-{4-[(Trifluoromethyl)sulfanyl]phenyl}-1,2-oxazol-5-yl)methanol

1H NMR (200 MHz, CHLOROFORM-d) d ppm 4.86 (s, 2H), 6.60 (t, J=0.9 Hz, 1H), 7.70-7.90 (m, 4H)

(ESI pos.) m/z: 276([M+H]+)

(3-Phenyl-1,2-oxazol-5-yl)methanol

1H NMR (200 MHz, CHLOROFORM-d) d ppm 4.82 (s, 2H), 6.51-6.62 (m, 1H), 7.29-7.98 (m, 5H)

(ESI pos.) m/z: 176([M+H]+)

Production Example 18

2-[4-(Trifluoromethoxy)phenyl]-1,3-thiazole-4-carbaldehyde

[Chem 34]

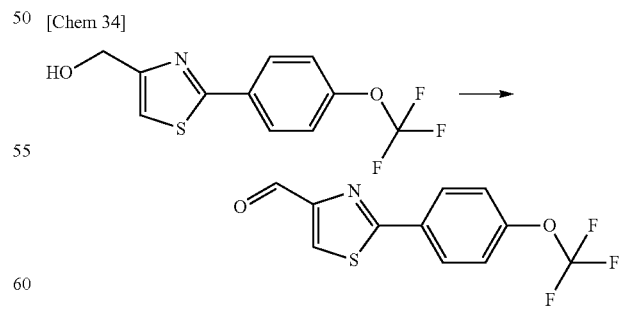

A solution of 2-iodoxybenzoic acid (441 mg) in dimethylsulfoxide (5 mL) was added to a solution of {2-[4-(trifluoromethoxy)phenyl]-1,3-thiazol-4-yl}methanol (361 mg) in dimethylsulfoxide (10 mL) and the resulting mixture was stirred at room temperature overnight. After water was added, the mixture was filtered through Celite and then extracted with ethyl acetate. The solvent was distilled off under reduced pressure to afford the title compound (358 mg) as the residue.

1H NMR (200 MHz, CHLOROFORM-d) d ppm 7.29-7.38 (m, 2H), 8.00-8.21 (m, 3H), 10.10 (s, 1H)

(ESI pos.) m/z: 274([M+H]+)

The following compounds were synthesized according to the similar procedure.

2-[4-(Trifluoromethoxy)phenyl]-1,3-thiazole-5-carbaldehyde

1H NMR (200 MHz, CHLOROFORM-d) d ppm 7.29-7.43 (m, 2H), 8.01-8.14 (m, 2H), 8.45 (s, 1H), 10.06 (s, 1H)

(ESI pos.) m/z: 274([M+H]+)

3-[4-(Trifluoromethoxy)phenyl]-1,2-oxazole-5-carbaldehyde

1H NMR (200 MHz, CHLOROFORM-d) d ppm 7.28 (s, 1H), 7.30-7.41 (m, 2H), 7.84-7.96 (m, 2H), 10.04 (s, 1H)

3-{4-[(Trifluoromethyl)sulfanyl]phenyl}-1,2-oxazole-5-carbaldehyde

1H NMR (200 MHz, CHLOROFORM-d) d ppm 7.31 (s, 1H), 7.71-7.96 (m, 4H), 10.05 (s, 1H)

3-Phenyl-1,2-oxazole-5-carbaldehyde

1H NMR (200 MHz, CHLOROFORM-d) d ppm 7.29 (s, 1H), 7.38-7.60 (m, 3H), 7.76-7.95 (m, 2H), 10.04 (s, 1H)

1-[4-(Trifluoromethoxy)phenyl]-1H-pyrazole-4-carbaldehyde

1-[3-(Trifluoromethoxy)phenyl]-1H-pyrazole-4-carbaldehyde

5-(4-Chlorophenyl)-1,2,4-oxadiazole-3-carbaldehyde

1H NMR (200 MHz, CHLOROFORM-d) d ppm 7.36-8.23 (m, 4H), 10.20 (s, 1H)

2-[4-(Trifluoromethoxy)phenyl]pyrimidine-4-carbaldehyde

1H NMR (600 MHz, CHLOROFORM-d) d ppm 7.33-7.40 (m, 2H), 7.71 (d, J=4.6 Hz, 1H), 8.57-8.63 (m, 2H), 9.07 (d, J=4.6 Hz, 1H), 10.13 (s, 1H)

Production Example 19

N-({2-[4-(Trifluoromethoxy)phenyl]-1,3-thiazol-4-yl}methyl)cyclobutaneamine

[Chem 35]

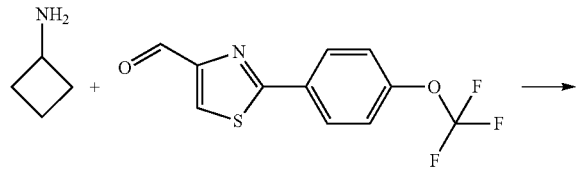

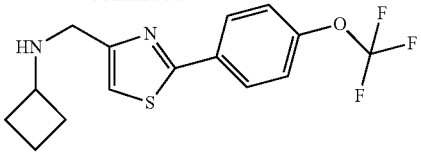

According to the similar procedure as in Production Example 5, the title compound (430 mg) was obtained from 2-[4-(trifluoromethoxy)phenyl]-1,3-thiazole-4-carbaldehyde (358 mg).

1H NMR (600 MHz, CHLOROFORM-d) d ppm 1.58-2.30 (m, 6H), 3.28-3.43 (m, 1H), 3.88 (s, 2H), 7.11 (s, 1H), 7.25-7.30 (m, 2H), 7.95-8.01 (m, 2H)

(ESI pos.) m/z: 329([M+H]+)

The following compounds were synthesized according to the similar procedure.

N-({2-[4-(Trifluoromethoxy)phenyl]-1,3-thiazol-5-yl}methyl)cyclobutaneamine

1H NMR (200 MHz, CHLOROFORM-d) d ppm 1.57-2.33 (m, 6H), 3.31-3.49 (m, 1H), 3.86-4.08 (m, 2H), 7.22-7.34 (m, 2H), 7.68 (s, 1H), 7.87-8.01 (m, 2H)

(ESI pos.) m/z: 329([M+H]+)

N-({3-[4-(Trifluoromethoxy)phenyl]-1,2-oxazol-5-yl}methyl)cyclobutaneamine

1H NMR (200 MHz, CHLOROFORM-d) d ppm 1.53-1.92 (m, 4H), 2.12-2.43 (m, 2H), 3.25-3.39 (m, 1H), 3.85-3.93 (m, 2H), 6.42-6.49 (m, 1H), 7.25-7.37 (m, 2H), 7.77-7.90 (m, 2H)

(ESI pos.) m/z: 313([M+H]+)

N-[(3-{4-[(Trifluoromethyl)sulfanyl]phenyl}-1,2-oxazol-5-yl)methyl]cyclobutaneamine 1H NMR (600 MHz, CHLOROFORM-d) d ppm 1.54-1.78 (m, 4H), 2.19-2.27 (m, 2H), 3.32-3.41 (m, 1H), 3.91 (s, 2H), 6.49 (s, 1H), 7.74 (d, J=8.3 Hz, 2H), 7.83-7.88 (m, 2H)

(ESI pos.) m/z: 329([M+H]+)

N-[(3-Phenyl-1,2-oxazol-5-yl)methyl]cyclohexaneamine

1H NMR (200 MHz, CHLOROFORM-d) d ppm 1.00-1.99 (m, 10H), 2.44-2.61 (m, 1H), 4.00 (s, 2H), 6.47 (s, 1H), 7.40-7.49 (m, 3H), 7.75-7.85 (m, 2H)

(ESI pos.) m/z: 257([M+H]+)

N-({1-[4-(Trifluoromethoxy)phenyl]-1H-pyrazol-4-yl}methyl)cyclobutaneamine

1H NMR (600 MHz, CHLOROFORM-d) d ppm 1.61-1.79 (m, 4H), 2.21-2.30 (m, 2H), 3.32-3.39 (m, 1H), 3.68 (s, 2H), 7.27-7.32 (m, 2H), 7.64-7.72 (m, 3H), 7.86 (s, 1H)

(ESI pos.) m/z: 312([M+H]+)

N-({1-[3-(Trifluoromethoxy)phenyl]-1H-pyrazol-4-yl}methyl)cyclobutaneamine

N-{[5-(4-Chlorophenyl)-1,2,4-oxadiazol-3-yl]methyl}propan-2-amine

1H NMR (200 MHz, CHLOROFORM-d) d ppm 1.11 (s, 3H), 1.14 (s, 3H), 2.82-2.97 (m, 1H), 3.99 (s, 2H), 7.47-7.55 (m, 2H), 8.04-8.12 (m, 2H)

(ESI pos.) m/z: 252([M+H]+)

N-({2-[4-(Trifluoromethoxy)phenyl]pyrimidin-4-yl}methyl)cyclobutaneamine

Production Example 20

N-[(4-Phenylpyridin-2-yl)methyl]propan-1-amine

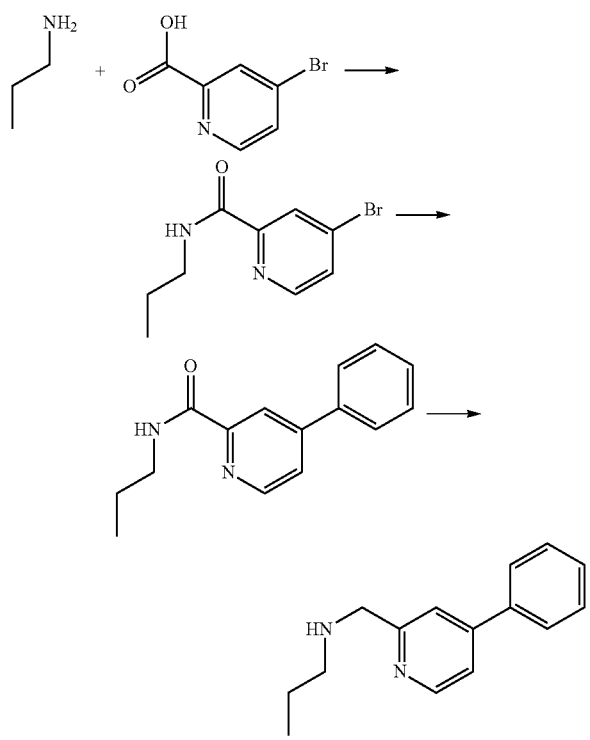

[Chem 36]

(1) According to the similar procedure as in Production Example 7, 4-bromo-N-propylpyridine-2-carboxamide (509 mg) was obtained from 4-bromopyridine-2-carboxylic acid (500 mg) and n-propylamine (0.25 mL).

1H NMR (600 MHz, CHLOROFORM-d) d ppm 0.97-1.02 (m, 3H), 1.62-1.70 (m, 2H), 3.41-3.46 (m, 2H), 7.57-7.61 (m, 1H), 7.93-8.04 (m, 1H), 8.35 (d, J=5.0 Hz, 1H), 8.38 (d, J=1.8 Hz, 1H)

(ESI pos.) m/z: 243([M+H]+), 245([M+3]+)

(2) A mixture of 4-bromo-N-propylpyridine-2-carboxamide (450 mg), phenylboronic acid (330 mg), potassium carbonate (380 mg), tetrakis(triphenylphosphine)palladium (210 mg), dimethylformamide (6.5 mL) and ethanol (3.5 mL) was stirred under irradiation with microwave while heating at 150° C. for 10 min. Water was added to the reaction mixture, followed by extraction with ethyl acetate. The organic phase was washed with water and brine, and then dried over anhydrous magnesium sulfate. After the desiccant was filtered off, the solvent was distilled off under reduced pressure. The resulting residue was purified by column chromatography (silica gel cartridge, hexane:ethyl acetate=67:33-50:50) to afford 4-phenyl-N-propylpyridine-2-carboxamide (390 mg).

1H NMR (600 MHz, CHLOROFORM-d) d ppm 1.02 (t, J=7.3 Hz, 3H), 1.65-1.72 (m, 2H), 3.43-3.51 (m, 2H), 7.28-8.60 (m, 9H)

(ESI pos.) m/z: 241([M+H]+)

(3) Lithium aluminum hydride was added to a solution of 4-phenyl-N-propylpyridine-2-carboxamide (350 mg) in tetrahydrofuran (10 mL), and the mixture was stirred at room temperature for 1 hr, followed by stirring with heating at 70° C. for 2 hr. After the mixture was cooled in ice, 10% aqueous sodium hydroxide solution was added, and the resulting mixture was stirred at room temperature for 30 min. The reaction mixture was dried over anhydrous magnesium sulfate, the desiccant was filtered off and the solvent was distilled off under reduced pressure. The resulting residue was purified by column chromatography (NH silica gel cartridge, hexane:ethyl acetate=50:50-0:100) to afford the title compound (107 mg).

1H NMR (600 MHz, CHLOROFORM-d) d ppm 0.93-0.97 (m, 3H), 1.51-1.62 (m, 2H), 2.67 (t, J=7.1 Hz, 2H), 3.97 (s, 2H), 7.37-7.56 (m, 6H), 7.63-7.68 (m, 2H), 8.60 (d, J=5.0 Hz, 1H)

(ESI pos.) m/z: 227([M+H]+)

Production Example 21

N-{1-[2-(4-Fluorophenyl)pyridin-4-yl]ethyl}cyclobutaneamine

[Chem 37]

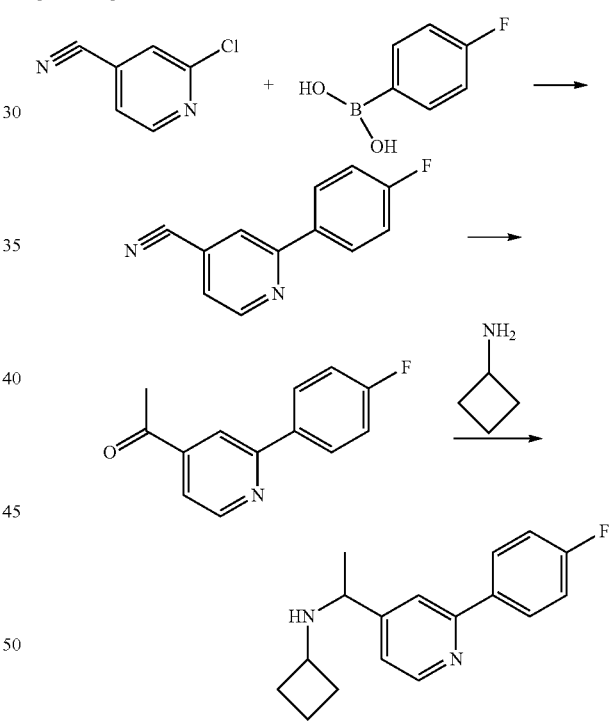

(1) A mixture of 2-chloro-isonicotinonitrile (1.9 g), 4-fluorophenylboronic acid (2.9 g), sodium carbonate (4.3 g), tetrakis(triphenylphosphine)palladium (480 mg), 1,2-dimethoxyethane (40 mL), ethanol (20 mL) and water (20 mL) was stirred while heating at 100° C. for 2 hr. The solvent was distilled off under reduced pressure, and the resulting residue was then purified by column chromatography (silica gel cartridge, hexane:ethyl acetate=94:6-50:50) to afford 2-(4-fluorophenyl)pyridine-4-carbonitrile (2.0 g).

1H NMR (200 MHz, CHLOROFORM-d) d ppm 7.13-7.25 (m, 2H), 7.44 (dd, J=4.8, 1.3 Hz, 1H), 7.87-8.07 (m, 3H), 8.81-8.88 (m, 1H)

(ESI pos.) m/z: 199([M+H]+)

(2) Methylmagnesium bromide (1.85 g) was added to a suspension of 2-(4-fluorophenyl)pyridine-4-carbonitrile (1.0 g) in diethyl ether (10 mL), and the mixture was stirred at room temperature overnight. After adding ice and 2M hydrochloric acid and stirring, the resulting mixture was made basic with 2M aqueous sodium hydroxide solution. After exracting with ethyl acetate, the organic phase was separated out and the solvent was distilled off The resulting residue was purified by column chromatography (silica gel cartridge, hexane: ethyl acetate=98:2-80:20) to afford 1-[2-(4-fluorophenyl)pyridin-4-yl]ethanone (350 mg).

1H NMR (200 MHz, CHLOROFORM-d) d ppm 2.68 (s, 3H), 7.12-7.28 (m, 2H), 7.61-7.68 (m, 1H), 7.99-8.16 (m, 3H), 8.82-8.89 (m, 1H)

(3) Titanium(IV) isopropoxide (1.85 g) was added to a solution of cyclobutylamine (930 mg) in methanol (10 mL), and the mixture was stirred at room temperature for 10 min. A solution of 1-[2-(4-fluorophenyl)pyridin-4-yl]ethanone (350 mg) in methanol (5 mL) was added thereto and the mixture was stirred at room temperature overnight. Saturated sodium hydrogen carbonate solution was added to the reaction mixture, which was then filtered through Celite, and the solvent was distilled off under reduced pressure. After extracting with chloroform, the organic phase was separated out, and the solvent was distilled off under reduced pressure. The resulting residue was purified by column chromatography (NH silica gel cartridge, hexane:ethyl acetate=98:2-80:20) to afford the title compound (430 mg).

1H NMR (200 MHz, CHLOROFORM-d) d ppm 1.30-1.39 (m, 3H), 1.42-1.79 (m, 4H), 2.00-2.33 (m, 2H), 3.05-3.22 (m, 1H), 3.82 (q, J=6.7 Hz, 1H), 7.06-8.09 (m, 6H), 8.56-8.61 (m, 1H)

Production Example 22

N-{2-[({Amino[4-(trifluoromethoxy)phenyl] methylidene}amino)oxy]-2-oxoethyl}-N-cyclobutyl-1-methyl-1H-imidazole-4-carboxamide

[Chem 38]

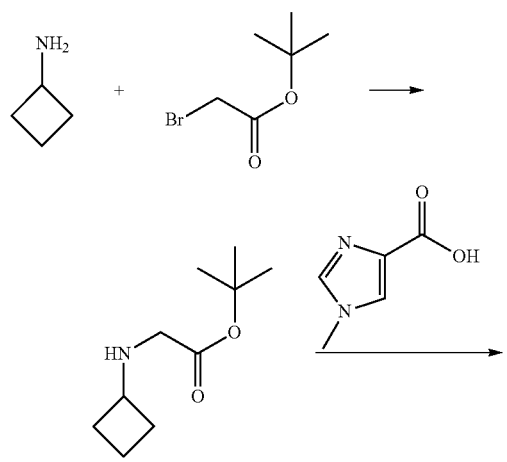

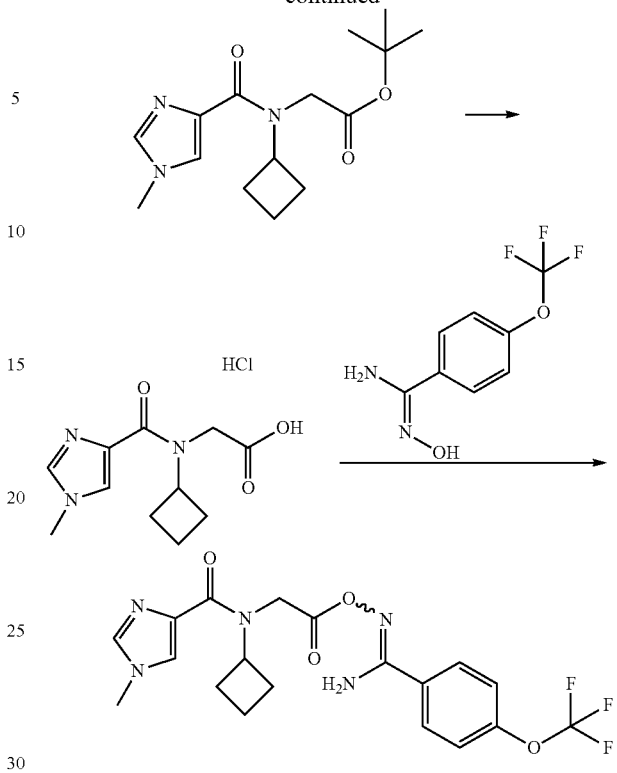

(1) Cyclobutylamine (370 mg) was added to an ice-cold suspension of tert-butyl bromoacetate (1.0 g) and potassium carbonate (700 mg) in acetonitrile (20 mL), and the mixture was stirred at room temperature overnight. Water was added to the reaction mixture, which was then extracted with chloroform. The organic phase was separated out and the solvent was distilled off under reduced pressure to afford tert-butyl N-cyclobutylglycinate (949 mg) as the residue.

1H NMR (200 MHz, CHLOROFORM-d) d ppm 1.42-1.48 (m, 9H), 1.49-2.25 (m, 6H), 3.23 (s, 1H), 3.38 (s, 2H)

(ESI pos.) m/z: 186([M+H]+)

(2) According to the similar procedure as in Production Example 8, tert-butyl N-cyclobutyl-N-[(1-methyl-1H-imidazol-4-yl)carbonyl]glycinate (490 mg) was obtained from tert-butyl N-cyclobutylglycinate (949 mg) and methyl-1H-imidazole-4-carboxylic acid (650 mg).

1H NMR (200 MHz, CHLOROFORM-d) d ppm 1.26-2.35 (m, 15H), 3.53-3.78 (m, 3H), 3.95-5.74 (m, 3H), 7.28-7.57 (m, 2H)

(ESI pos.) m/z: 294([M+H]+)

(3) To a solution of tert-butyl N-cyclobutyl-N-[(1-methyl-1H-imidazol-4-yl)carbonyl]glycinate (200 mg) in ethyl acetate (4 mL) was added 4N hydrochloric acid/ethyl acetate solution (4 mL), and the mixture was stirred at room temperature overnight. The solvent was distilled off under reduced pressure to afford N-cyclobutyl-N-[(1-methyl-1H-imidazol-4-yl)carbonyl]glycine hydrochloride (150 mg).

1H NMR (200 MHz, DMSO-d6) d ppm 1.41-1.87 (m, 2H), 1.95-2.34 (m, 4H), 3.44-4.98 (m, 6H), 7.68-9.85 (m, 3H)

(ESI pos.) m/z: 238([M+H]+)

(4) According to the similar procedure as in Production Example 8, N-cyclobutyl-N2-({(E)-(hydroxyimino)[4-(trifluoromethoxy)phenyl]methyl}amino)-2-oxoethyl]-1-methyl-1H-imidazole-4-carboxamide (85 mg) was obtained from N-cyclobutyl-N-[(1-methyl-1H-imidazol-4-yl)carbonyl]glycine hydrochloride (150 mg) and 4-(trifluoromethoxy)benzamidoxime (130 mg).

1H NMR (600 MHz, CHLOROFORM-d) d ppm 1.54-1.80 (m, 2H), 2.08-2.36 (m, 4H), 3.71 (br. s., 3H), 4.36-5.68 (m, 3H), 7.19-7.56 (m, 4H), 7.72-7.77 (m, 2H)

Production Example 23

N-Cyclobutyl-N-{[2-(4-fluoro-3-hydroxyphenyl)pyridin-4-yl]methyl}-1-methyl-1H-imidazole-4-carboxamide

[Chem 39]

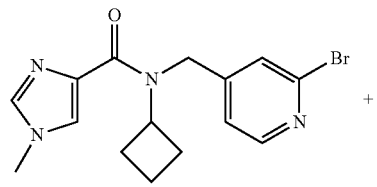

+

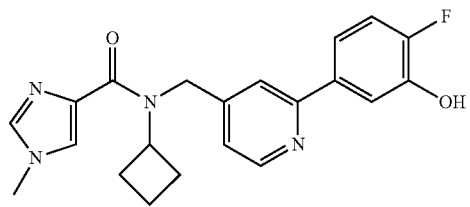

According to the similar procedure as in Production Example 13, the title compound (200 mg) was obtained from N-[(2-bromopyridin-4-yl)methyl]-N-cyclobutyl-1-methyl-1H-imidazole-4-carboxamide (200 mg) and 4-fluoro-3-hydroxyphenylboronic acid (140 mg).

1H NMR (600 MHz, CHLOROFORM-d) d ppm 1.56-1.71 (m, 2H), 2.02-2.28 (m, 4H), 3.58-3.84 (m, 3H), 4.71-5.93 (m, 3H), 7.03-7.62 (m, 8H), 8.49-8.54 (m, 1H)

(ESI pos.) m/z: 381([M+H]+)

The following compound was synthesized according to the similar procedure.

N-Cyclobutyl-N-{[2-(3-fluoro-4-hydroxyphenyl)pyridin-4-yl]methyl}-1-methyl-1H-imidazole-4-carboxamide 1H NMR (600 MHz, CHLOROFORM-d) d ppm 1.39-2.40 (m, 6H), 3.70 (br. s., 3H), 4.66-5.97 (m, 3H), 6.89-7.93 (m, 8H), 8.52 (d, J=5.0 Hz, 1H)

(ESI pos.) m/z: 381([M+H]+)

Production Example 24

2-(4-Fluorophenyl)pyridine-4-carbaldehyde

[Chem 40]

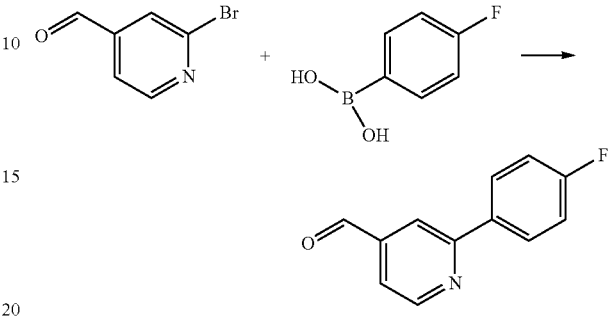

According to the similar procedure as in Production Example 13, the title compound was obtained from 2-bromopyridine-4-carboxaldehyde (300 mg) and 4-fluorophenylboronic acid (328 mg). 1H NMR (600 MHz, CHLOROFORM-d) d ppm 6.64-9.00 (m, 7H), 10.14 (s, 1H) (ESI pos.) m/z: 202([M+H]+)

Working Example 1

1-Methyl-N-(propan-2-yl)-N-({2-[4-(trifluoromethoxy)phenyl]pyridin-4-yl}methyl)-1H-imidazole-4-carboxamide dihydrochloride

[Chem 41]

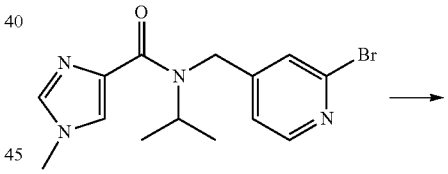

A mixture of N-[(2-bromopyridin-4-yl)methyl]-1-methyl-N-(propan-2-yl)-1H-imidazole-4-carboxamide (100 mg), 4-trifluoromethoxyphenylboronic acid (122 mg), tetrakis(triphenylphosphine)palladium (34 mg), potassium carbonate (82 mg), dimethylformamide (1.2 mL) and ethanol (0.4 mL) was stirred under irradiation with microwave while heating at 150° C. for 30 min. After diluting with chloroform, the mixture was washed with water and further extracted with chloroform. The organic phase was separated out, and the solvent was distilled off under reduced pressure. The resulting residue was diluted with ethyl acetate, and a small amount of NH silica gel was added thereto, followed by stirring. The NH silica gel was filtered off, and the solvent was then distilled off under reduced pressure. The resulting residue was purified by HPLC. The resulting residue was dissolved in acetonitrile and water, and 2N hydrochloride was added thereto, followed by lyophilization to afford the title compound (94 mg).

Working Example 2

N-Cyclobutyl-1-methyl-N-({2-[4-(trifluoromethoxy)phenyl]pyridin-4-yl}methyl)-1H-imidazole-4-carboxamide dihydrochloride

[Chem 42]

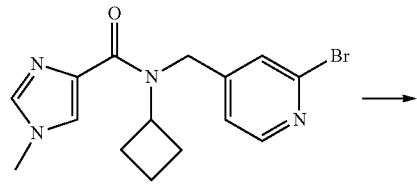

A mixture of N-[(2-bromopyridin-4-yl)methyl]-N-cyclobutyl-1-methyl-1H-imidazole-4-carboxamide (200 mg), 4-trifluoromethoxyphenylboronic acid (130 mg), tetrakis(triphenylphosphine)palladium (66 mg), cesium carbonate (260 mg), toluene (1.9 mL), ethanol (1.9 mL) and water (1.2 mL) was stirred under irradiation with microwave while heating at 150° C. for 30 min. After extracting with ethyl acetate, the whole organic phase was collected and dried over magnesium sulfate. After the desiccant was filtered off, the filtrate was concentrated in vacuo. The resulting residue was purified by PTLC (silica gel, chloroform:methanol=10:1) and HPLC. The resulting residue was dissolved in acetonitrile and water, and 2N hydrochloric acid was added, followed by lyophilization to afford the title compound (64 mg).

Working Example 3

N-Cyclobutyl-1-methyl-N-{[2-(2,4,5-trifluorophenyl)pyridin-4-yl]methyl}-1H-imidazole-4-carboxamide dihydrochloride

[Chem 43]

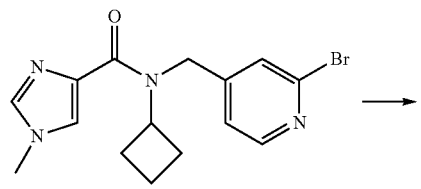

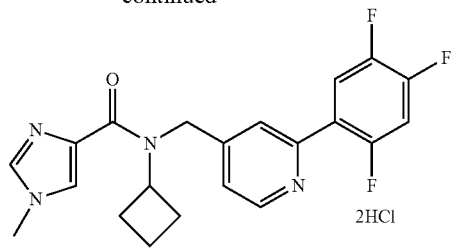

A mixture of N-[(2-bromopyridin-4-yl)methyl]-N-cyclobutyl-1-methyl-1H-imidazole-4-carboxamide (100 mg), 2,4,5-trifluorophenylboronic acid (76 mg), tetrakis(triphenylphosphine)palladium (33 mg), cesium carbonate (187 mg), toluene (0.6 mL), ethanol (0.6 mL) and water (0.4 mL) was stirred while heating at 100° C. for 3 hr. The supernatant of the reaction mixture was purified by PTLC (NH silica gel, ethyl acetate) and HPLC. The resulting residue was dissolved in acetonitrile, and 4N hydrochloric acid/ethyl acetate (0.1 mL) was added thereto, followed by concentration to afford the title compound (86 mg).

Working Example 4

N-[4-Fluoro-3-(pyridin-2-yl)benzyl]-1-methyl-N-(propan-2-yl)-1H-imidazole-4-carboxamide

[Chem 44]

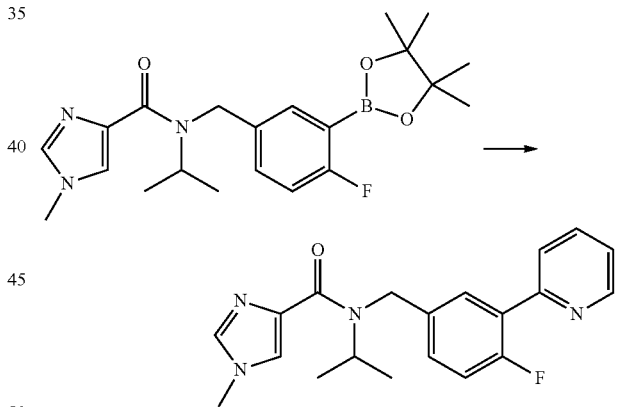

A mixture of N-[4-fluoro-3-(4,4,5,5-tetramethyl-1,3,2-dioxaborolan-2-yl)benzyl]-1-methyl-N-(propan-2-yl)-1H-imidazole-4-carboxamide (100 mg), 2-bromopyridine (47 mg), tetrakis(triphenylphosphine)palladium (29 mg), potassium carbonate (69 mg), dimethylformamide (1.0 mL) and ethanol (0.5 mL) was stirred under irradiation with microwave while heating at 150° C. for 50 min. After the mixture was diluted with ethyl acetate, the insoluble matter was filtered off, and the solvent was distilled off under reduced pressure. The residue was diluted with ethyl acetate, and then washed with water and brine. The organic phase was collected and dried over sodium sulfate, the desiccant was filtered off and the solvent was then distilled off under reduced pressure. The resulting residue was purified by column chromatography (NH silica gel cartridge, hexane:ethyl

Working Example 5

N-Cyclobutyl-N-[4-fluoro-3-(6-fluoropyridin-3-yl)benzyl]-1-methyl-1H-imidazole-4-carboxamide hydrochloride

[Chem 45]

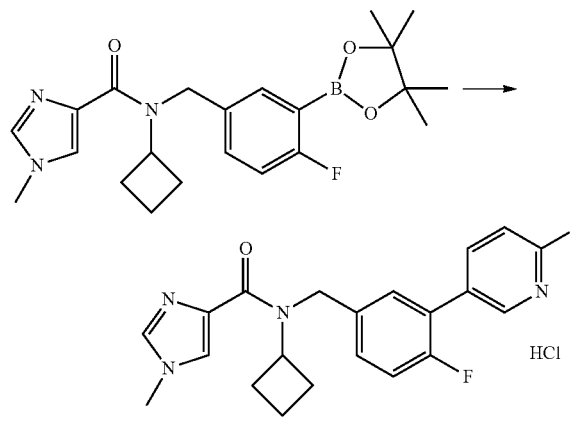

A mixture of N-cyclobutyl-N-[4-fluoro-3-(4,4,5,5-tetramethyl-1,3,2-dioxaborolan-2-yl)benzyl]-1-methyl-1H-imidazole-4-carboxamide (300 mg), 5-bromo-2-fluoropyridine (141 mg), tetrakis(triphenylphosphine)palladium (84 mg), cesium carbonate (237 mg), toluene (2.7 mL), ethanol (2.7 mL) and water (1.6 mL) was stirred under irradiation with microwave while heating at 150° C. for 30 min. Water was added to the reaction mixture, which was then extracted with chloroform, and the solvent was distilled off under reduced pressure. The resulting residue was purified by column chromatography (NH silica gel cartridge, hexane:ethyl acetate=75:25-0:100) and HPLC. The resulting residue was dissolved in acetonitrile and 4N hydrochloric acid/ethyl acetate (0.7 mL) was added thereto, followed by concentration to afford the title compound (45 mg).

Working Example 6

N-Cyclobutyl-N-{4-fluoro-3-[6-(trifluoromethyl)pyrimidine-4-yl]benzyl}-1-methyl-1H-imidazole-4-carboxamide

[Chem 46]

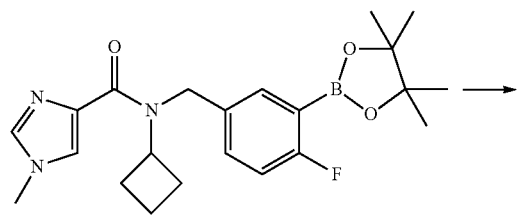

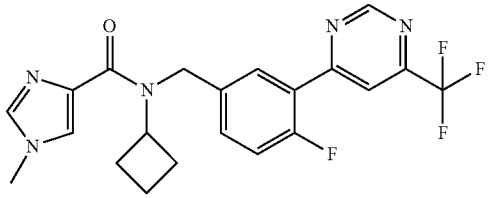

A mixture of N-cycloburyl-N-[4-fluoro-3-(4,4,5,5-tetramethyl-1,3,2-dioxaborolan-2-yl)benzyl]-1-methyl-1H-imidazole-4-carboxamide (200 mg), 4-chloro-6-trifluoromethylpyrimidine (139 mg), tetrakis(triphenylphosphine)palladium (56 mg), cesium carbonate (315 mg), toluene (0.7 mL), ethanol (0.7 mL) and water (0.5 mL) was stirred while heating at 100° C. for 3 hr. The supernatant of the reaction mixture was purified by PTLC (NH silica gel, ethyl acetate) and HPLC. The resulting residue was stirred in isopropyl ether and separated out by filtration to afford the title compound (76 mg).

Working Example 7

1-Methyl-N-[(4-phenylpyridin-2-yl)methyl]-N-propyl-1H-imidazole-4-carboxamide

[Chem 47]

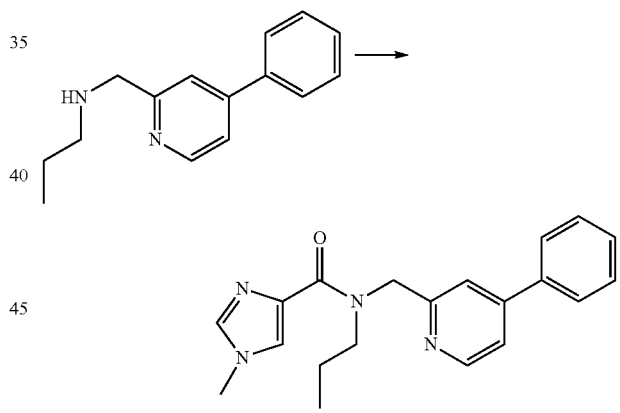

To a solution of methyl-1H-imidazole-4-carboxylic acid (53 mg) in dimethylformamide (1 mL) was added 1-hydroxybenzotriazole hydrate (HOBT.H$_2$O) (64 mg) and 1-(3-dimethylaminopropyl)-3-ethylcarbodiimide hydrochloride (EDC.HCl) (81 mg) and the mixture was stirred at room temperature for 10 min. A solution of N-[(4-phenylpyridin-2-yl)methyl]propan-1-amine (80 mg) in dimethylformamide (2 mL) was added thereto, and the mixture was stirred at room temperature overnight. The solvent was distilled off under reduced pressure and then saturated aqueous sodium hydrogen carbonate solution was added, followed by extraction with ethyl acetate. The organic phase was collected and dried over anhydrous sodium sulfate. After the desiccant was filtered off, the solvent was distilled off under reduced pressure. The resulting residue was purified by column chromatography (silica gel cartridge, chloroform:methanol=98:2-82:18)

and (the same column, chloroform:methanol=100:0-90:10) to afford the title compound (33 mg).

Working Example 8

N-Cyclobutyl-1-methyl-N-({2-[4-(trifluoromethoxy)phenyl]-1,3-thiazol-4-yl}methyl)-1H-imidazole-4-carboxamide

[Chem 48]

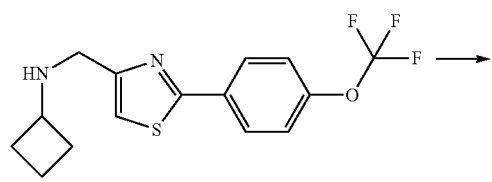

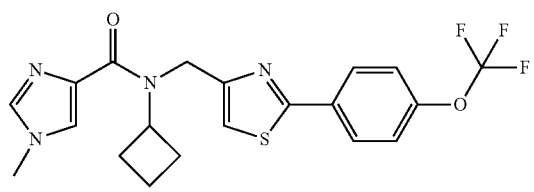

A solution of N-({2-[4-(trifluoromethoxy)phenyl]-1,3-thiazol-4-yl}methyl)cyclobutaneamine (430 mg), methyl-1H-imidazole-4-carboxylic acid (451 mg), 2-(1H-7-azabenzotriazol-1-yl)-1,1,3,3-tetramethyl uronium hexafluorophosphate methanaminium (HATU) (598 mg) and diisopropylethylamine (0.69 mL) in acetonitrile (15 mL) was stirred at room temperature for 3 days. Water was added to the reaction mixture, followed by extraction with chloroform. The solvent was distilled off under reduced pressure, and the resulting residue was purified by column chromatography (NH silica gel cartridge, hexane:ethyl acetate=75:25-0:100) and PTLC (silica gel, chloroform:methanol=19:1). The resulting residue was re-crystalized with isopropyl ether to afford the title compound (216 mg).

Working Example 9

N-Cyclobutyl-N-{1-[2-(4-fluorophenyl)pyridin-4-yl]ethyl}-1-methyl-1H-imidazole-4-carboxamide

[Chem 49]

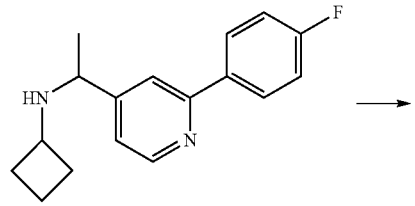

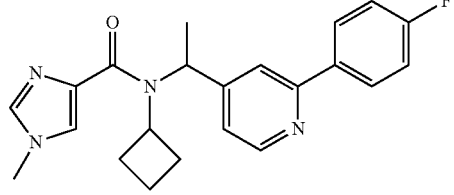

A solution of N-{1-[2-(4-fluorophenyl)pyridin-4-yl]ethyl}cyclobutaneamine (100 mg), 1-methyl-1H-imidazole-4-carbonyl chloride (110 mg) and triethylamine (100 mg) in chloroform (5 mL) was stirred at room temperature overnight. Water was added thereto, followed by extraction with chloroform, and the solvent was distilled off under reduced pressure. The resulting residue was purified by column chromatography (NH silica gel cartridge, hexane:ethyl acetate=75:25-0:100) to afford the title compound (120 mg).

Working Example 10

1-Ethyl-N-{[2-(4-fluorophenyl)pyridin-4-yl]methyl}-N-(propan-2-yl)-1H-imidazole-4-carboxamide dihydrochloride

[Chem 50]

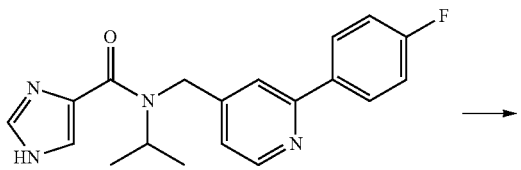

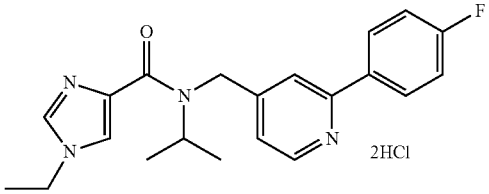

Ethyl iodide (104 mg) was added to a solution of N-{[2-(4-fluorophenyl)pyridin-4-yl]methyl}-N-(propan-2-yl)-1H-imidazole-4-carboxamide (150 mg) and sodium hydride (22 mg) in dimethylformamide (3 mL), and the mixture was stirred at room temperature overnight. Saturated aqueous sodium hydrogen carbonate solution was added to the reaction mixture, which was extracted with chloroform. The organic phase was collected and dried over anhydrous magnesium sulfate. After the desiccant was filtered off, the solvent was distilled off under reduced pressure. The resulting residue was purified by HPLC and PTLC (silica gel, chloroform:acetone=1:1). The resulting residue was dissolved in acetonitrile and water and 2N hydrochloric acid was added thereto, followed by lyophilization to afford the title compound (40 mg).

Working Example 11

N-[4-Fluoro-3-(4-methyl-1H-pyrazol-1-yl)benzyl]-1-methyl-N-(propan-2-yl)-1H-imidazole-4-carboxamide hydrochloride

[Chem 51]

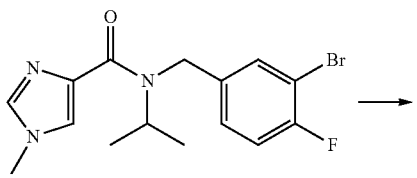

A solution of N-(3-bromo-4-fluorobenzyl)-1-methyl-N-(propan-2-yl)-1H-imidazole-4-carboxamide (200 mg), 4-methylpyrazole (46 mg), L-proline (65 mg), copper iodide (54 mg) and potassium carbonate (78 mg) in dimethylformamide (1.0 mL) was stirred at room temperature for 10 min, followed by stirring with heating at 130° C. for 14 hr. The reaction mixture was diluted with ethyl acetate and then washed with water. The solvent was distilled off under reduced pressure, and the resulting residue was purified by PTLC (NH silica gel, ethyl acetate), HPLC, and PTLC (silica gel, chloroform:methanol=19:1). The resulting residue was dissolved in acetonitrile, and 4N hydrochloric acid/ethyl acetate (0.04 mL) was added thereto, followed by concentration to afford the title compound (29 mg).

Working Example 12

N-[4-Fluoro-3-(1H-imidazol-1-yl)benzyl]-1-methyl-N-(propan-2-yl)-1H-imidazole-4-carboxamide dihydrochloride

[Chem 52]

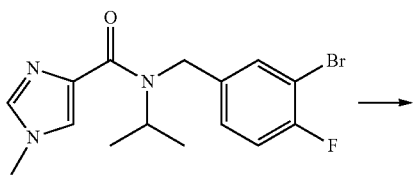

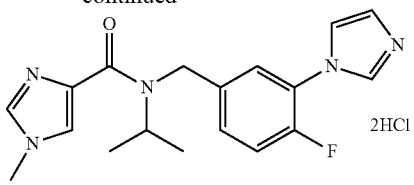

A solution of N-(3-bromo-4-fluorobenzyl)-1-methyl-N-(propan-2-yl)-1H-imidazole-4-carboxamide (200 mg), 1-methylimidazole (200 mg), trans-1,2-bis(methylamino)cyclohexane (5 mg), copper iodide (3 mg) and cesium carbonate (140 mg) in dioxane (1.0 mL) was stirred under irradiation with microwave while heating at 150° C. for 30 min. The reaction mixture was treated with NH2 cartridge, and then purified by HPLC. The resulting residue was dissolved in acetonitrile and water, and 2N hydrochloric acid was added thereto, followed by lyophilization to afford the title compound (25 mg).

Working Example 13

N-[4-Fluoro-3-(4-methyl-1H-imidazol-1-yl)benzyl]-1-methyl-N-(propan-2-yl)-1H-imidazole-4-carboxamide dihydrochloride

[Chem 53]

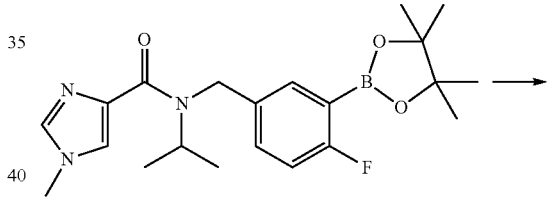

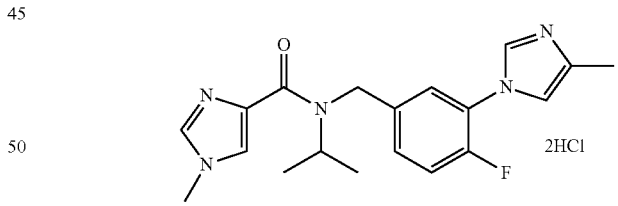

A solution of N-[4-fluoro-3-(4,4,5,5-tetramethyl-1,3,2-dioxaborolan-2-yl)benzyl]-1-methyl-N-(propan-2-yl)-1H-imidazole-4-carboxamide (600 mg), 4-methylimidazole (205 mg) and di-μ-hydroxobis[(N,N,N',N'-tetramethylethylenediamine)copper(II)]dichloride (231 mg) in chloroform (6.0 mL) was stirred under oxygen atmosphere at room temperature for 2 days. The reaction mixture was filtered through Celite, and the solvent was then distilled off under reduced pressure. The resulting residue was purified by column chromatography (NH silica gel cartridge, hexane:ethyl acetate=75:25-0:100), PTLC(NH silica gel, ethyl acetate) and PTLC (silica gel, chloroform:methanol=19:1). The resulting residue was dissolved in acetonitrile and 4N hydrochloric acid/ethyl acetate (0.08 mL) was added thereto, followed by concentration to afford the title compound (59 mg).

Working Example 14

N-Cyclobutyl-1-methyl-N-({3-[4-(trifluoromethoxy)phenyl]-1,2,4-oxadiazol-5-yl}methyl)-1H-imidazole-4-carboxamide

[Chem 54]

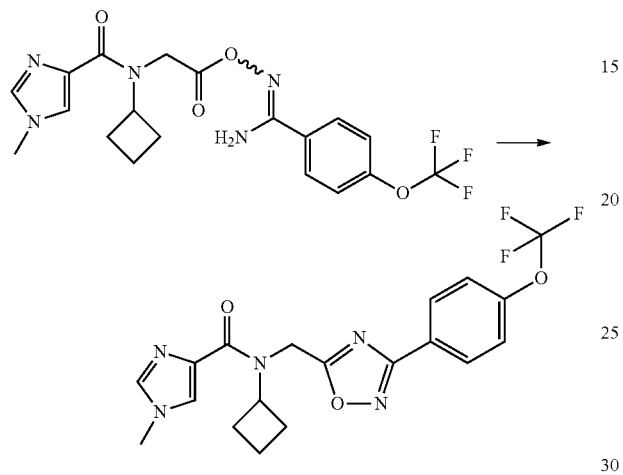

A mixture of N-{2-[({amino[4-(trifluoromethoxy)phenyl]methylidene}amino)oxy]-2-oxoethyl}-N-cyclobutyl-1-methyl-1H-imidazole-4-carboxamide (75 mg), acetic acid (0.5 mL) and dimethylformamide (0.5 mL) was stirred while heating at 120° C. for 2 hr. After the solvent was distilled off under reduced pressure, the resulting residue was purified by HPLC to afford the title compound (7 mg).

Working Example 15

N-Cyclobutyl-N-{4-fluoro-3-[6-(pyrrolidin-1-yl)pyridin-3-yl]benzyl}-1-methyl-1H-imidazole-4-carboxamide dihydrochloride

[Chem 55]

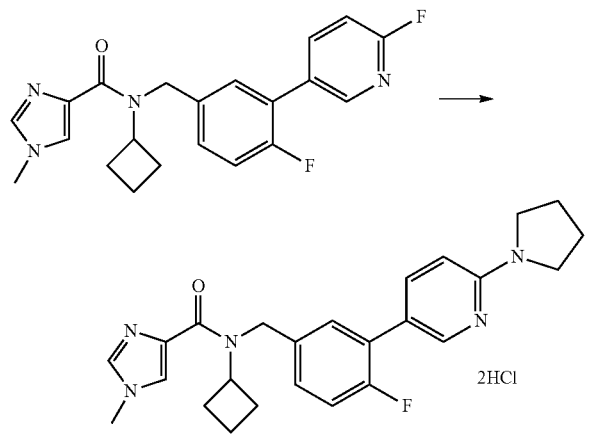

A mixture of N-cyclobutyl-N-[4-fluoro-3-(6-fluoropyridin-3-yl)benzyl]-1-methyl-1H-imidazole-4-carboxamide (20.5 mg), pyrrolidine (0.5 mL) and tetrahydrofuran (0.5 mL) was stirred while heating at 110° C. for 2.5 hr, followed by at 100° C. for 5 hr, and then returned to room temperature. The reaction mixture was purified by PTLC (NH silica gel, ethyl acetate) and PTLC (silica gel, chloroform:methanol=19:1). The resulting residue was dissolved in acetonitrile, and 4N hydrochloric acid/ethyl acetate (0.03 mL) was added thereto, followed by concentration to afford the title compound (17 mg).

Working Example 16

N-Cyclobutyl-N-({2-[3-(difluoromethoxy)-4-fluorophenyl]pyridin-4-yl}methyl)-1-methyl-1H-imidazole-4-carboxamide dihydrochloride

[Chem 56]

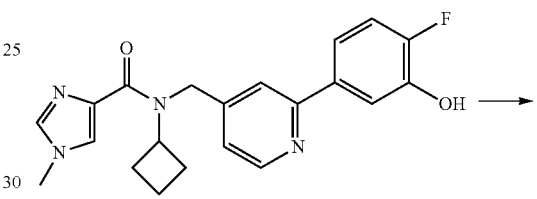

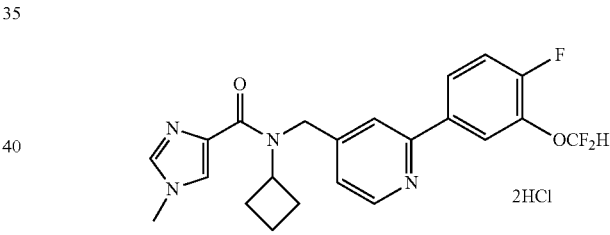

A mixture of N-cyclobutyl-N-{[2-(4-fluoro-3-hydroxyphenyl)pyridin-4-yl]methyl}-1-methyl-1H-imidazole-4-carboxamide (200 mg), sodium chlorodifluoroacetate (190 mg), cesium carbonate (241 mg), dimethylformamide (1.5 mL) and water (0.15 mL) was stirred while heating at 100° C. for 5 hr. After the reaction mixture was cooled in ice, concentrated hydrochloric acid (0.2 mL) was added thereto, and the resulting mixture was stirred for 1 hr. After addition of an aqueous solution of 2M sodium hydroxide, the mixture was extracted with ethyl acetate. The organic phase was separated out, and the solvent was distilled off under reduced pressure. The resulting residue was purified by HPLC. The resulting residue was dissolved in acetonitrile, and 4N hydrochloric acid/ethyl acetate was added thereto, followed by concentration to afford the title compound (30 mg).

Tables 1-1 to 1-21 show the structural formulae and the instrumental data of the compounds described in Working Examples 1 to 16 and those of the compounds synthesized by similar methods. The number shown in the column of "Working Example" represents which of the above-mentioned Working Examples 1 to 16 was used to synthesize the compound.

TABLE 1-1

| Compound | Example | Structure | Salt | NMR | (ESI pos.) m/z (ESI neg.) m/z |
|---|---|---|---|---|---|
| 1 | 1 | 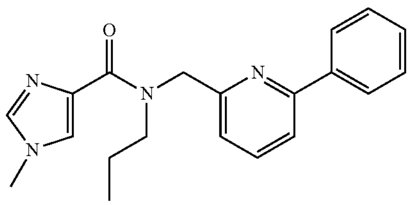 [SMILES: CCCN(Cc1cccc(-c2ccccc2)n1)C(=O)c1cn(C)cn1] | | | 335 ([M + H]+) |
| 2 | 1 | 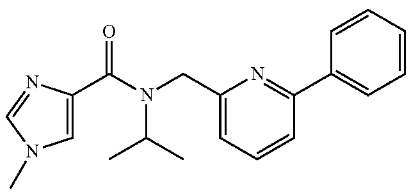 [SMILES: CC(C)N(Cc1cccc(-c2ccccc2)n1)C(=O)c1cn(C)cn1] | | | 335 ([M + H]+) |
| 3 | 1 | 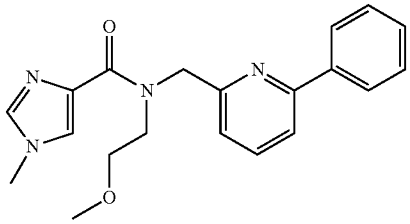 [SMILES: COCCN(Cc1cccc(-c2ccccc2)n1)C(=O)c1cn(C)cn1] | | | 351 ([M + H]+) |
| 4 | 1 | 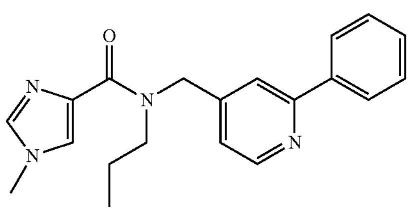 [SMILES: CCCN(Cc1ccnc(-c2ccccc2)c1)C(=O)c1cn(C)cn1] | | 1H NMR (600 MHz, CHLOROFORM-d) d ppm 0.81-0.98 (m, 3 H), 1.61-1.76 (m, 2 H), 3.36-4.07 (m, 2 H), 3.65-3.77 (m, 3 H), 4.73-5.55 (m, 2 H), 7.06-8.68 (m, 10 H) | 335 ([M + H]+) |
| 5 | 7 | 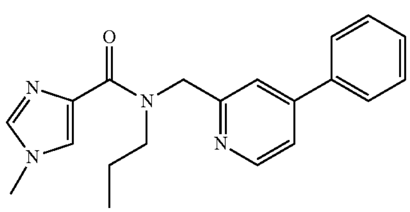 | | 1H NMR (600 MHz, CHLOROFORM-d) d ppm 0.83-0.95 (m, 3 H), 1.64-1.76 (m, 2 H), 3.36-4.10 (m, 2 H), 3.65-3.79 (m, 3 H), 4.85-5.62 (m, 2 H), 7.29-7.49 (m, 5 H), 7.55-7.65 (m, 4 H), 8.59 (br. s., 1 H) | 335 ([M + H]+) |
| 6 | 1 | 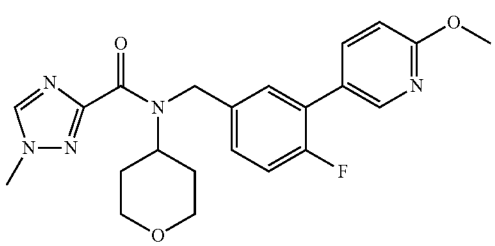 | | | 426 ([M + H]+) |
| 7 | 1 | 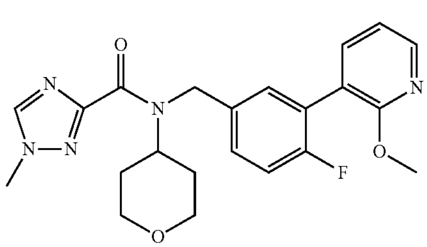 | | | 426 ([M + H]+) |

TABLE 1-1-continued
| Compound | Example | Structure | Salt | NMR | (ESI pos.) m/z (ESI neg.) m/z |
|---|---|---|---|---|---|
| 8 | 8 | 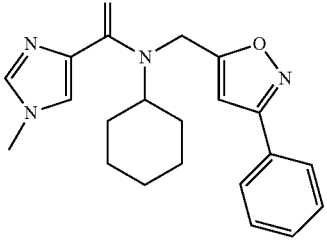 | | | 365 ([M + H]+) |
| 9 | 1 | 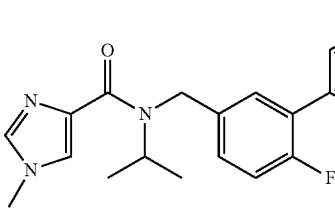 | 1HCl | 1H NMR (600 MHz, METHANOL-d3) d ppm 1.16-1.48 (m, 6 H) 3.76-4.14 (m, 3 H) 4.53-5.19 (m, 3 H) 7.14-8.41 (m, 7 H) 9.04 (br. s., 1 H) | 371 ([M + H]+) |
| 10 | 1 | 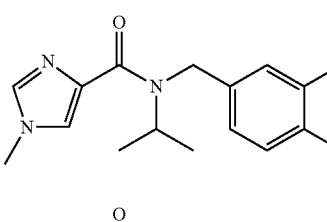 | | 1H NMR (600 MHz, CHLOROFORM-d) d ppm 1.09-1.36 (m, 6 H) 3.71 (br. s., 3 H) 4.56-5.85 (m, 3 H) 7.06-7.90 (m, 7 H) 8.56-8.80 (m, 2 H) | 353 ([M + H]+) |
| 11 | 1 | 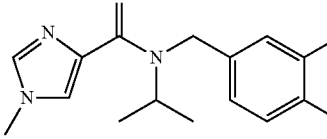 | | 1H NMR (600 MHz, CHLOROFORM-d) d ppm 1.09-1.34 (m, 6 H) 3.71 (br. s., 3 H) 4.53-5.84 (m, 3 H) 7.06-7.63 (m, 7 H) 8.62-8.67 (m, 2 H) | 353 ([M + H]+) |
TABLE 1-2
| Compound | Example | Structure | Salt | NMR | (ESI pos.) m/z (ESI neg.) m/z |
|---|---|---|---|---|---|
| 12 | 1 | 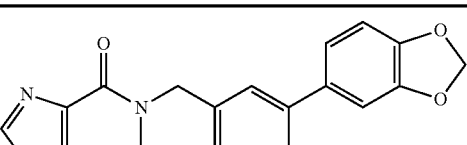 | | 1H NMR (600 MHz, CHLOROFORM d) d ppm 1.06-1.36 (m, 6 H) 3.62-3.77 (m, 3 H) 4.53-5.77 (m, 3 H) 5.99 (s, 2 H) 6.82-7.57 (m, 8 H) | 396 ([M + H]+) |
| 13 | 4 | 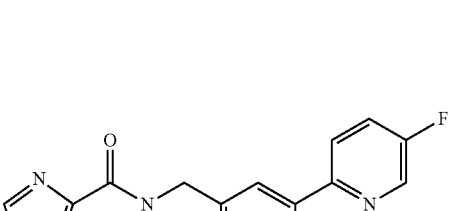 | | | 371 ([M + H]+) |

TABLE 1-2-continued

| Compound | Example | Structure | Salt | NMR | (ESI pos.) m/z (ESI neg.) m/z |
|---|---|---|---|---|---|
| 14 | 4 | 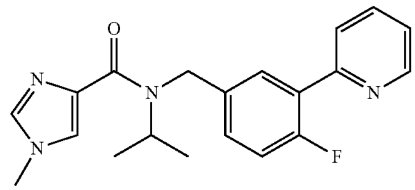 [SMILES: CC(C)N(Cc1ccc(F)c(-c2ccccn2)c1)C(=O)c1cn(C)cn1] | | 1H NMR (600 MHz, CHLOROFORM-d) d ppm 1.09-1.34 (m, 6 H) 3.62-3.78 (m, 3 H) 4.52-5.80 (m, 3 H) 7.02-7.95 (m, 8 H) 8.68-8.76 (m, 1 H) | 353 ([M + H]+) |
| 15 | 1 | 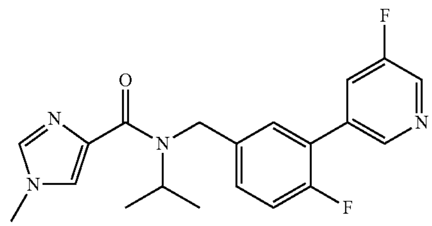 [SMILES: CC(C)N(Cc1ccc(F)c(-c2cncc(F)c2)c1)C(=O)c1cn(C)cn1] | | 1H NMR (600 MHz, CHLOROFORM-d) d ppm 1.08-1.35 (m, 6 H) 3.71 (br. s., 3 H) 4.53-5.85 (m, 3 H) 7.04-7.66 (m, 6 H) 8.39-8.66 (m, 2 H) | 371 ([M + H]+) |
| 16 | 1 | 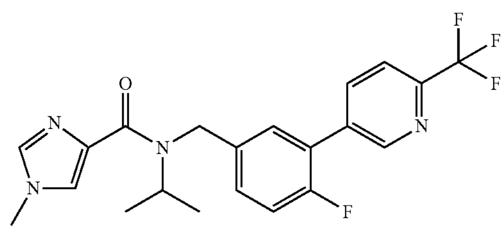 [SMILES: CC(C)N(Cc1ccc(F)c(-c2ccc(C(F)(F)F)nc2)c1)C(=O)c1cn(C)cn1] | | | 421 ([M + H]+) |
| 17 | 2 | 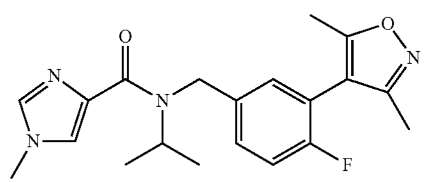 [SMILES: Cc1noc(C)c1-c1cc(CN(C(=O)c2cn(C)cn2)C(C)C)ccc1F] | | | 371 ([M + H]+) |
| 18 | 2 | 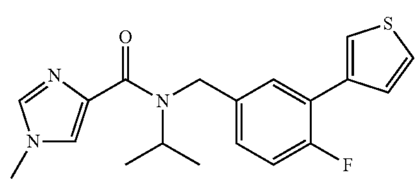 [SMILES: CC(C)N(Cc1ccc(F)c(-c2ccsc2)c1)C(=O)c1cn(C)cn1] | | 1H NMR (600 MHz, CHLOROFORM-d) d ppm 1.13-1.36 (m, 6 H), 3.71 (br. s., 3 H), 4.57-5.78 (m, 3 H), 7.00-7.59 (m, 8 H) | 358 ([M + H]+) |
| 19 | 2 | 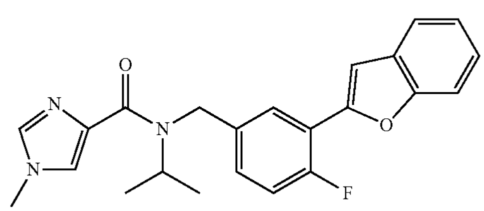 [SMILES: CC(C)N(Cc1ccc(F)c(-c2cc3ccccc3o2)c1)C(=O)c1cn(C)cn1] | | 1H NMR (600 MHz, CHLOROFORM-d) d ppm 0.66-1.82 (m, 6 H), 3.60-3.85 (m, 3 H), 4.58-5.81 (m, 3 H), 7.04-8.01 (m, 10 H) | 392 ([M + H]+) |
| 20 | 2 | 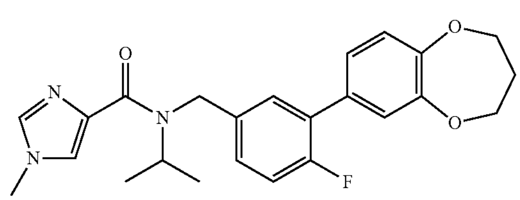 [SMILES: CC(C)N(Cc1ccc(F)c(-c2ccc3c(c2)OCCCO3)c1)C(=O)c1cn(C)cn1] | | | 424 ([M + H]+) |

TABLE 1-2-continued

| Compound | Example | Structure | Salt | NMR | (ESI pos.) m/z (ESI neg.) m/z |
|---|---|---|---|---|---|
| 21 | 2 | 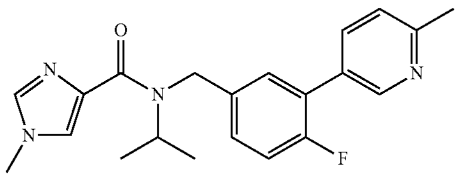 | | 1H NMR (600 MHz, CHLOROFORM-d) d ppm 1.09-1.40 (m, 6 H), 2.60 (s, 3 H), 3.71 (br. s, 3 H), 4.58-5.81 (m, 3 H), 7.04-7.79 (m, 7 H), 8.63 (br. s., 1 H) | 367 ([M + H]+) |
| 22 | 2 | 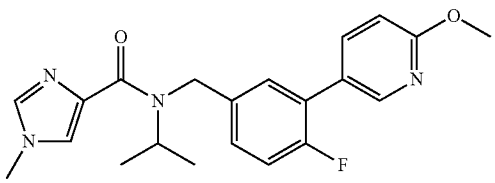 | | 1H NMR (600 MHz, CHLOROFORM-d) d ppm 1.13-1.32 (m, 6 H), 3.71 (br. s, 3 H), 4.00 (s, 3 H), 4.57-5.81 (m, 3 H), 6.80 (d, J = 8.7 Hz, 1 H), 7.03-7.78 (m, 6 H), 8.30 (br. s., 1 H) | 383 ([M + H]+) |

TABLE 1-3

| Compound | Example | Structure | Salt | NMR | (ESI pos.) m/z (ESI neg.) m/z |
|---|---|---|---|---|---|
| 23 | 2 | 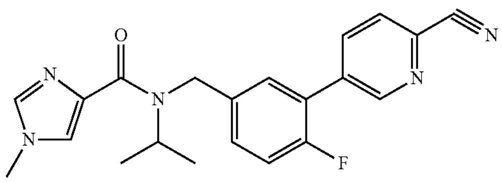 [SMILES: CC(C)N(Cc1ccc(F)c(-c2ccc(C#N)nc2)c1)C(=O)c1cn(C)cn1] | | 1H NMR (600 MHz, CHLOROFORM-d) d ppm 0.72-1.52 (m, 6 H), 3.64 (br. s, 3 H), 4.54-5.81 (m, 3 H), 6.99-8.03 (m, 7 H), 8.86 (br. s., 1 H) | 378 ([M + H]+) |
| 24 | 2 | 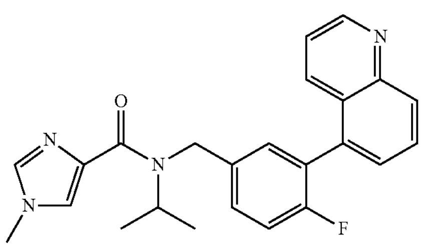 [SMILES: CC(C)N(Cc1ccc(F)c(-c2cccc3ncccc23)c1)C(=O)c1cn(C)cn1] | | | 403 ([M + H]+) |
| 25 | 2 | 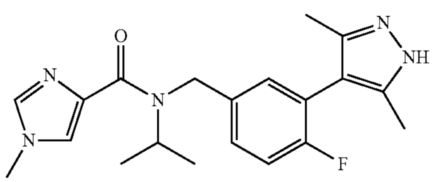 [SMILES: Cc1n[nH]c(C)c1-c1cc(CN(C(=O)c2cn(C)cn2)C(C)C)ccc1F] | | | 370 ([M + H]+) |
| 26 | 2 | 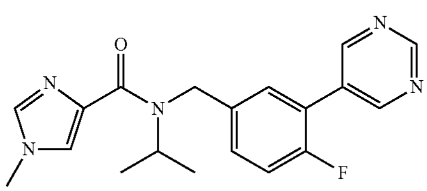 [SMILES: CC(C)N(Cc1ccc(F)c(-c2cncnc2)c1)C(=O)c1cn(C)cn1] | | 1H NMR (600 MHz, CHLOROFORM-d) d ppm 1.05-1.41 (m, 6 H), 3.72 (br. s., 3 H), 4.56-5.83 (m, 3 H), 7.09-7.65 (m, 5 H), 8.83-8.94 (m, 2 H), 9.19 (s, 1 H) | 354 ([M + H]+) |
| 27 | 2 | 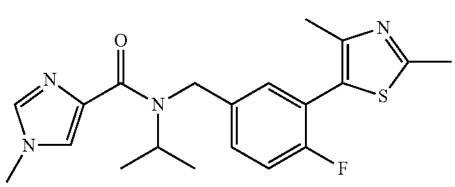 | | | 387 ([M + H]+) |

TABLE 1-3-continued

| Compound | Example | Structure | Salt | NMR | (ESI pos.) m/z (ESI neg.) m/z |
|---|---|---|---|---|---|
| 28 | 5 | 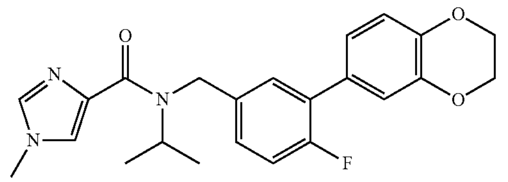 [SMILES: CC(C)N(Cc1ccc(F)c(-c2ccc3c(c2)OCCO3)c1)C(=O)c1cn(C)cn1] | | | 410 ([M + H]+) |
| 29 | 5 | 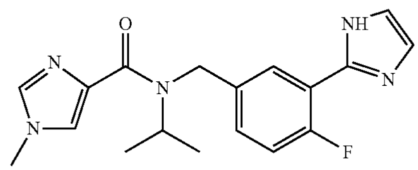 [SMILES: CC(C)N(Cc1ccc(F)c(-c2ncc[nH]2)c1)C(=O)c1cn(C)cn1] | | | 342 ([M + H]+) |
| 30 | 1 | 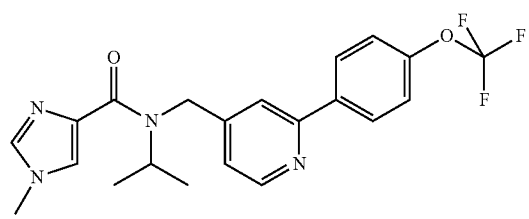 [SMILES: CC(C)N(Cc1ccnc(-c2ccc(OC(F)(F)F)cc2)c1)C(=O)c1cn(C)cn1] | 2HCl | 1H NMR (600 MHz, METHANOL-d3) d ppm 1.27-1.48 (m, 6 H), 4.04 (br. s., 3 H), 4.65-5.20 (m, 3 H), 7.55-7.66 (m, 2 H), 7.96-8.35 (m, 5 H), 8.75-8.84 (m, 1 H), 9.09 (br. s., 1 H) | 419 ([M + H]+) |
| 31 | 1 | 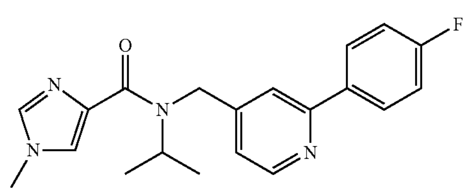 [SMILES: CC(C)N(Cc1ccnc(-c2ccc(F)cc2)c1)C(=O)c1cn(C)cn1] | 2HCl | 1H NMR (600 MHz, METHANOL-d3) d ppm 1.25-1.47 (m, 6 H), 4.03 (br. s., 3 H), 4.65-5.18 (m, 3 H), 7.42-7.49 (m, 2 H), 7.93-8.31 (m, 5 H), 8.72-8.78 (m, 1 H), 9.08 (br. s., 1 H) | 353 ([M + H]+) |
| 32 | 1 | 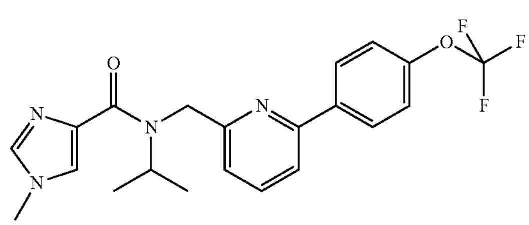 [SMILES: CC(C)N(Cc1cccc(-c2ccc(OC(F)(F)F)cc2)n1)C(=O)c1cn(C)cn1] | 2HCl | | 419 ([M + H]+) |
| 33 | 1 | 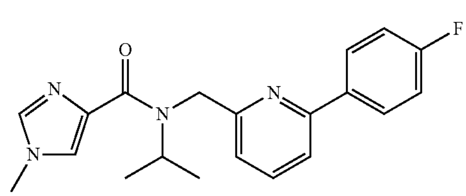 [SMILES: CC(C)N(Cc1cccc(-c2ccc(F)cc2)n1)C(=O)c1cn(C)cn1] | 2HCl | | 353 ([M + H]+) |

TABLE 1-4

| Compound | Example | Structure | Salt | NMR | (ESI pos.) m/z (ESI neg.) m/z |
|---|---|---|---|---|---|
| 34 | 1 | 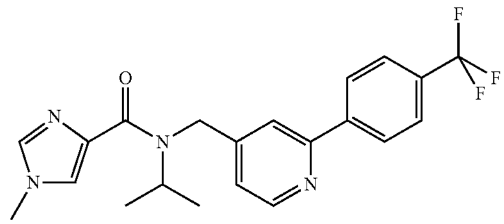 [SMILES: CC(C)N(Cc1ccnc(-c2ccc(C(F)(F)F)cc2)c1)C(=O)c1cn(C)cn1] | 2HCl | 1H NMR (600 MHz, METHANOL-d3) d ppm 1.18-1.45 (m, 6 H), 3.98 (br. s., 3 H), 4.75-5.02 (m, 3 H), 7.57-8.18 (m, 7 H), 8.66-8.72 (m, 1 H), 8.85 (br. s., 1 H) | 403 ([M + H]+) |
| 35 | 1 | 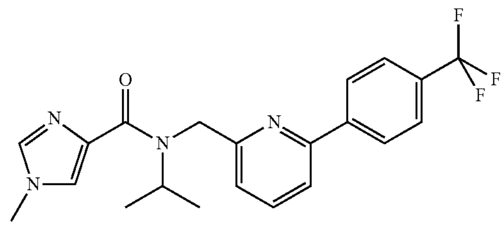 [SMILES: CC(C)N(Cc1cccc(-c2ccc(C(F)(F)F)cc2)n1)C(=O)c1cn(C)cn1] | 2HCl | | 403 ([M + H]+) |
| 36 | 1 | 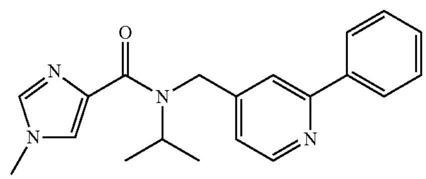 [SMILES: CC(C)N(Cc1ccnc(-c2ccccc2)c1)C(=O)c1cn(C)cn1] | | 1H NMR (600 MHz, CHLOROFORM-d) d ppm 1.10-1.43 (m, 6 H), 3.56-3.84 (m, 3 H), 4.61-5.91 (m, 3 H), 7.10-7.69 (m, 7 H), 7.91-7.99 (m, 2 H), 8.54-8.61 (m, 1 H) | 335 ([M + H]+) |
| 37 | 1 | 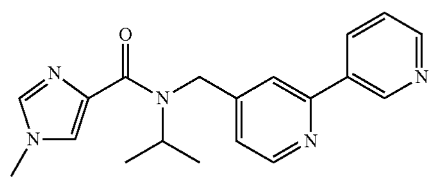 [SMILES: CC(C)N(Cc1ccnc(-c2cccnc2)c1)C(=O)c1cn(C)cn1] | | 1H NMR (600 MHz, CHLOROFORM-d) d ppm 1.08-1.42 (m, 6 H), 3.60-3.84 (m, 3 H), 4.58-5.94 (m, 3 H), 7.15-7.70 (m, 5 H), 8.24-8.33 (m, 1 H), 8.56-8.66 (m, 2 H), 9.14 (br. s., 1 H) | 336 ([M + H]+) |
| 38 | 1 | 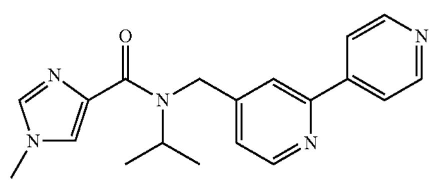 [SMILES: CC(C)N(Cc1ccnc(-c2ccncc2)c1)C(=O)c1cn(C)cn1] | | | 336 ([M + H]+) |
| 39 | 1 | 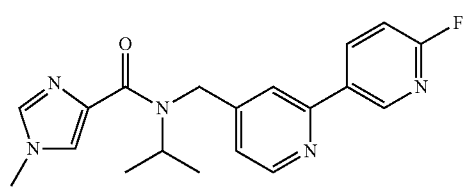 | | 1H NMR (600 MHz, CHLOROFORM-d) d ppm 1.08-1.39 (m, 6 H), 3.59-3.83 (m, 3 H), 4.59-5.91 (m, 3 H), 6.97-7.67 (m, 5 H), 8.36-8.45 (m, 1 H), 8.54-8.62 (m, 1 H), 8.73 (br. s., 1 H) | 354 ([M + H]+) |
| 40 | 1 | 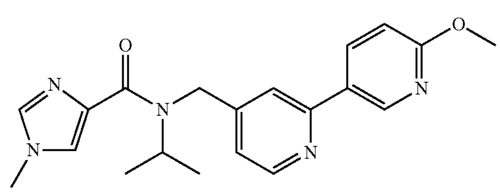 | | 1H NMR (600 MHz, CHLOROFORM-d) d ppm 1.03-1.37 (m, 6 H), 3.58-3.85 (m, 3 H), 3.98 (s, 3 H), 4.58-5.92 (m, 3 H), 6.81 (d, J = 8.7 Hz, 1 H), 7.09-7.64 (m, 4 H), 8.16-8.26 (m, 1 H), 8.50-8.58 (m, 1 H), 8.69 (br. s., 1 H) | 366 ([M + H]+) |
| 41 | 1 | 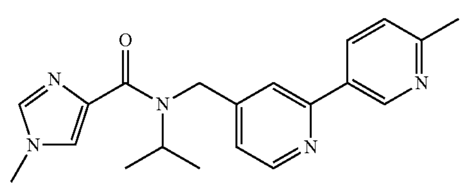 | | | 350 ([M + H ]+) |

TABLE 1-4-continued

| Compound | Example | Structure | Salt | NMR | (ESI pos.) m/z (ESI neg.) m/z |
|---|---|---|---|---|---|
| 42 | 8 | 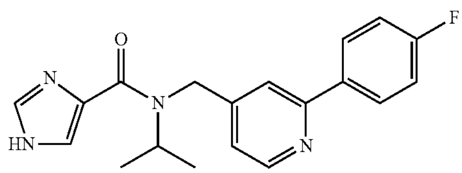 [SMILES: CC(C)N(Cc1ccnc(-c2ccc(F)cc2)c1)C(=O)c1c[nH]cn1] | 2HCl | | 339 ([M + H]+) |
| 43 | 2 | 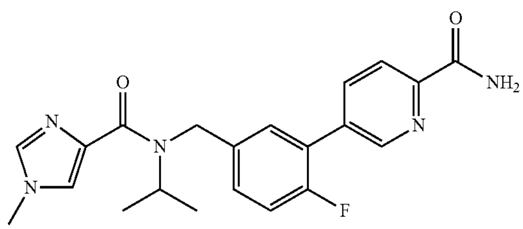 [SMILES: CC(C)N(Cc1ccc(F)c(-c2ccc(C(N)=O)nc2)c1)C(=O)c1cn(C)cn1] | | | 396 ([M + H]+) |
| 44 | 10 | 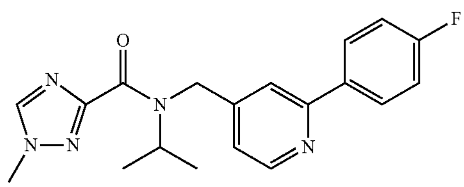 [SMILES: CC(C)N(Cc1ccnc(-c2ccc(F)cc2)c1)C(=O)c1ncn(C)n1] | | | 354 ([M + H]+) |

TABLE 1-5

| Compound | Example | Structure | Salt | NMR | (ESI pos.) m/z (ESI neg.) m/z |
|---|---|---|---|---|---|
| 45 | 5 | 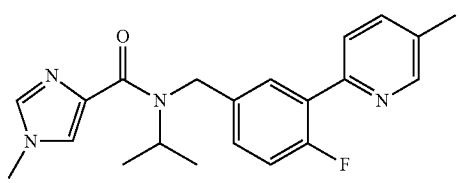 | 2HCl | | 367 ([M + H]+) |
| 46 | 5 | 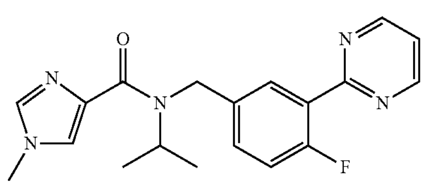 [SMILES: CC(C)N(Cc1ccc(F)c(-c2ncccn2)c1)C(=O)c1cn(C)cn1] | 1HCl | | 354 ([M + H]+) |
| 47 | 5 | 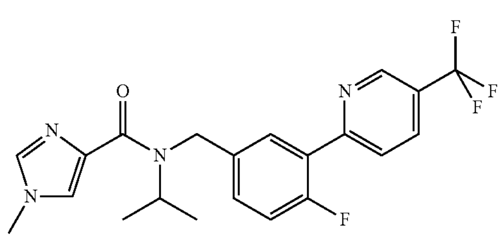 [SMILES: CC(C)N(Cc1ccc(F)c(-c2ccc(C(F)(F)F)cn2)c1)C(=O)c1cn(C)cn1] | | | 421 ([M + H]+) |

TABLE 1-5-continued

| Compound | Example | Structure | Salt | NMR | (ESI pos.) m/z (ESI neg.) m/z |
|---|---|---|---|---|---|
| 48 | 5 | 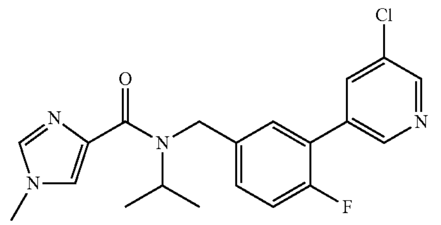 | | | 387 ([M + H]+) |
| 49 | 1 | 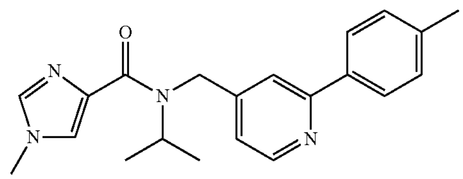 | | 1H NMR (600 MHz, CHLOROFORM-d) d ppm 1.08-1.36 (m, 6 H), 2.39 (s, 3 H), 3.59-3.81 (m, 3 H), 4.61-5.87 (m, 3 H), 7.08-7.89 (m, 8 H), 8.55 (br. s., 1 H) | 349 ([M + H]+) |
| 50 | 1 | 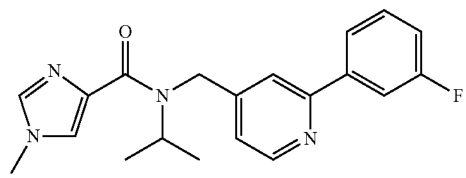 [SMILES: CC(C)N(Cc1ccnc(-c2cccc(F)c2)c1)C(=O)c1cn(C)cn1] | | 1H NMR (600 MHz, CHLOROFORM-d) d ppm 1.09-1.39 (m, 6 H), 3.57-3.83 (m, 3 H), 4.58-5.95 (m, 3 H), 7.03-7.78 (m, 8 H), 8.52-8.61 (m, 1 H) | 353 ([M + H]+) |
| 51 | 1 | 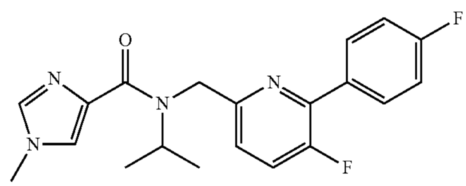 [SMILES: CC(C)N(Cc1ccc(F)c(-c2ccc(F)cc2)n1)C(=O)c1cn(C)cn1] | | | 371 ([M + H]+) |
| 52 | 2 | 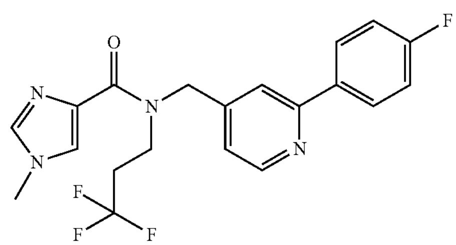 [SMILES: Cn1cnc(C(=O)N(CCC(F)(F)F)Cc2ccnc(-c3ccc(F)cc3)c2)c1] | | | 407 ([M + H]+) |
| 53 | 2 | 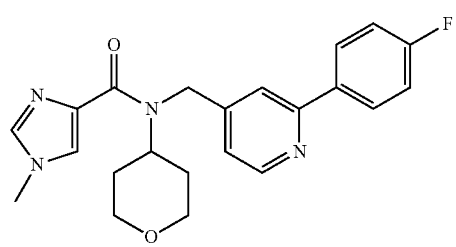 [SMILES: Cn1cnc(C(=O)N(Cc2ccnc(-c3ccc(F)cc3)c2)C2CCOCC2)c1] | | 1H NMR (600 MHz, METHANOL-d3) d ppm 1.52-1.86 (m, 4 H), 3.15-5.46 (m, 10 H), 7.05-7.93 (m, 8 H), 8.41 (d, J = 5.0 Hz, 1 H) | 395 ([M + H]+) |
| 54 | 2 | 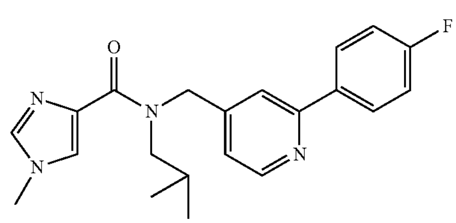 [SMILES: CC(C)CN(Cc1ccnc(-c2ccc(F)cc2)c1)C(=O)c1cn(C)cn1] | | 1H NMR (600 MHz, METHANOL-d3) d ppm 0.67-0.98 (m, 6 H) 1.85-2.13 (m, 1 H) 3.15-5.46 (m, 7 H) 7.03-7.97 (m, 8 H) 8.36-8.55 (m, 1 H) | 367 ([M + H]+) |

TABLE 1-5-continued

| Compound | Example | Structure | Salt | NMR | (ESI pos.) m/z (ESI neg.) m/z |
|---|---|---|---|---|---|
| 55 | 2 | (structure) | | 1H NMR (600 MHz, METHANOL-d3) d ppm 1.43-1.66 (m, 2 H) 2.00-2.19 (m, 4 H) 3.67 (br. s., 3 H) 4.38-5.48 (m, 3 H) 7.07-7.92 (m, 8 H) 8.42 (d, J = 5.50 Hz, 1 H) | 365 ([M + H]+) |

TABLE 1-6

| Compound | Example | Structure | Salt | NMR | (ESI pos.) m/z (ESI neg.) m/z |
|---|---|---|---|---|---|
| 56 | 10 | (structure) | 2HCl | 1H NMR (600 MHz, METHANOL-d3) d ppm 1.41 (br. s., 6 H), 1.53-1.73 (m, 3 H), 4.22-5.27 (m, 5 H), 7.38-9.24 (m, 9 H) | 367 ([M + H]+) |
| 57 | 3 | (structure) | 1HCl | | 356 ([M + H]+) |
| 58 | 5 | (structure) | 1HCl | | 421 ([M + H]+) |
| 59 | 5 | (structure) | 1HCl | | 382 ([M + H]+) |
| 60 | 5 | (structure) | 1HCl | | 387 ([M + H]+) |
| 61 | 1 | (structure) | | 1H NMR (600 MHz, CHLOROFORM-d) d ppm 1.01-1.43 (m, 6 H), 3.59-3.85 (m, 3 H), 4.56-5.90 (m, 3 H), 7.12-7.87 (m, 7 H), 8.50-8.59 (m, 1 H) | 371 ([M + H]+) |

TABLE 1-6-continued
| Compound | Example | Structure | Salt | NMR | (ESI pos.) m/z (ESI neg.) m/z |
|---|---|---|---|---|---|
| 62 | 1 | 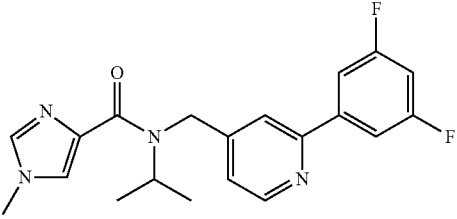 [SMILES: CC(C)N(Cc1ccnc(-c2cc(F)cc(F)c2)c1)C(=O)c1cn(C)cn1] | | 1H NMR (600 MHz, CHLOROFORM-d) d ppm 1.07-1.40 (m, 6 H), 3.57-3.84 (m, 3 H), 4.59-5.90 (m, 3 H), 6.79-6.86 (m, 1 H), 7.15-7.65 (m, 6 H), 8.53-8.61 (m, 1 H) | 371 ([M + H]+) |
| 63 | 2 | 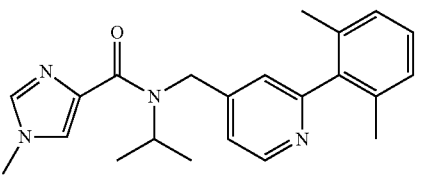 [SMILES: Cc1cccc(C)c1-c1cc(CN(C(=O)c2cn(C)cn2)C(C)C)ccn1] | 2HCl | | 363 ([M + H]+) |
| 64 | 2 | 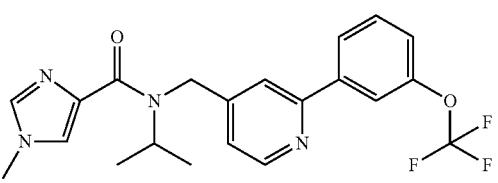 [SMILES: CC(C)N(Cc1ccnc(-c2cccc(OC(F)(F)F)c2)c1)C(=O)c1cn(C)cn1] | 2HCl | 1H NMR (600 MHz, DMSO-d6) d ppm 1.01-1.33 (m, 6 H), 3.60-5.20 (m, 6 H), 7.15-9.14 (m, 9 H) | 419 ([M + H]+) |
| 65 | 2 | 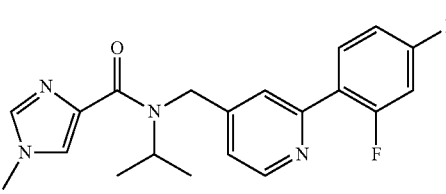 | 2HCl | 1H NMR (600 MHz, DMSO-d6) d ppm 1.01-1.38 (m, 6 H), 3.03-5.19 (m, 6 H), 7.07-9.06 (m, 8 H) | 371 ([M + H]+) |
| 66 | 2 | 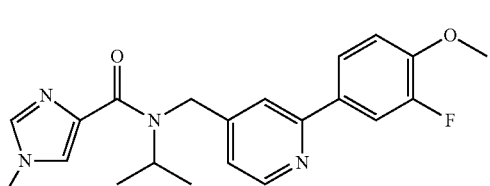 | 2HCl | | 383 ([M + H]+) |
TABLE 1-7
| Compound | Example | Structure | Salt | NMR | (ESI pos.) m/z (ESI neg.) m/z |
|---|---|---|---|---|---|
| 67 | 2 | 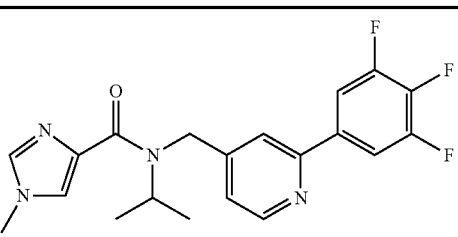 | | 1H NMR (600 MHz, DMSO-d6) d ppm 0.91-1.25 (m, 6 H), 3.53-3.80 (m, 3 H), 4.48-5.80 (m, 3 H), 7.11-8.67 (m, 7 H) | 389([M + H]+) |
| 68 | 2 | 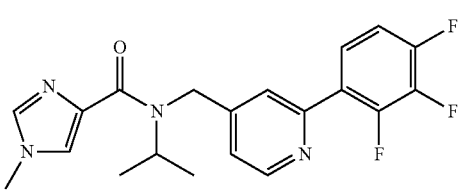 [SMILES: CC(C)N(Cc1ccnc(-c2ccc(F)c(F)c2F)c1)C(=O)c1cn(C)cn1] | 2HCl | 1H NMR (600 MHz, DMSO-d6) d ppm 0.98-1.38 (m, 6 H), 3.60-5.27 (m, 6 H), 7.28-9.15 (m, 7 H) | 389([M + H]+) |

TABLE 1-7-continued

| Compound | Example | Structure | Salt | NMR | (ESI pos.) m/z (ESI neg.) m/z |
|---|---|---|---|---|---|
| 69 | 2 | 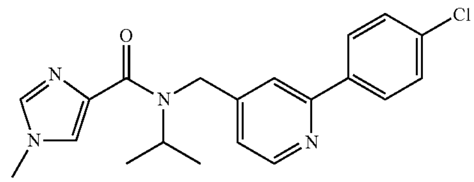 [SMILES: CC(C)N(Cc1ccnc(-c2ccc(Cl)cc2)c1)C(=O)c1cn(C)cn1] | 2HCl | 1H NMR (600 MHz, DMSO-d6) d ppm 1.03-1.35 (m, 6 H), 3.54-5.20 (m, 6 H), 7.27-9.08 (m, 9 H) | 369([M + H]+) |
| 70 | 2 | 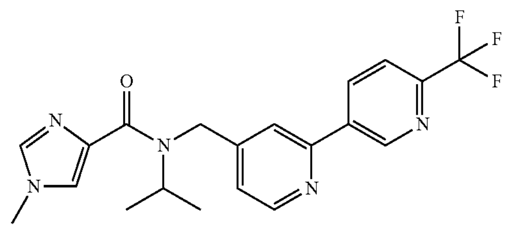 [SMILES: CC(C)N(Cc1ccnc(-c2ccc(C(F)(F)F)nc2)c1)C(=O)c1cn(C)cn1] | | 1H NMR (600 MHz, CHLOROFORM-d) d ppm 1.03-1.45 (m, 6 H), 3.59-3.83 (m, 3 H), 4.57-5.93 (m, 3 H), 7.15-7.50 (m, 2 H), 7.52-7.67 (m, 1 H), 7.70-7.84 (m, 2 H), 8.43-8.53 (m, 1 H), 8.64 (d, J = 5.0 Hz, 1 H), 9.24 (br. s., 1 H) | 404([M + H]+) |
| 71 | 5 | 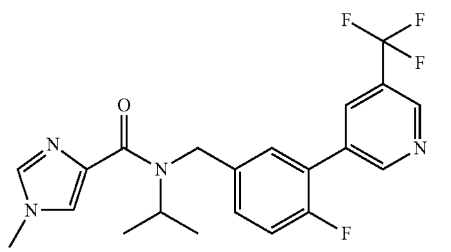 [SMILES: CC(C)N(Cc1ccc(F)c(-c2cncc(C(F)(F)F)c2)c1)C(=O)c1cn(C)cn1] | | | 421([M + H]+) |
| 72 | 5 | 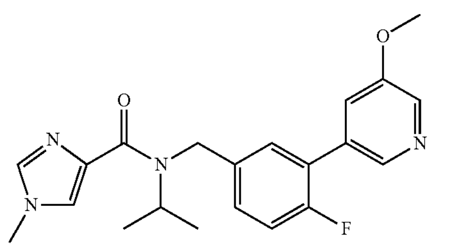 | | | 383([M + H]+) |
| 73 | 12 | 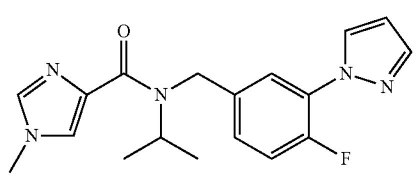 [SMILES: CC(C)N(Cc1ccc(F)c(-n2cccn2)c1)C(=O)c1cn(C)cn1] | 1HCl | 1H NMR (600 MHz, DMSO-d6) d ppm 0.93-1.37 (m, 6 H), 3.57-4.03 (m, 3 H), 4.32-5.14 (m, 3 H), 6.46-8.97 (m, 8 H) | 342([M + H]+) |
| 74 | 12 | 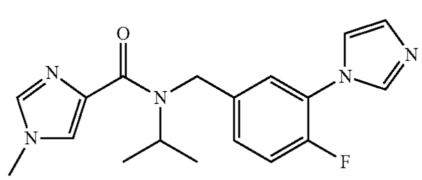 [SMILES: CC(C)N(Cc1ccc(F)c(-n2ccnc2)c1)C(=O)c1cn(C)cn1] | 2HCl | 1H NMR (600 MHz, DMSO-d6) d ppm 0.97-1.35 (m, 6 H), 3.53-5.24 (m, 6 H), 7.40-9.60 (m, 8 H) | 342([M + H]+) |
| 75 | 2 | 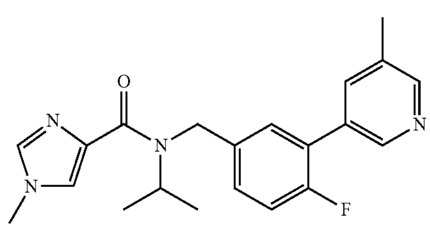 [SMILES: Cc1cncc(-c2cc(CN(C(=O)c3cn(C)cn3)C(C)C)ccc2F)c1] | 2HCl | | 367([M + H]+) |

TABLE 1-7-continued

| Compound | Example | Structure | Salt | NMR | (ESI pos.) m/z (ESI neg.) m/z |
|---|---|---|---|---|---|
| 76 | 5 | 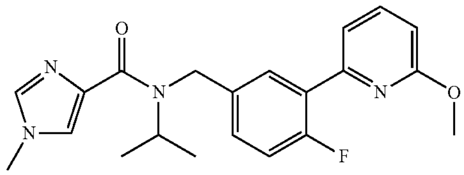 | 2HCl | | 383([M + H]+) |
| 77 | 2 | 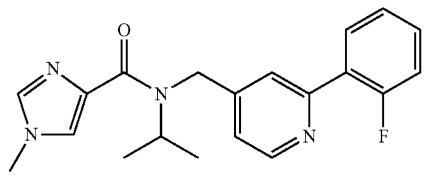 [SMILES: CC(C)N(Cc1ccnc(-c2ccccc2F)c1)C(=O)c1cn(C)cn1] | 2HCl | 1H NMR (600 MHz, METHANOL-d3) d ppm 1.17-1.50 (m, 6 H), 3.78-4.10 (m, 3 H), 4.71-5.10 (m, 3 H), 7.36-8.20 (m, 7 H), 8.74-8.99 (m, 2 H) | 353([M + H]+) |

TABLE 1-8

| Compound | Example | Structure | Salt | NMR | (ESI pos.) m/z (ESI neg.) m/z |
|---|---|---|---|---|---|
| 78 | 2 | 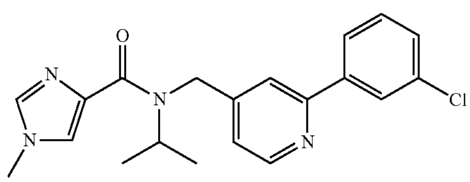 [SMILES: CC(C)N(Cc1ccnc(-c2cccc(Cl)c2)c1)C(=O)c1cn(C)cn1] | 2HCl | 1H NMR (600 MHz, METHANOL-d3) d ppm 1.21-1.51 (m, 6 H), 4.00 (br. s., 3 H), 4.70-5.07 (m, 3 H), 7.59-8.20 (m, 7 H), 8.69-8.99 (m, 2 H) | 369([M + H]+) |
| 79 | 2 | 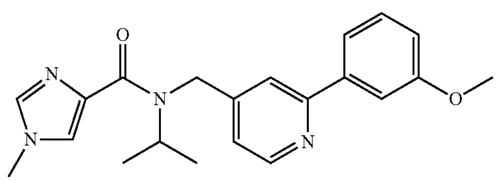 | 2HCl | 1H NMR (600 MHz, METHANOL-d3) d ppm 1.18-1.49 (m, 6 H), 3.83-4.04 (m, 3 H), 3.91 (s, 3 H), 4.69-5.07 (m, 3 H), 7.17-8.71 (m, 9 H) | 365([M + H]+) |
| 80 | 2 | 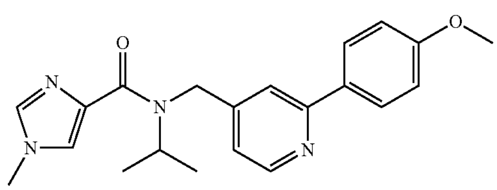 | 2HCl | 1H NMR (600 MHz, METHANOL-d3) d ppm 1.15-1.36 (m, 6 H), 3.80 (br. s., 3 H), 3.89 (s, 3 H), 4.71-5.44 (m, 3 H), 7.10-7.15 (m, 2 H), 7.48-8.02 (m, 6 H), 8.50-8.57 (m, 1 H) | 365([M + H]+) |
| 81 | 2 | 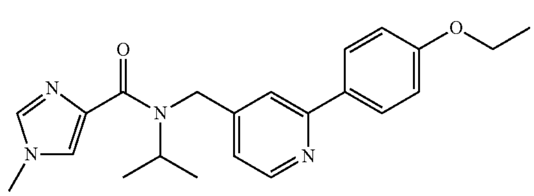 [SMILES: CCOc1ccc(-c2cc(CN(C(=O)c3cn(C)cn3)C(C)C)ccn2)cc1] | 2HCl | 1H NMR (600 MHz, METHANOL-d3) d ppm 1.24-1.40 (m, 6 H), 1.44 (t, J = 7.1 Hz, 3 H), 3.95 (br. s., 3 H), 4.17 (q, J = 6.9 Hz, 2 H), 4.74-5.02 (m, 3 H), 7.16-7.21 (m, 2 H), 7.78-8.19 (m, 5 H), 8.57-8.68 (m, 2 H) | 379([M + H]+) |
| 82 | 2 | 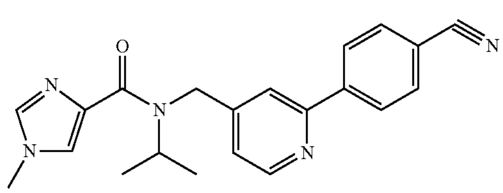 [SMILES: CC(C)N(Cc1ccnc(-c2ccc(C#N)cc2)c1)C(=O)c1cn(C)cn1] | 2HCl | 1H NMR (600 MHz, METHANOL-d3) d ppm 1.18-1.46 (m, 6 H), 4.00 (br. s., 3 H), 4.68-5.10 (m, 3 H), 7.48-8.19 (m, 7 H), 8.66-9.01 (m, 2 H) | 360([M + H]+) |

TABLE 1-8-continued

| Compound | Example | Structure | Salt | NMR | (ESI pos.) m/z (ESI neg.) m/z |
|---|---|---|---|---|---|
| 83 | 2 | 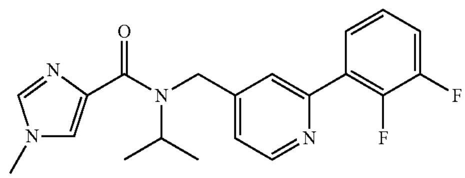 [SMILES: CC(C)N(Cc1ccnc(-c2cccc(F)c2F)c1)C(=O)c1cn(C)cn1] | 2HCl | 1H NMR (600 MHz, METHANOL-d3) d ppm 1.18-1.52 (m, 6 H), 4.00 (br. s., 3 H), 4.67-5.15 (m, 3 H), 7.38-8.23 (m, 6 H), 8.75-9.06 (m, 2 H) | 371([M + H]+) |
| 84 | 2 | 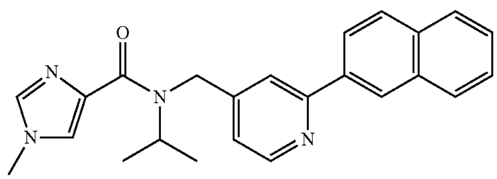 [SMILES: CC(C)N(Cc1ccnc(-c2ccc3ccccc3c2)c1)C(=O)c1cn(C)cn1] | 2HCl | 1H NMR (600 MHz, METHANOL-d3) d ppm 1.22-1.48 (m, 6 H), 3.96 (br. s., 3 H), 4.76-5.10 (m, 3 H), 7.63-7.70 (m, 2 H), 7.80-8.76 (m, 10 H) | 385([M + H]+) |
| 85 | 12 | 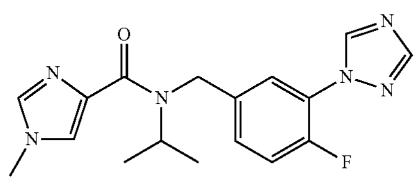 [SMILES: CC(C)N(Cc1ccc(F)c(-n2cncn2)c1)C(=O)c1cn(C)cn1] | 1HCl | | 343([M + H]+) |
| 86 | 5 | 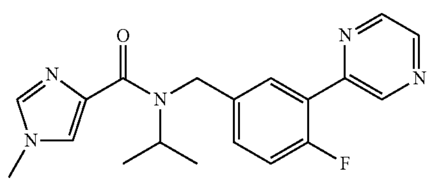 [SMILES: CC(C)N(Cc1ccc(F)c(-c2cnccn2)c1)C(=O)c1cn(C)cn1] | 1HCl | | 354([M + H]+) |
| 87 | 5 | 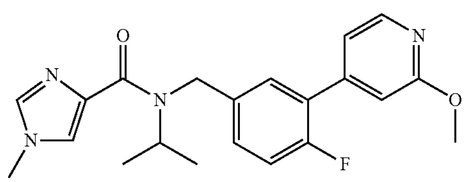 | 2HCl | | 383([M + H]+) |
| 88 | 5 | 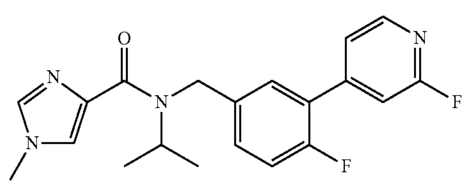 [SMILES: CC(C)N(Cc1ccc(F)c(-c2ccnc(F)c2)c1)C(=O)c1cn(C)cn1] | 1HCl | 1H NMR (600 MHz, METHANOL-d3) d ppm 1.28 (br. s., 6 H), 2.41-5.52 (m, 6 H), 6.45-9.11 (m, 8 H) | 371([M + H]+) |

TABLE 1-9

| Compound | Example | Structure | Salt | NMR | (ESI pos.) m/z (ESI neg.) m/z |
|---|---|---|---|---|---|
| 89 | 5 | 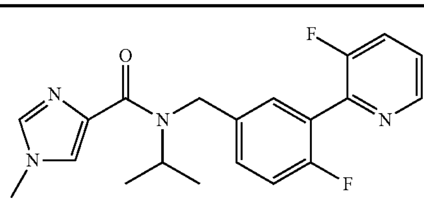 | 1HCl | 1H NMR (600 MHz, METHANOL-d3) d ppm 0.72-1.49 (m, 6 H), 2.37-3.10 (m, 3 H), 3.91 (br. s., 3 H), 6.86-9.01 (m, 8 H) | 371([M + H]+) |

TABLE 1-9-continued

| Compound | Example | Structure | Salt | NMR | (ESI pos.) m/z (ESI neg.) m/z |
|---|---|---|---|---|---|
| 90 | 5 | 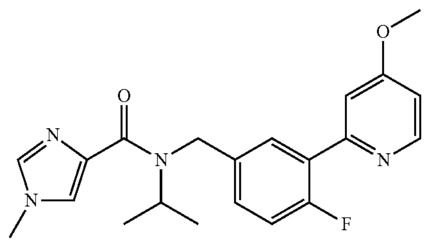 | 2HCl | | 383([M + H]+) |
| 91 | 2 | 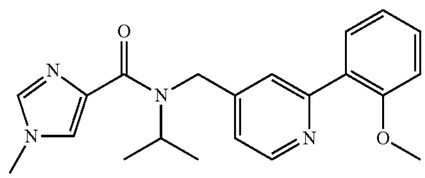 | 2HCl | | 365([M + H]+) |
| 92 | 2 | 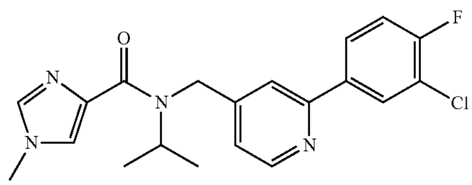 [SMILES: CC(C)N(Cc1ccnc(-c2ccc(F)c(Cl)c2)c1)C(=O)c1cn(C)cn1] | 2HCl | 1H NMR (600 MHz, METHANOL-d3) d ppm 1.24-1.50 (m, 6 H), 4.03 (br. s., 3 H), 4.64-5.15 (m, 3 H), 7.58 (t, J = 8.7 Hz, 1 H), 7.90-8.29 (m, 5 H), 8.74-8.79 (m, 1 H), 9.07 (br. s., 1 H) | 387([M + H]+) |
| 93 | 2 | 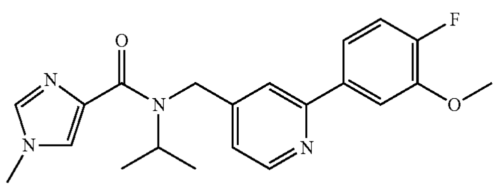 | 2HCl | | 383([M + H]+) |
| 94 | 2 | 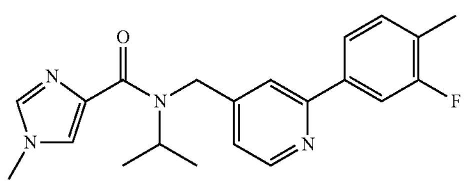 [SMILES: Cc1ccc(-c2cc(CN(C(=O)c3cn(C)cn3)C(C)C)ccn2)cc1F] | 2HCl | 1H NMR (600 MHz, METHANOL-d3) d ppm 1.25-1.50 (m, 6 H), 2.41 (s, 3 H), 4.03 (br. s., 3 H), 4.64-5.16 (m, 3 H), 7.54-8.30 (m, 6 H), 8.70-8.77 (m, 1 H), 9.06 (br. s., 1 H) | 367([M + H]+) |
| 95 | 2 | 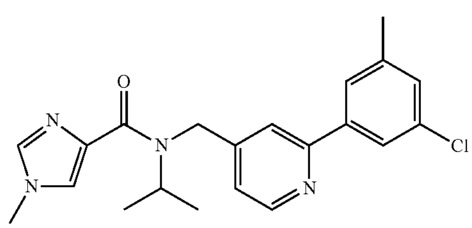 [SMILES: Cc1cc(Cl)cc(-c2cc(CN(C(=O)c3cn(C)cn3)C(C)C)ccn2)c1] | 2HCl | 1H NMR (600 MHz, METHANOL-d3) d ppm 1.24-1.50 (m, 6 H), 2.50 (s, 3 H), 4.03 (br. s., 3 H), 4.66-5.16 (m, 3 H), 7.56-8.32 (m, 6 H), 8.72-8.79 (m, 1 H), 9.08 (br. s., 1 H) | 383([M + H]+) |
| 96 | 2 | 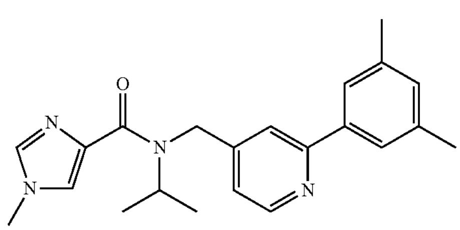 | 2HCl | | 363([M + H]+) |

TABLE 1-9-continued

| Compound | Example | Structure | Salt | NMR | (ESI pos.) m/z (ESI neg.) m/z |
|---|---|---|---|---|---|
| 97 | 5 | 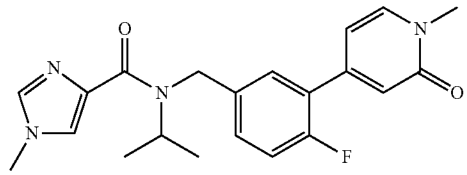 [SMILES: CC(C)N(Cc1ccc(F)c(-c2ccn(C)c(=O)c2)c1)C(=O)c1cn(C)cn1] | | | 383([M + H]+) |
| 98 | 2 | 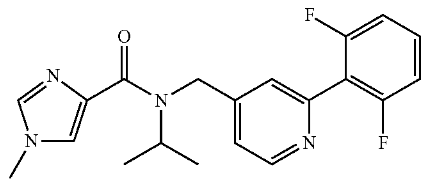 [SMILES: CC(C)N(Cc1ccnc(-c2c(F)cccc2F)c1)C(=O)c1cn(C)cn1] | 2HCl | | 371([M + H]+) |
| 99 | 2 | 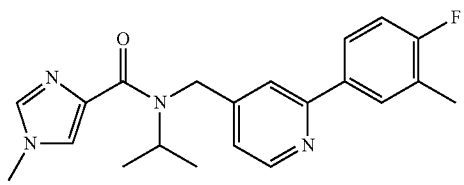 | 2HCl | 1H NMR (600 MHz, DMSO-d6) d ppm 1.04-1.35 (m, 6 H), 2.34 (s, 3 H), 3.31-4.40 (m, 3 H), 4.59-5.19 (m, 3 H), 7.30-7.55 (m, 2 H), 7.90-8.21 (m, 4 H), 8.61-9.04 (m, 2 H) | 367([M + H]+) |

TABLE 1-10

| Compound | Exampl | Structure | Salt | NMR | (ESI pos.) m/z (ESI neg.) m/z |
|---|---|---|---|---|---|
| 100 | 2 | 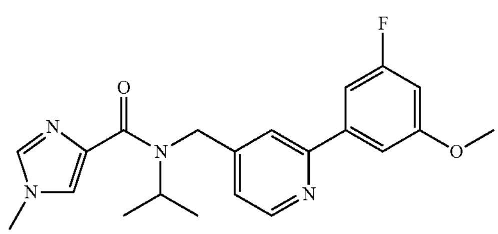 | 2HCl | 1H NMR (600 MHz, DMSO-d6) d ppm 1.03-1.41 (m, 6 H), 3.29-4.33 (m, 3 H), 3.86 (s, 3 H), 4.45-5.24 (m, 3 H), 6.96 (d, J = 10.5 Hz, 1 H), 7.29-8.22 (m, 5 H), 8.56-9.08 (m, 2 H) | 383([M + H]+) |
| 101 | 2 | 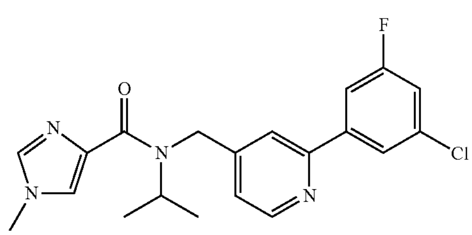 | 2HCl | 1H NMR (600 MHz, DMSO-d6) d ppm 1.03-1.35 (m, 6 H), 3.29-3.95 (m, 3 H), 4.52-5.18 (m, 3 H), 7.31 (d, J = 4.6 Hz, 1 H), 7.54 (dt, J = 8.5, 1.9 Hz, 1 H), 7.85-8.15 (m, 4 H), 8.56-8.95 (m, 2 H) | 387([M + H]+) |
| 102 | 2 | 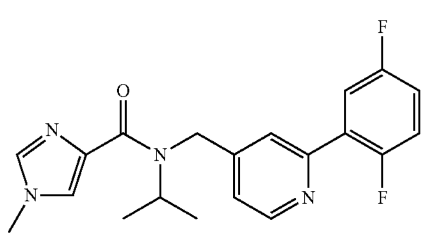 [SMILES: CC(C)N(Cc1ccnc(-c2cc(F)ccc2F)c1)C(=O)c1cn(C)cn1] | 2HCl | 1H NMR (600 MHz, DMSO-d6) d ppm 1.02-1.29 (m, 6 H), 3.41-4.39 (m, 3 H), 4.49-5.08 (m, 3 H), 7.26-9.13 (m, 8 H) | 371([M + H]+) |

TABLE 1-10-continued

| Compound | Exampl | Structure | Salt | NMR | (ESI pos.) m/z (ESI neg.) m/z |
|---|---|---|---|---|---|
| 103 | 2 | 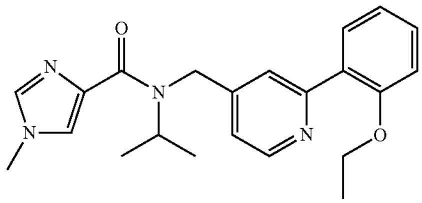 [SMILES: CCOc1ccccc1-c1cc(CN(C(=O)c2cn(C)cn2)C(C)C)ccn1] | | | 379([M + H]+) |
| 104 | 2 | 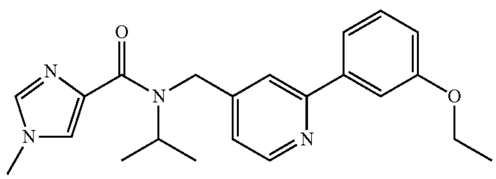 [SMILES: CCOc1cccc(-c2cc(CN(C(=O)c3cn(C)cn3)C(C)C)ccn2)c1] | 2HCl | 1H NMR (600 MHz, DMSO-d6) d ppm 1.06-1.31 (m, 6 H), 1.37 (t, J = 6.9 Hz, 3 H), 3.16-4.41 (m, 3 H), 4.13 (q, J = 7.2 Hz, 2 H), 4.55-5.28 (m, 3 H), 6.97-9.05 (m, 9 H) | 379([M + H]+) |
| 105 | 3 | 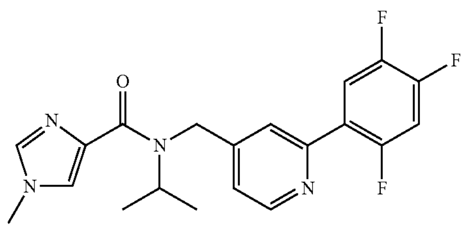 [SMILES: CC(C)N(Cc1ccnc(-c2cc(F)c(F)cc2F)c1)C(=O)c1cn(C)cn1] | | 1H NMR (600 MHz, CHLOROFORM-d) d ppm 1.08-1.35 (m, 6 H), 3.58-3.80 (m, 3 H), 4.58-5.91 (m, 3 H), 6.92-7.95 (m, 6 H), 8.58 (d, J = 4.6 Hz, 1 H) | 389([M + H]+) |
| 106 | 2 | 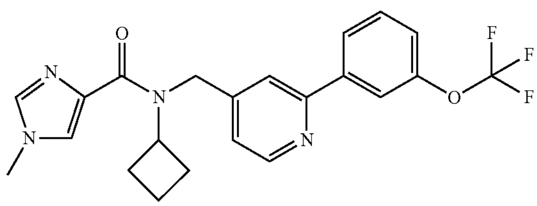 [SMILES: Cn1cnc(C(=O)N(Cc2ccnc(-c3cccc(OC(F)(F)F)c3)c2)C2CCC2)c1] | 2HCl | 1H NMR (600 MHz, METHANOL-d3) d ppm 1.69-1.86 (m, 2 H), 2.20-2.46 (m, 4 H), 4.04 (br. s., 3 H), 4.72-5.32 (m, 3 H), 7.60-8.30 (m, 7 H), 8.72-9.14 (m, 2 H) | 431([M + H]+) |
| 107 | 2 | 383([M + H]+) | 2HCl | 1H NMR (600 MHz, METHANOL-d3) d ppm 1.69-1.84 (m, 2 H), 2.19-2.45 (m, 4 H), 4.04 (br. s., 3 H), 4.68-5.30 (m, 3 H), 7.53-8.30 (m, 7 H), 8.72-9.13 (m, 2 H) | 431([M + H]+) |
| 108 | 2 | 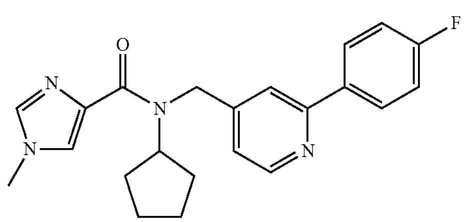 [SMILES: Cn1cnc(C(=O)N(Cc2ccnc(-c3ccc(F)cc3)c2)C2CCCC2)c1] | | 1H NMR (600 MHz, CHLOROFORM-d) d ppm 1.44-2.08 (m, 8 H), 3.54-3.88 (m, 3 H), 4.56-5.95 (m, 3 H), 7.07-7.74 (m, 6 H), 7.87-7.99 (m, 2 H), 8.55 (d, J = 5.0 Hz, 1 H) | 379([M + H]+) |
| 109 | 2 | 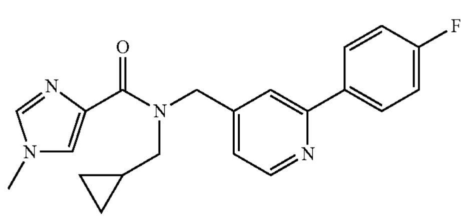 [SMILES: Cn1cnc(C(=O)N(Cc2ccnc(-c3ccc(F)cc3)c2)CC2CC2)c1] | 2HCl | 1H NMR (600 MHz, DMSO-d6) d ppm 0.17-0.30 (m, 2 H), 0.39-0.48 (m, 2 H), 1.03-1.12 (m, 1 H), 2.79-5.38 (m, 7 H), 7.16-9.02 (m, 9 H) | 365([M + H]+) |

TABLE 1-10-continued

| Compound | Exampl | Structure | Salt | NMR | (ESI pos.) m/z (ESI neg.) m/z |
|---|---|---|---|---|---|
| 110 | 5 | 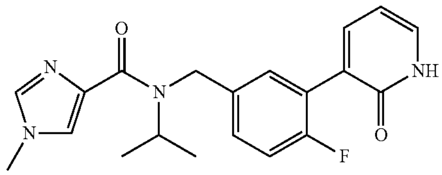 [SMILES: CC(C)N(Cc1ccc(F)c(-c2ccc[nH]c2=O)c1)C(=O)c1cn(C)cn1] | | 1H NMR (600 MHz, CHLOROFORM-d) d ppm 1.03-1.71 (m, 6 H), 3.52-3.85 (m, 3 H), 4.47-5.85 (m, 3 H), 6.30 (t, J = 6.6 Hz, 1 H), 6.88-7.67 (m, 8 H) | 369([M + H]+) |

TABLE 1-11

| Compound | Example | Structure | Salt | NMR | (ESI pos.) m/z (ESI neg.) m/z |
|---|---|---|---|---|---|
| 111 | 2 | 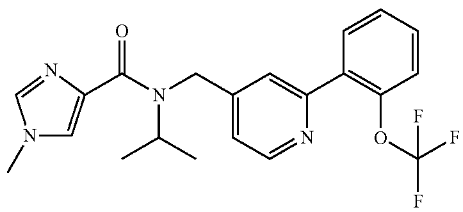 [SMILES: CC(C)N(Cc1ccnc(-c2ccccc2OC(F)(F)F)c1)C(=O)c1cn(C)cn1] | 2HCl | | 419([M + H]+) |
| 112 | 2 | 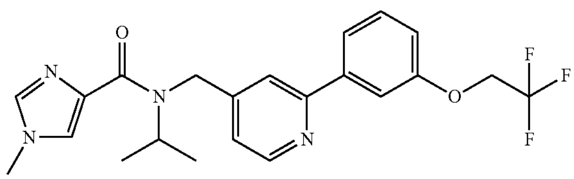 [SMILES: CC(C)N(Cc1ccnc(-c2cccc(OCC(F)(F)F)c2)c1)C(=O)c1cn(C)cn1] | 2HCl | 1H NMR (600 MHz, DMSO-d6) d ppm 1.01-1.36 (m, 6 H), 3.60-3.96 (m, 3 H), 4.59-5.24 (m, 3 H), 4.84-4.91 (m, 2 H), 7.12-8.98 (m, 9 H) | 433([M + H]+) |
| 113 | 3 | 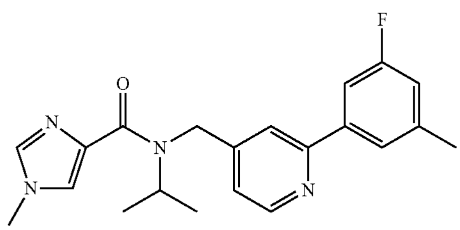 | 2HCl | 1H NMR (600 MHz, DMSO-d6) d ppm 1.05-1.38 (m, 6 H), 2.42 (s, 3 H), 3.67-4.00 (m, 3 H), 4.58-5.13 (m, 3 H), 7.12-8.25 (m, 6 H), 8.58-9.13 (m, 2 H) | 367([M + H]+) |
| 114 | 3 | 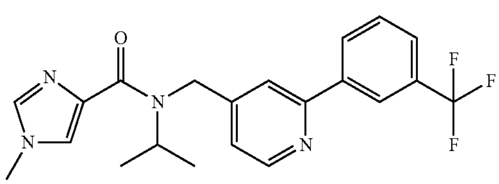 [SMILES: CC(C)N(Cc1ccnc(-c2cccc(C(F)(F)F)c2)c1)C(=O)c1cn(C)cn1] | 2HCl | 1H NMR (600 MHz, DMSO-d6) d ppm 1.02-1.38 (m, 6 H), 3.65-4.00 (m, 3 H), 4.42-5.25 (m, 3 H), 7.38 (br. s., 1 H), 7.68-8.46 (m, 6 H), 8.60-9.12 (m, 2 H) | 403([M + H]+) |
| 115 | 3 | 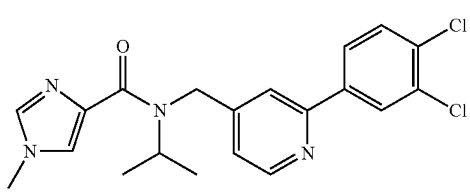 | 2HCl | 1H NMR (600 MHz, DMSO-d6) d ppm 1.04-1.37 (m, 6 H), 3.68-3.99 (m, 3 H), 4.59-5.12 (m, 3 H), 7.31-7.39 (m, 1 H), 7.76-8.34 (m, 5 H), 8.59-9.10 (m, 2 H) | 403([M + H]+) |

TABLE 1-11-continued
| Compound | Example | Structure | Salt | NMR | (ESI pos.) m/z (ESI neg.) m/z |
|---|---|---|---|---|---|
| 116 | 3 | 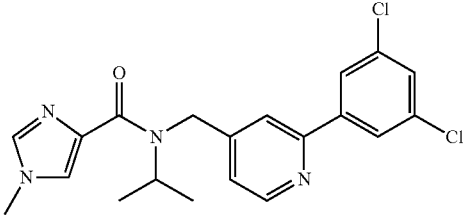 | | 1H NMR (600 MHz, CHLOROFORM-d) d ppm 1.11-1.37 (m, 6 H), 3.60-3.83 (m, 3 H), 4.60-5.91 (m, 3 H), 7.17-7.91 (m, 7 H), 8.54-8.61 (m, 1 H) | 403([M + H]+) 405([M + 3]+) |
| 117 | 3 | 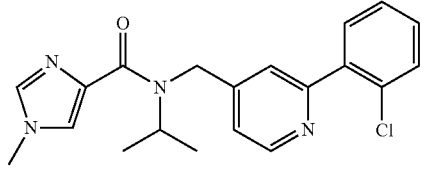 [SMILES: CC(C)N(Cc1ccnc(-c2ccccc2Cl)c1)C(=O)c1cn(C)cn1] | 2HCl | 1H NMR (600 MHz, DMSO-d6) d ppm 1.01-1.38 (m, 6 H), 3.64-3.96 (m, 3 H), 4.61-5.21 (m, 3 H), 7.46-8.20 (m, 7 H), 8.70-9.04 (m, 2 H) | 369([M + H]+) |
| 118 | 2 | 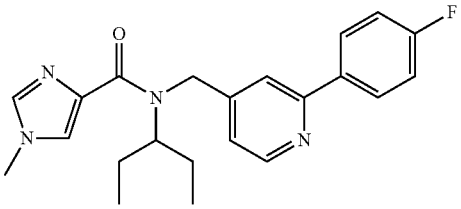 [SMILES: CCC(CC)N(Cc1ccnc(-c2ccc(F)cc2)c1)C(=O)c1cn(C)cn1] | 2HCl | | 381([M + H]+) |
| 119 | 2 | 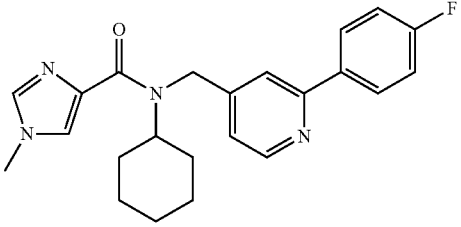 [SMILES: Cn1cnc(C(=O)N(Cc2ccnc(-c3ccc(F)cc3)c2)C2CCCCC2)c1] | 2HCl | 1H NMR (600 MHz, METHANOL-d3) d ppm 1.12-2.02 (m, 10 H), 3.91-4.40 (m, 3 H), 4.71-5.26 (m, 3 H), 7.31-8.23 (m, 7 H), 8.64-9.01 (m, 2 H) | 393([M + H]+) |
| 120 | 5 | 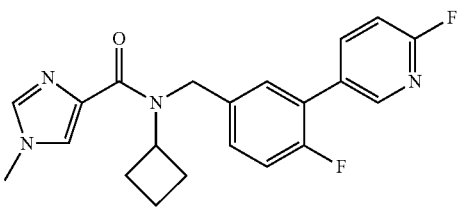 [SMILES: Cn1cnc(C(=O)N(Cc2ccc(F)c(-c3ccc(F)nc3)c2)C2CCC2)c1] | 1HCl | 1H NMR (600 MHz, DMSO-d6) d ppm 1.40-2.28 (m, 6 H), 3.68-4.10 (m, 3 H), 4.87 (br. s., 3 H), 7.13-9.03 (m, 8 H) | 383([M + H]+) |
| 121 | 11 | 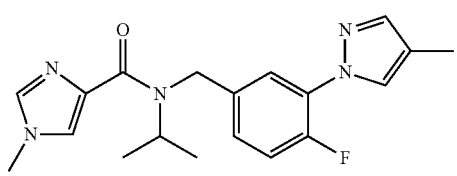 | 1HCl | 1H NMR (600 MHz, DMSO-d6) d ppm 1.05-1.29 (m, 6 H), 2.10 (s, 3 H), 3.18-3.98 (m, 3 H), 4.41-5.15 (m, 3 H), 7.11-8.92 (m, 7 H) | 356([M + H]+) |

TABLE 1-12

| Compound | Example | Structure | Salt | NMR | (ESI pos.) m/z (ESI neg.) m/z |
|---|---|---|---|---|---|
| 122 | 5 | 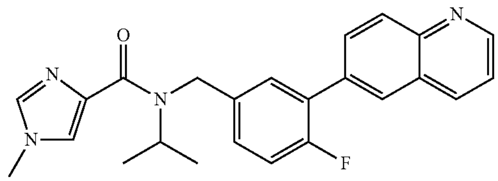 [SMILES: CC(C)N(Cc1ccc(F)c(-c2ccc3ncccc3c2)c1)C(=O)c1cn(C)cn1] | 2HCl | 1H NMR (600 MHz, DMSO-d6) d ppm 1.11-2.14 (m, 6 H), 3.85 (br. s., 3 H), 4.42-5.10 (m, 3 H), 7.28-9.06 (m, 10 H), 9.17 (d, J = 3.7 Hz, 1 H) | 403([M + H]+) |
| 123 | 5 | 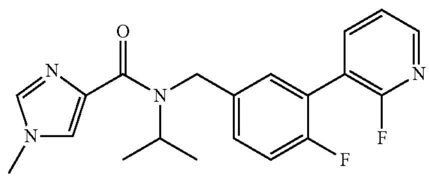 [SMILES: CC(C)N(Cc1ccc(F)c(-c2cccnc2F)c1)C(=O)c1cn(C)cn1] | 1HCl | 1H NMR (600 MHz, DMSO-d6) d ppm 1.06-1.27 (m, 6 H), 2.99-3.94 (m, 3 H), 4.33-5.14 (m, 3 H), 7.19-8.44 (m, 7 H), 8.81 (br. s., 1 H) | 371([M + H]+) |
| 124 | 3 | 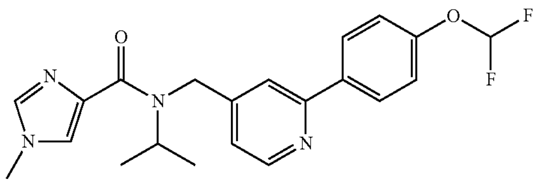 [SMILES: CC(C)N(Cc1ccnc(-c2ccc(OC(F)F)cc2)c1)C(=O)c1cn(C)cn1] | 2HCl | 1H NMR (600 MHz, DMSO-d6) d ppm 1.04-1.38 (m, 6 H), 3.65-3.97 (m, 3 H), 4.56-5.19 (m, 3 H), 7.25 (s, 8 H), 8.58-9.07 (m, 2 H) | 401([M + H]+) |
| 125 | 3 | 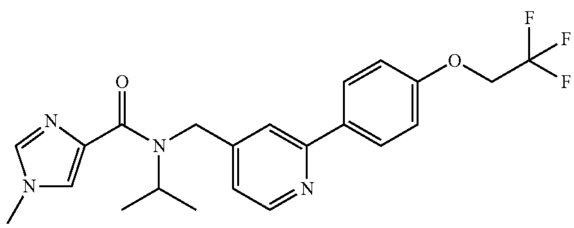 [SMILES: CC(C)N(Cc1ccnc(-c2ccc(OCC(F)(F)F)cc2)c1)C(=O)c1cn(C)cn1] | 2HCl | | 433([M + H]+) |
| 126 | 3 | 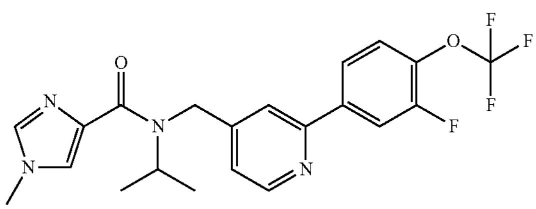 [SMILES: CC(C)N(Cc1ccnc(-c2ccc(OC(F)(F)F)c(F)c2)c1)C(=O)c1cn(C)cn1] | 2HCl | 1H NMR (600 MHz, DMSO-d6) d ppm 1.03-1.40 (m, 6 H), 3.60-4.03 (m, 3 H), 4.14-5.20 (m, 3 H), 7.26-8.30 (m, 6 H), 8.57-9.22 (m, 2 H) | 437([M + H]+) |
| 127 | 3 | 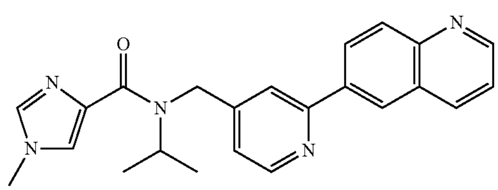 [SMILES: CC(C)N(Cc1ccnc(-c2ccc3ncccc3c2)c1)C(=O)c1cn(C)cn1] | 3HCl | 1H NMR (600 MHz, DMSO-d6) d ppm 1.02-1.47 (m, 6 H), 3.59-5.39 (m, 6 H), 7.38-9.32 (m, 11 H) | 386([M + H]+) |
| 128 | 13 | 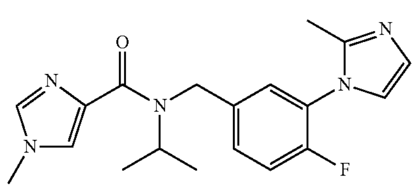 [SMILES: Cc1nccn1-c1cc(CN(C(=O)c2cn(C)cn2)C(C)C)ccc1F] | 2HCl | | 356([M + H]+) |
| 129 | 3 | 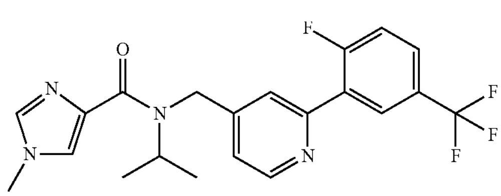 [SMILES: CC(C)N(Cc1ccnc(-c2cc(C(F)(F)F)ccc2F)c1)C(=O)c1cn(C)cn1] | 2HCl | Determined as free form 1H NMR (600 MHz, CHLOROFORM-d) d ppm 1.10-1.35 (m, 6 H), 3.60-3.80 (m, 3 H), 4.55-5.91 (m, 3 H), 7.13-8.69 (m, 8 H) | 421([M + H]+) |

TABLE 1-12-continued

| Compound | Example | Structure | Salt | NMR | (ESI pos.) m/z (ESI neg.) m/z |
|---|---|---|---|---|---|
| 130 | 3 | 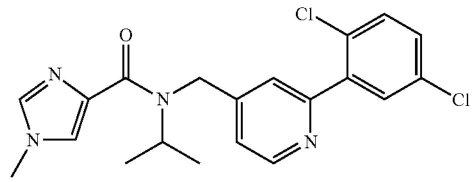 [SMILES: CC(C)N(Cc1ccnc(-c2cc(Cl)ccc2Cl)c1)C(=O)c1cn(C)cn1] | 2HCl | | 403([M + H]+) |
| 131 | 3 | 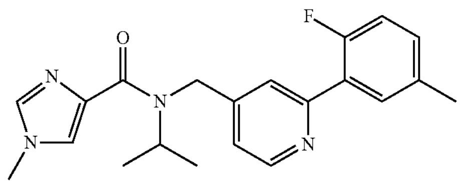 | 2HCl | | 367([M + H]+) |
| 132 | 13 | 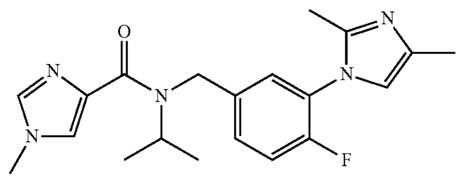 | | | 370([M + H]+) |

TABLE 1-13

| Compound | Example | Structure | Salt | NMR | (ESI pos.) m/z (ESI neg.) m/z |
|---|---|---|---|---|---|
| 133 | 3 | 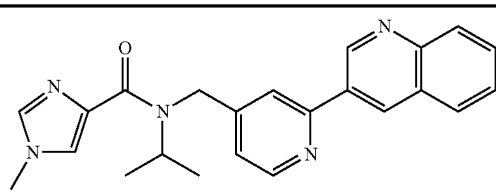 | 3HCl | 1H NMR (600 MHz, DMSO-d6) d ppm 1.02-1.36 (m, 6 H), 3.16-5.22 (m, 6 H), 7.38 (d, J = 4.1 Hz, 1 H), 7.71-8.25 (m, 6 H), 8.66-9.25 (m, 3 H), 9.60-9.72 (m, 1 H) | 386([M + H]+) |
| 134 | 3 | 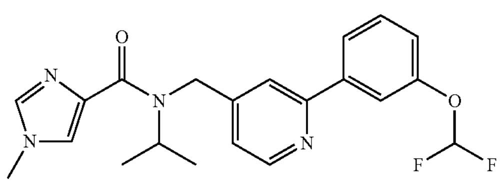 [SMILES: CC(C)N(Cc1ccnc(-c2cccc(OC(F)F)c2)c1)C(=O)c1cn(C)cn1] | 2HCl | 1H NMR (600 MHz, DMSO-d6) d ppm 1.06-1.38 (m, 6 H), 3.64-5.22 (m, 6 H), 7.21-9.12 (m, 10 H) | 401([M + H]+) |
| 135 | 3 | 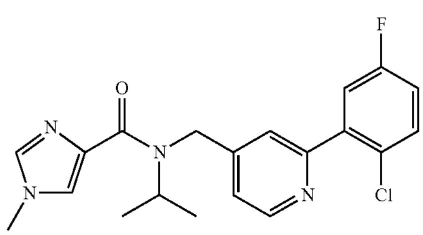 | 2HCl | 1H NMR (600 MHz, DMSO-d6) d ppm 0.96-1.35 (m, 6 H), 3.53-5.27 (m, 6 H), 7.28-9.12 (m, 8 H) | 387([M + H]+) |
| 136 | 3 | 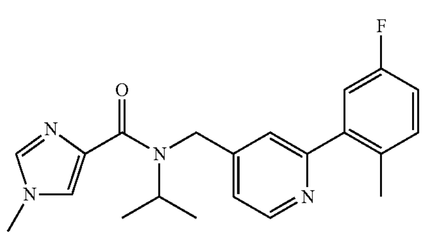 | 2HCl | | 367([M + H]+) |

TABLE 1-13-continued
| Compound | Example | Structure | Salt | NMR | (ESI pos.) m/z (ESI neg.) m/z |
|---|---|---|---|---|---|
| 137 | 3 | 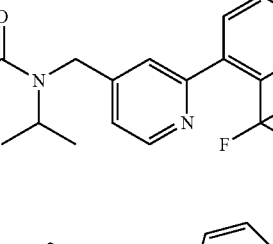 | 2HCl | | 421([M + H]+) |
| 138 | 8 | 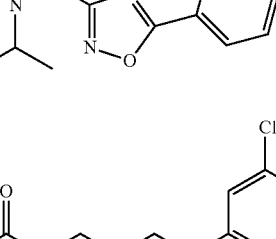 | | | 360([M + H]+) |
| 139 | 3 | 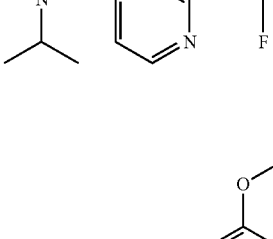 | 2HCl | 1H NMR (600 MHz, DMSO-d6) d ppm 0.99-1.35 (m, 6 H), 3.60-5.18 (m, 6 H), 7.31-8.18 (m, 6 H), 8.57-9.00 (m, 2 H) | 387([M + H]+) |
| 140 | 3 | 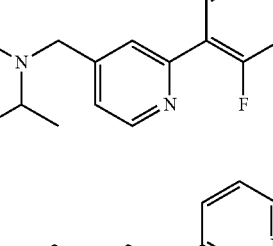 | 2HCl | | 437([M + H]+) |
| 141 | 2 | 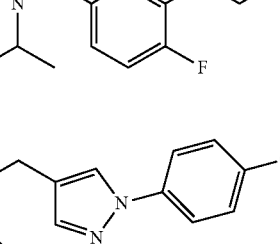 | 1HCl | | 357([M + H]+) |
| 142 | 8 | 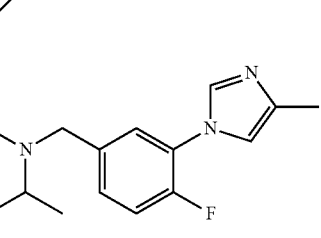 | | | 420([M + H]+) |
| 143 | 13 | 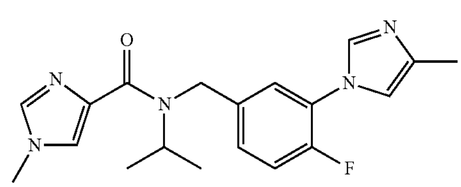 | 2HCl | 1H NMR (600 MHz, DMSO-d6) d ppm 1.17 (br. s., 6 H), 2.35 (s, 3 H), 3.23-4.16 (m, 3 H), 4.43-5.38 (m, 3 H), 7.39-8.73 (m, 6 H), 9.42 (br. s., 1 H) | 356([M + H]+) |

TABLE 1-14

| Compound | Example | Structure | Salt | NMR | (ESI pos.) m/z (ESI neg.) m/z |
|---|---|---|---|---|---|
| 144 | 5 | 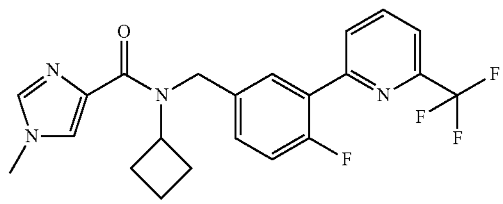 [SMILES: Cn1cnc(C(=O)N(Cc2ccc(F)c(-c3cccc(C(F)(F)F)n3)c2)C2CCC2)c1] | 1HCl | 1H NMR (600 MHz, DMSO-d6) d ppm 1.39-2.31 (m, 6 H), 3.76 (br. s., 3 H), 4.18-5.56 (m, 3 H), 7.20-8.29 (m, 8 H) | 433([M + H]+) |
| 145 | 5 | 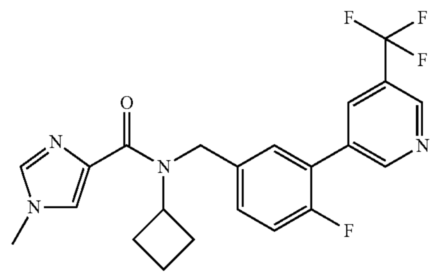 [SMILES: Cn1cnc(C(=O)N(Cc2ccc(F)c(-c3cncc(C(F)(F)F)c3)c2)C2CCC2)c1] | 2HCl | 1H NMR (600 MHz, DMSO-d6) d ppm 1.41-2.33 (m, 6 H), 3.83 (br. s., 3 H), 4.47-5.81 (m, 3 H), 7.06-9.14 (m, 8 H) | 433([M + H]+) |
| 146 | 3 | 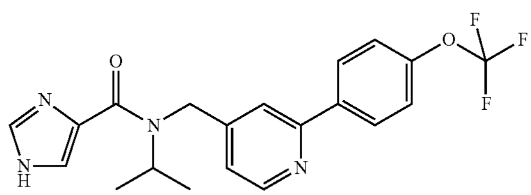 [SMILES: CC(C)N(Cc1ccnc(-c2ccc(OC(F)(F)F)cc2)c1)C(=O)c1c[nH]cn1] | 2HCl | | 405([M + H]+) |
| 147 | 2 | 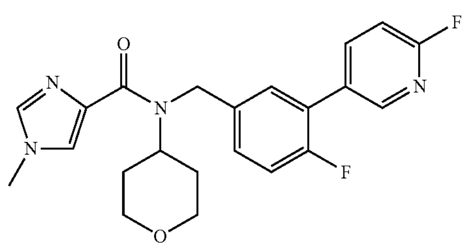 [SMILES: Cn1cnc(C(=O)N(Cc2ccc(F)c(-c3ccc(F)nc3)c2)C2CCOCC2)c1] | 1HCl | 1H NMR (600 MHz, DMSO-d6) d ppm 1.41-1.90 (m, 4 H), 3.13-5.20 (m, 10 H), 7.22-8.84 (m, 8 H) | 413([M + H]+) |
| 148 | 2 | 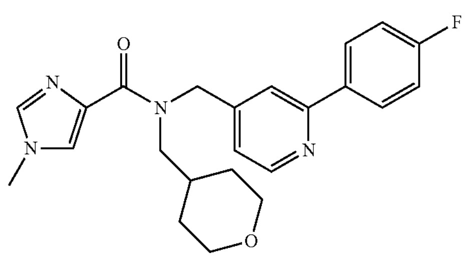 [SMILES: Cn1cnc(C(=O)N(Cc2ccnc(-c3ccc(F)cc3)c2)CC2CCOCC2)c1] | 2HCl | | 409([M + H]+) |
| 149 | 2 | 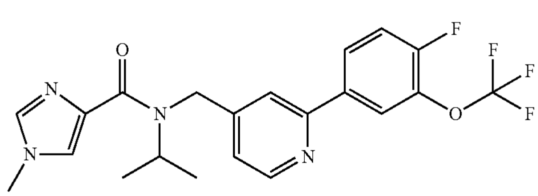 [SMILES: CC(C)N(Cc1ccnc(-c2ccc(F)c(OC(F)(F)F)c2)c1)C(=O)c1cn(C)cn1] | 2HCl | 1H NMR (600 MHz, DMSO-d6) d ppm 1.05-1.37 (m, 6 H), 3.63-5.22 (m, 6 H), 7.21-7.43 (m, 1 H), 7.56-8.31 (m, 5 H), 8.54-9.15 (m, 2 H) | 437([M + H]+) |
| 150 | 2 | 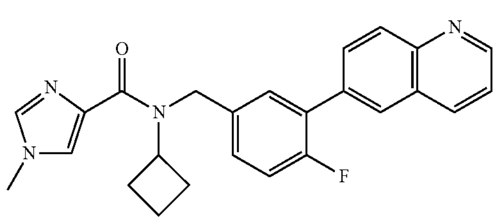 [SMILES: Cn1cnc(C(=O)N(Cc2ccc(F)c(-c3ccc4ncccc4c3)c2)C2CCC2)c1] | 2HCl | 1H NMR (600 MHz, DMSO-d6) d ppm 1.50-1.68 (m, 2 H), 2.05-2.31 (m, 4 H), 3.52-5.23 (m, 6 H), 7.24-8.40 (m, 8 H), 8.75-9.21 (m, 3 H) | 415([M + H]+) |

TABLE 1-14-continued

| Compound | Example | Structure | Salt | NMR | (ESI pos.) m/z (ESI neg.) m/z |
|---|---|---|---|---|---|
| 151 | 5 | 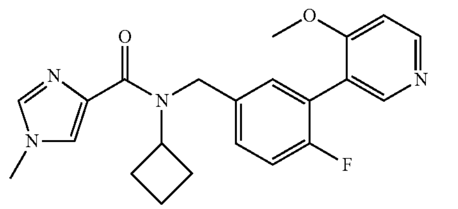 [SMILES: COc1ccncc1-c1cc(CN(C(=O)c2cn(C)cn2)C2CCC2)ccc1F] | 2HCl | | 395([M + H]+) |
| 152 | 5 | 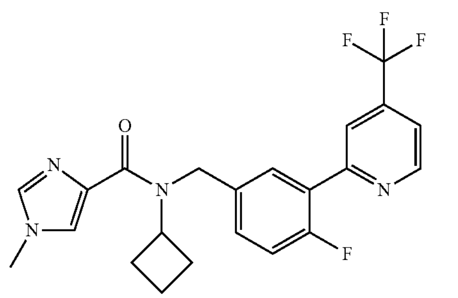 [SMILES: Cn1cnc(C(=O)N(Cc2ccc(F)c(-c3cc(C(F)(F)F)ccn3)c2)C2CCC2)c1] | 1HCl | 1H NMR (600 MHz, DMSO-d6) d ppm 1.47-1.69 (m, 2 H), 1.97-2.32 (m, 4 H), 3.27-4.42 (m, 3 H), 4.57-5.24 (m, 3 H), 7.10-9.13 (m, 8 H) | 433([M + H]+) |
| 153 | 9 | 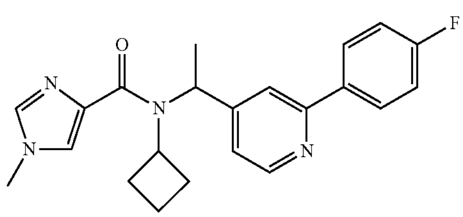 [SMILES: CC(c1ccnc(-c2ccc(F)cc2)c1)N(C(=O)c1cn(C)cn1)C1CCC1] | | 1H NMR (600 MHz, CHLOROFORM-d) d ppm 1.47-1.65 (m, 5 H), 1.70-1.86 (m, 4 H), 3.39-6.78 (m, 2 H), 3.72 (s, 3 H), 7.09-7.16 (m, 2 H), 7.22-7.25 (m, 1 H), 7.35 (s, 1 H), 7.52 (br. s., 1 H), 7.68 (s, 1 H), 7.92-7.97 (m, 2 H), 8.56-8.63 (m, 1 H) | 379([M + H]+) |
| 154 | 5 | 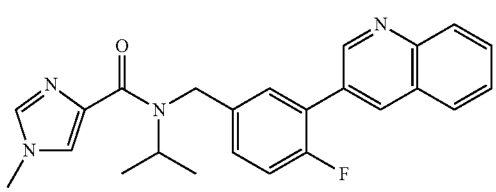 [SMILES: CC(C)N(Cc1ccc(F)c(-c2cnc3ccccc3c2)c1)C(=O)c1cn(C)cn1] | 2HCl | 1H NMR (600 MHz, DMSO-d6) d ppm 1.03-1.34 (m, 6 H), 3.53-5.12 (m, 6 H), 7.31-7.50 (m, 2 H), 7.60-8.22 (m, 6 H), 8.58-9.22 (m, 3 H) | 403([M + H]+) |

TABLE 1-15

| Compound | Example | Structure | Salt | NMR | (ESI pos.) m/z (ESI neg.) m/z |
|---|---|---|---|---|---|
| 155 | 8 | 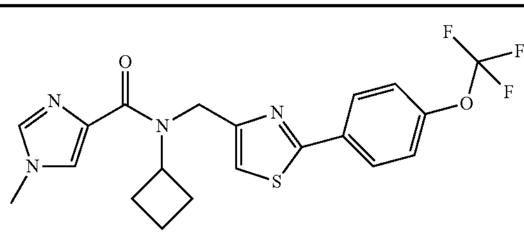 | | 1H NMR (600 MHz, CHLOROFORM-d) d ppm 1.43-1.78 (m, 2 H), 1.99-2.42 (m, 4 H), 3.70 (br. s., 3 H), 4.67-5.90 (m, 3 H), 6.88-7.63 (m, 5 H), 7.96 (d, J = 8.7 Hz, 2 H) | 437([M + H]+) |

TABLE 1-15-continued
| Compound | Example | Structure | Salt | NMR | (ESI pos.) m/z (ESI neg.) m/z |
|---|---|---|---|---|---|
| 156 | 2 | 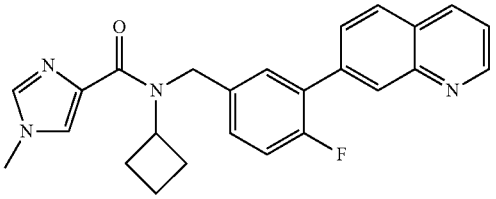 [SMILES: Cn1cnc(C(=O)N(Cc2ccc(F)c(-c3ccc4cccnc4c3)c2)C2CCC2)c1] | | 1H NMR (600 MHz, CHLOROFORM-d) d ppm 1.53-1.72 (m, 2 H), 2.11-2.26 (m, 4 H), 3.70 (s, 3 H), 4.49-5.85 (m, 3 H), 7.09-7.89 (m, 8 H), 8.16-8.26 (m, 2 H), 8.94 (dd, J = 4.1, 1.8 Hz, 1 H) | 415([M + H]+) |
| 157 | 2 | 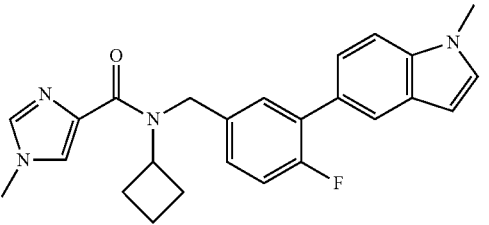 [SMILES: Cn1cnc(C(=O)N(Cc2ccc(F)c(-c3ccc4c(ccn4C)c3)c2)C2CCC2)c1] | | 1H NMR (600 MHz, CHLOROFORM-d) d ppm 1.48-1.71 (m, 2 H), 2.10-2.24 (m, 4 H), 3.68 (s, 3 H), 3.82 (s, 3 H), 4.43-5.82 (m, 3 H), 6.47-6.57 (m, 1 H), 7.00-7.81 (m, 9 H) | 417([M + H]+) |
| 158 | 5 | 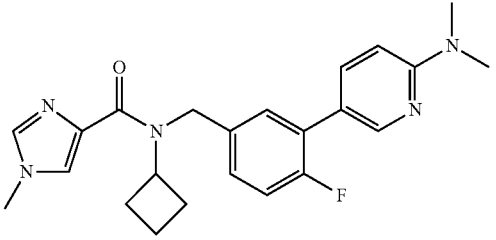 | | 1H NMR (600 MHz, CHLOROFORM-d) d ppm 1.53-1.71 (m, 2 H), 2.09-2.22 (m, 4 H), 3.13 (s, 6 H), 3.69 (s, 3 H), 4.44-5.89 (m, 3 H), 6.56 (d, J = 9.2 Hz, 1 H), 6.99-7.67 (m, 6 H), 8.32 (br. s, 1 H) | 408([M + H]+) |
| 159 | 5 | 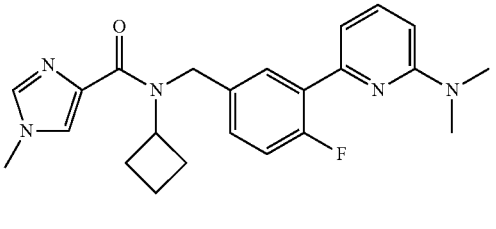 | | | 408([M + H]+) |
| 160 | 14 | 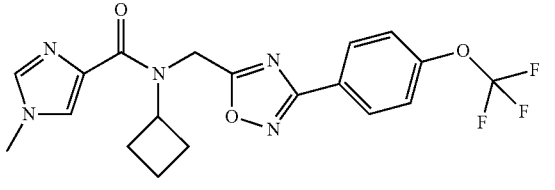 [SMILES: Cn1cnc(C(=O)N(Cc2nc(-c3ccc(OC(F)(F)F)cc3)no2)C2CCC2)c1] | | 1H NMR (600 MHz, CHLOROFORM-d) d ppm 1.61-1.81 (m, 2 H), 1.97-2.40 (m, 4 H), 3.62-3.78 (m, 4 H), 4.68-5.98 (m, 2 H), 7.22-8.18 (m, 6 H) | 422([M + H]+) |
| 161 | 15 | 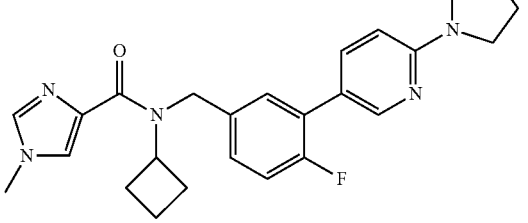 | 2HCl | 1H NMR (600 MHz, DMSO-d6) d ppm 1.49-1.64 (m, 2 H), 2.00-2.26 (m, 8 H), 3.14-3.94 (m, 7 H), 4.61-5.37 (m, 3 H), 6.99-8.92 (m, 8 H) | 434([M + H]+) |

TABLE 1-15-continued

| Compound | Example | Structure | Salt | NMR | (ESI pos.) m/z (ESI neg.) m/z |
|---|---|---|---|---|---|
| 162 | 3 | 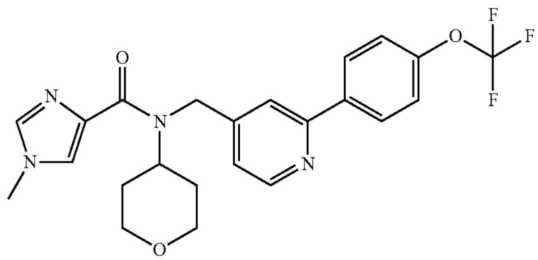 [SMILES: Cn1cnc(C(=O)N(Cc2ccnc(-c3ccc(OC(F)(F)F)cc3)c2)C2CCOCC2)c1] | 2HCl | 1H NMR (600 MHz, DMSO-d6) d ppm 1.41-1.90 (m, 4 H), 3.21-5.29 (m, 10 H), 7.30-9.04 (m, 9 H) | 461([M + H]+) |
| 163 | 3 | 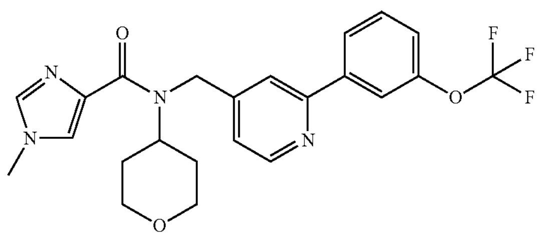 [SMILES: Cn1cnc(C(=O)N(Cc2ccnc(-c3cccc(OC(F)(F)F)c3)c2)C2CCOCC2)c1] | 2HCl | 1H NMR (600 MHz, DMSO-d6) d ppm 1.47-1.87 (m, 4 H), 3.15-5.28 (m, 10 H), 7.24-9.03 (m, 9 H) | 461([M + H]+) |
| 164 | 3 | 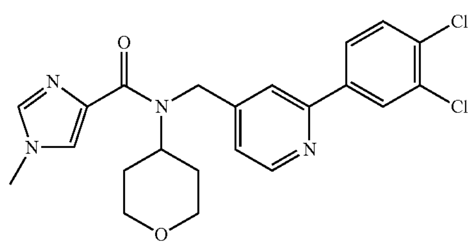 [SMILES: Cn1cnc(C(=O)N(Cc2ccnc(-c3ccc(Cl)c(Cl)c3)c2)C2CCOCC2)c1] | 2HCl | 1H NMR (600 MHz, DMSO-d6) d ppm 1.46-1.89 (m, 4 H), 3.29-5.20 (m, 10 H), 7.26-7.41 (m, 1 H), 7.65-9.04 (m, 7 H) | 445([M + H]+) 447([M + 3]+) |
| 165 | 8 | 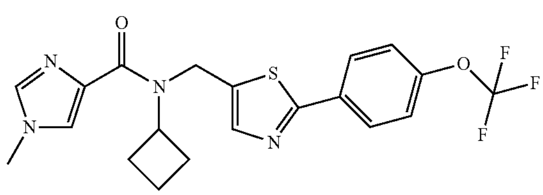 [SMILES: Cn1cnc(C(=O)N(Cc2cnc(-c3ccc(OC(F)(F)F)cc3)s2)C2CCC2)c1] | | | 437([M + H]+) |

TABLE 1-16

| Compound | Example | Structure | Salt | NMR | (ESI pos.) m/z (ESI neg.) m/z |
|---|---|---|---|---|---|
| 166 | 5 | 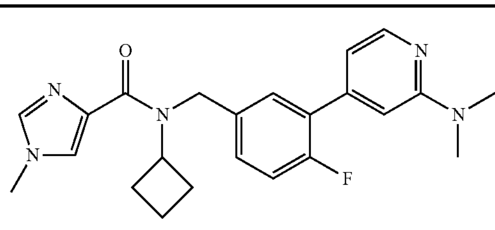 | 2HCl | 1H NMR (600 MHz, DMSO-d6) d ppm 1.48-1.64 (m, 2 H), 1.99-2.25 (m, 4 H), 3.24 (s, 6 H), 3.29-3.86 (m, 3 H), 4.48-5.44 (m, 3 H), 6.88-8.69 (m, 8 H) | 408([M + H]+) |

TABLE 1-16-continued

| Compound | Example | Structure | Salt | NMR | (ESI pos.) m/z (ESI neg.) m/z |
|---|---|---|---|---|---|
| 167 | 5 | 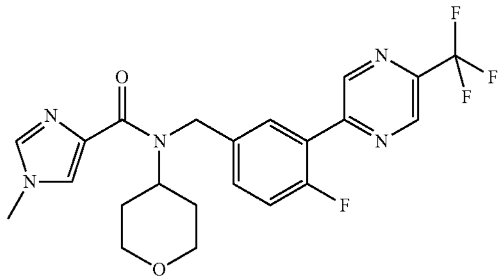 [SMILES: Cn1cnc(C(=O)N(Cc2ccc(F)c(-c3cnc(C(F)(F)F)cn3)c2)C2CCOCC2)c1] | | 1H NMR (600 MHz, CHLOROFORM-d) d ppm 1.30-1.95 (m, 4 H), 3.36-3.52 (m, 2 H), 3.72 (br. s., 3 H), 3.96 (m, J = 8.7 Hz, 2 H), 4.60-5.77 (m, 3 H), 7.10-7.67 (m, 4 H), 7.99 (s, 1 H), 8.84-9.24 (m, 2 H) | 464([M + H]+) |
| 168 | 5 | 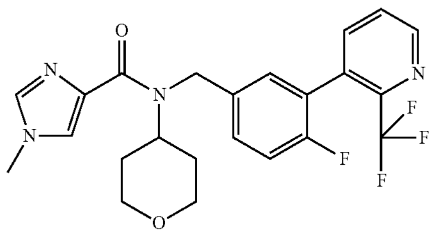 [SMILES: Cn1cnc(C(=O)N(Cc2ccc(F)c(-c3cccnc3C(F)(F)F)c2)C2CCOCC2)c1] | | | 463([M + H]+) |
| 169 | 5 | 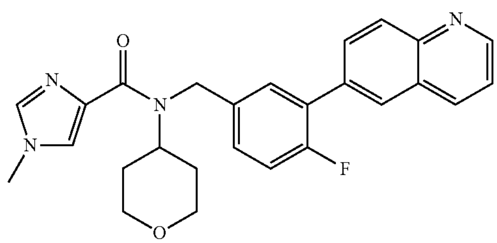 [SMILES: Cn1cnc(C(=O)N(Cc2ccc(F)c(-c3ccc4ncccc4c3)c2)C2CCOCC2)c1] | | 1H NMR (600 MHz, CHLOROFORM-d) d ppm 1.19-1.95 (m, 4 H), 3.34-3.53 (m, 2 H), 3.64 (br. s., 3 H), 3.88-4.07 (m, 2 H), 4.61-5.77 (m, 3 H), 6.99-7.67 (m, 6 H), 7.81-8.06 (m, 2 H), 8.09-8.26 (m, 2 H), 8.93 (dd, J = 4.1, 1.4 Hz, 1 H) | 445([M + H]+) |
| 170 | 5 | 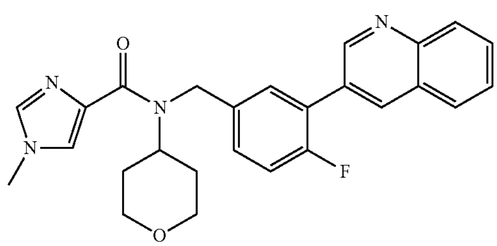 [SMILES: Cn1cnc(C(=O)N(Cc2ccc(F)c(-c3cnc4ccccc4c3)c2)C2CCOCC2)c1] | | 1H NMR (600 MHz, CHLOROFORM-d) d ppm 1.46-1.96 (m, 4 H), 3.46 (t, J = 11.5 Hz, 2 H), 3.71 (br. s., 3 H), 3.90-4.06 (m, 2 H), 4.59-5.77 (m, 3 H), 7.09-7.65 (m, 6 H), 7.68-7.92 (m, 2 H), 8.13 (d, J = 8.3 Hz, 1 H), 8.21-8.38 (m, 1 H), 9.05 (br. s., 1 H) | 445([M + H]+) |
| 171 | 6 | 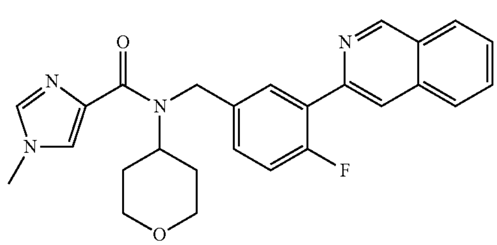 [SMILES: Cn1cnc(C(=O)N(Cc2ccc(F)c(-c3cc4ccccc4cn3)c2)C2CCOCC2)c1] | 2HCl | | 445([M + H]+) |
| 172 | 6 | 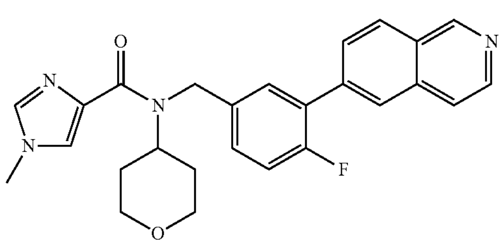 [SMILES: Cn1cnc(C(=O)N(Cc2ccc(F)c(-c3ccc4cnccc4c3)c2)C2CCOCC2)c1] | 2HCl | Determined as free form 1H NMR (600 MHz, CHLOROFORM-d) d ppm 1.43-1.96 (m, 4 H), 3.36-3.55 (m, 2 H), 3.63-3.80 (m, 3 H), 3.87-4.07 (m, 2 H), 4.60-5.72 (m, 3 H), 7.03-9.34 (m, 11 H) | 445([M + H]+) |

TABLE 1-16-continued

| Compound | Example | Structure | Salt | NMR | (ESI pos.) m/z (ESI neg.) m/z |
|---|---|---|---|---|---|
| 173 | 9 | 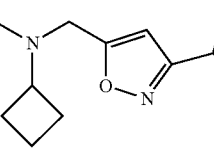 | | | 437([M + H]+) |
| 174 | 3 | 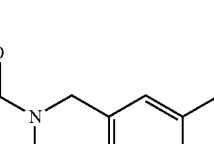 | | 1H NMR (600 MHz, CHLOROFORM-d) d ppm 1.48-1.90 (m, 4 H), 3.42-3.51 (m, 2 H), 3.64-3.79 (m, 3 H), 3.89-4.05 (m, 2 H), 4.65-5.74 (m, 3 H), 7.11-8.00 (m, 7 H), 8.53-8.60 (m, 1 H) | 479([M + H]+) |
| 175 | 3 | 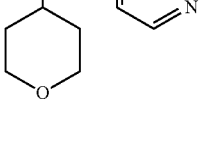 | 2HCl | 1H NMR (600 MHz, DMSO-d6) d ppm 1.48-1.84 (m, 4 H), 3.24-5.26 (m, 10 H), 7.25-8.92 (m, 8 H) | 479([M + H]+) |
| 176 | 3 | 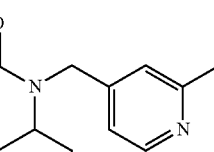 | 2HCl | 1H NMR (600 MHz, DMSO-d6) d ppm 1.52-1.67 (m, 2 H), 2.02-2.27 (m, 4 H), 3.29-5.23 (m, 6 H), 7.15-8.22 (m, 6 H), 8.51-9.20 (m, 2 H) | 383([M + H]+) |

TABLE 1-17

| Compound | Example | Structure | Salt | NMR | (ESI pos.) m/z (ESI neg.) m/z |
|---|---|---|---|---|---|
| 177 | 3 | 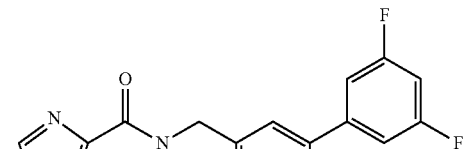 | | 1H NMR (600 MHz, CHLOROFORM-d) d ppm 1.58-1.71 (m, 2 H), 1.96-2.29 (m, 4 H), 3.71 (br. s., 3 H), 4.67-5.99 (m, 3 H), 6.83 (tt, J = 8.7, 2.3 Hz, 1 H). 7.09-7.64 (m, 6 H), 8.58 (d, J = 5.0 Hz, 1 H) | 383([M + H]+) |
| 178 | 3 | 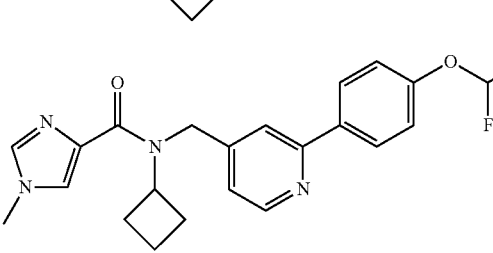 | 2HCl | 1H NMR (600 MHz, DMSO-d6) d ppm 1.52-1.68 (m, 2 H), 2.05-2.27 (m, 4 H), 3.24-5.39 (m, 6 H), 7.18-7.54 (m, 5 H), 7.80-8.25 (m, 3 H), 8.57-9.11 (m, 2 H) | 413([M + H]+) |

TABLE 1-17-continued
| Compound | Example | Structure | Salt | NMR | (ESI pos.) m/z (ESI neg.) m/z |
|---|---|---|---|---|---|
| 179 | 3 | 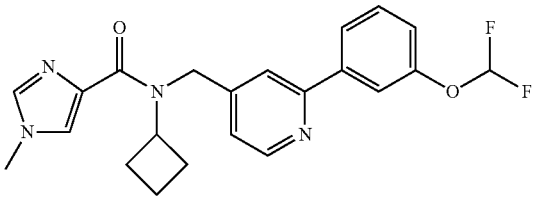 [SMILES: Cn1cnc(C(=O)N(Cc2ccnc(-c3cccc(OC(F)F)c3)c2)C2CCC2)c1] | 2HCl | 1H NMR (600 MHz, DMSO-d6) d ppm 1.50-1.67 (m, 2 H), 1.99-2.26 (m, 4 H), 3.08-5.32 (m, 6 H), 7.14-8.27 (m, 8 H), 8.54-9.11 (m, 2 H) | 413([M + H]+) |
| 180 | 2 | 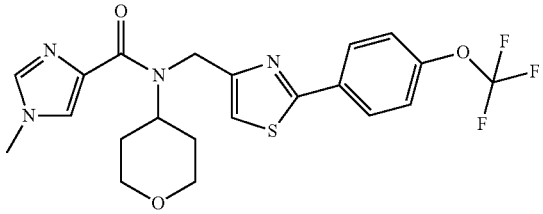 [SMILES: Cn1cnc(C(=O)N(Cc2csc(-c3ccc(OC(F)(F)F)cc3)n2)C2CCOCC2)c1] | 1HCl | 1H NMR (600 MHz, DMSO-d6) d ppm 1.41-2.00 (m, 4 H), 3.26-5.06 (m, 7 H), 5.54-6.91 (m, 3 H), 7.18-8.26 (m, 6 H), 9.06 (br. s., 1 H) | 467([M + H]+) |
| 181 | 2 | 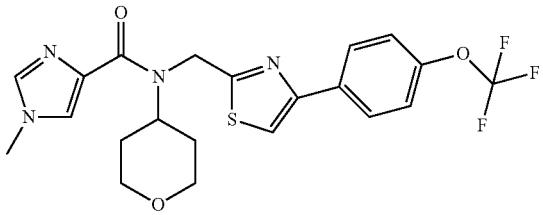 [SMILES: Cn1cnc(C(=O)N(Cc2nc(-c3ccc(OC(F)(F)F)cc3)cs2)C2CCOCC2)c1] | | 1H NMR (600 MHz, CHLOROFORM-d) d ppm 1.45-2.15 (m, 4 H), 3.47 (t, J = 11.2 Hz, 2 H), 3.75 (br. s., 3 H), 3.94-4.05 (m, 2 H), 4.63-5.91 (m, 3 H), 7.16-7.99 (m, 7 H) | 467([M + H]+) |
| 182 | 5 | 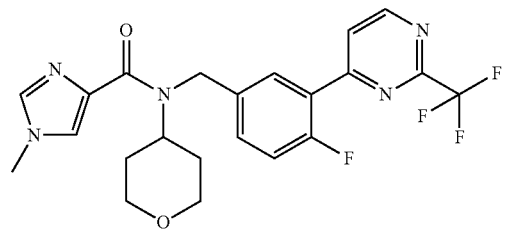 [SMILES: Cn1cnc(C(=O)N(Cc2ccc(F)c(-c3ccnc(C(F)(F)F)n3)c2)C2CCOCC2)c1] | | 1H NMR (600 MHz, CHLOROFORM-d) d ppm 1.58 (s, 4 H), 3.36-3.56 (m, 2 H), 3.72 (br. s., 3 H), 3.96 (m, J = 10.1 Hz, 2 H), 4.51-5.78 (m, 3 H), 7.03-7.68 (m, 4 H), 8.01 (d, J = 5.5 Hz, 1 H), 8.18 (br. s., 1 H), 8.91 (d, J = 5.5 Hz, 1 H) | 464([M + H]+) |
| 183 | 5 | 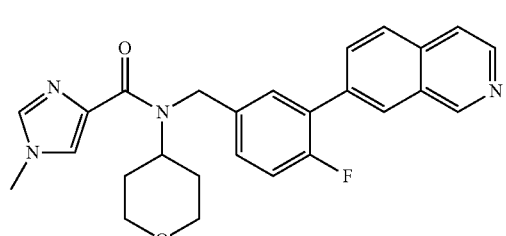 | 2HCl | 1H NMR (600 MHz, DMSO-d6) d ppm 1.34-2.40 (m, 4 H), 3.06-4.17 (m, 7 H), 4.31-5.34 (m, 3 H), 7.25-8.82 (m, 10 H), 9.88 (s, 1 H) | 445([M + H]+) |
| 184 | 9 | 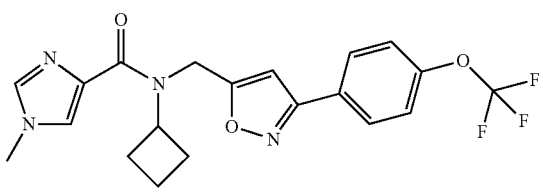 [SMILES: Cn1cnc(C(=O)N(Cc2cc(-c3ccc(OC(F)(F)F)cc3)no2)C2CCC2)c1] | | | 421([M + H]+) |

TABLE 1-17-continued
| Compound | Example | Structure | Salt | NMR | (ESI pos.) m/z (ESI neg.) m/z |
|---|---|---|---|---|---|
| 185 | 5 | 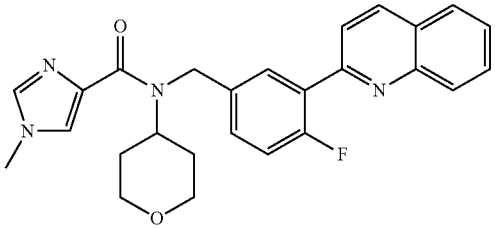 [SMILES: Cn1cnc(C(=O)N(Cc2ccc(F)c(-c3ccc4ccccc4n3)c2)C2CCOCC2)c1] | | | 445([M + H]+) |
| 186 | 2 | 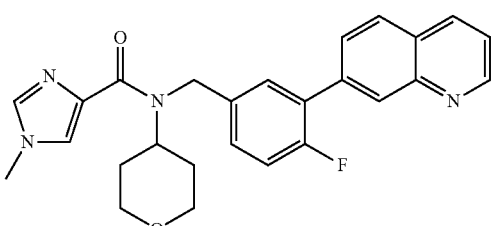 | | 1H NMR (600 MHz, CHLOROFORM-d) d ppm 1.49-1.96 (m, 4 H), 3.46 (t, J = 11.0 Hz, 2 H), 3.71 (s, 3 H), 3.97 (t, J = 8.7 Hz, 2 H), 4.59-5.82 (m, 3 H), 6.89-7.94 (m, 8 H), 8.10-8.29 (m, 2 H), 8.94 (dd, J = 4.4, 1.6 Hz, 1 H) | 445([M + H]+) |
| 187 | 3 | 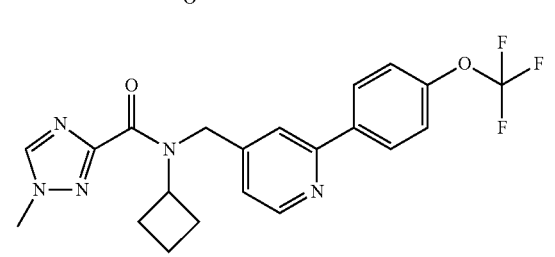 | 1HCl | 1H NMR (600 MHz, DMSO-d6) d ppm 1.37-1.65 (m, 2 H), 1.93-2.19 (m, 4 H), 3.71-5.03 (m, 6 H), 7.26-7.61 (m, 3 H), 7.83-8.72 (m, 5 H) | 432([M + H]+) |
TABLE 1-18
| Compound | Example | Structure | Salt | NMR | (ESI pos.) m/z (ESI neg.) m/z |
|---|---|---|---|---|---|
| 188 | 3 | 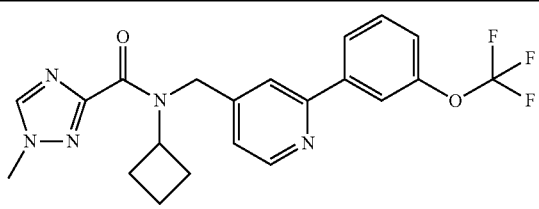 | 1HCl | 1H NMR (600 MHz, DMSO-d6) d ppm 1.37-1.65 (m, 2 H), 1.90-2.17 (m, 4 H), 3.77-5.03 (m, 6 H), 7.26-8.74 (m, 8 H) | 432([M + H]+) |
| 189 | 3 | 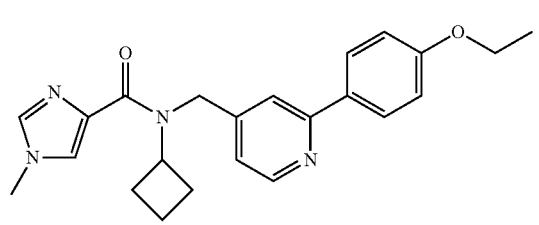 [SMILES: CCOc1ccc(-c2cc(CN(C(=O)c3cn(C)cn3)C3CCC3)ccn2)cc1] | 2HCl | 1H NMR (600 MHz, DMSO-d6) d ppm 1.37 (t, J = 6.9 Hz, 3 H), 1.52-1.66 (m, 2 H), 2.01-2.28 (m, 4 H), 3.21-5.46 (m, 6 H), 4.14 (q, J = 7.2 Hz, 2 H), 7.07-7.19 (m, 2 H), 7.35-8.23 (m, 5 H), 8.59-9.05 (m, 2 H) | 391([M + H]+) |
| 190 | 6 | 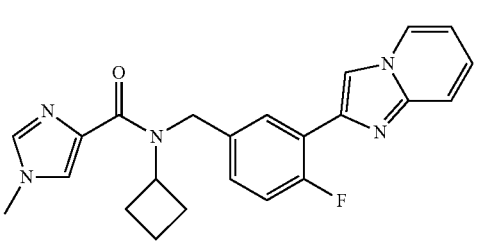 [SMILES: Cn1cnc(C(=O)N(Cc2ccc(F)c(-c3cn4ccccc4n3)c2)C2CCC2)c1] | | | 404([M + H]+) |

TABLE 1-18-continued

| Compound | Example | Structure | Salt | NMR | (ESI pos.) m/z (ESI neg.) m/z |
|---|---|---|---|---|---|
| 191 | 3 | 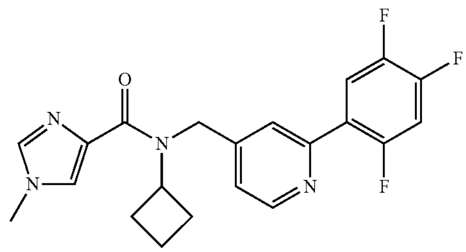 [SMILES: Cn1cnc(C(=O)N(Cc2ccnc(-c3cc(F)c(F)cc3F)c2)C2CCC2)c1] | 2HCl | 1H NMR (600 MHz, DMSO-d6) d ppm 1.50-1.67 (m, 2 H), 2.00-2.28 (m, 4 H), 3.38-4.36 (m, 3 H), 4.78-5.34 (m, 3 H), 7.24-8.22 (m, 5 H), 8.58-9.08 (m, 2 H) | 401([M + H]+) |
| 192 | 3 | 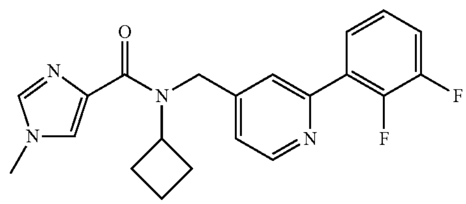 [SMILES: Cn1cnc(C(=O)N(Cc2ccnc(-c3cccc(F)c3F)c2)C2CCC2)c1] | 2HCl | 1H NMR (600 MHz, DMSO-d6) d ppm 1.51-1.66 (m, 2 H), 2.04-2.27 (m, 4 H), 3.13-4.39 (m, 3 H), 4.59-5.44 (m, 3 H), 7.22-8.28 (m, 6 H), 8.56-9.15 (m, 2 H) | 383([M + H]+) |
| 193 | 3 | 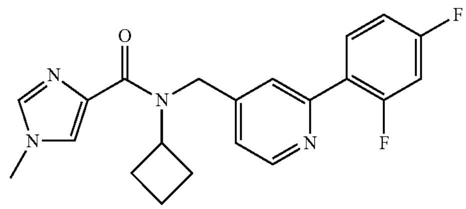 [SMILES: Cn1cnc(C(=O)N(Cc2ccnc(-c3ccc(F)cc3F)c2)C2CCC2)c1] | 2HCl | 1H NMR (600 MHz, DMSO-d6) d ppm 1.51-1.66 (m, 2 H), 2.00-2.30 (m, 4 H), 3.49-4.43 (m, 3 H), 4.71-5.26 (m, 3 H), 7.19-8.25 (m, 6 H), 8.59-9.12 (m, 2 H) | 383([M + H]+) |
| 194 | 3 | 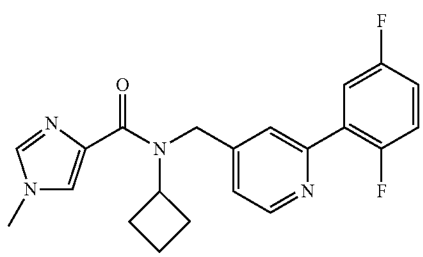 [SMILES: Cn1cnc(C(=O)N(Cc2ccnc(-c3cc(F)ccc3F)c2)C2CCC2)c1] | 2HCl | 1H NMR (600 MHz, DMSO-d6) d ppm 1.51-1.66 (m, 2 H), 2.03-2.24 (m, 4 H), 3.18-4.20 (m, 3 H), 4.66-5.35 (m, 3 H), 7.25-8.24 (m, 6 H), 8.59-9.07 (m, 2 H) | 383([M + H]+) |
| 195 | 3 | 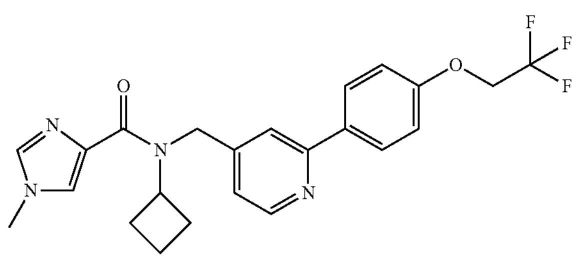 [SMILES: Cn1cnc(C(=O)N(Cc2ccnc(-c3ccc(OCC(F)(F)F)cc3)c2)C2CCC2)c1] | | 1H NMR (600 MHz, CHLOROFORM-d) d ppm 1.49-1.71 (m, 2 H) 2.01-2.24 (m, 4 H) 3.70 (br. s., 3 H) 4.32-4.46 (m, 2 H) 4.67-6.00 (m, 3 H) 6.97-7.97 (m, 8 H) 8.55 (d, J = 5.04 Hz, 1 H) | 445([M + H]+) |
| 196 | 3 | 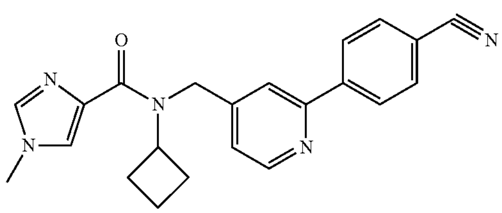 [SMILES: Cn1cnc(C(=O)N(Cc2ccnc(-c3ccc(C#N)cc3)c2)C2CCC2)c1] | 2HCl | 1H NMR (600 MHz, DMSO-d6) d ppm 1.48-1.67 (m, 2 H), 2.02-2.24 (m, 4 H), 3.35-5.31 (m, 6 H), 7.19-9.13 (m, 9 H) | 372([M + H]+) |

TABLE 1-18-continued

| Compound | Example | Structure | Salt | NMR | (ESI pos.) m/z (ESI neg.) m/z |
|---|---|---|---|---|---|
| 197 | 3 | 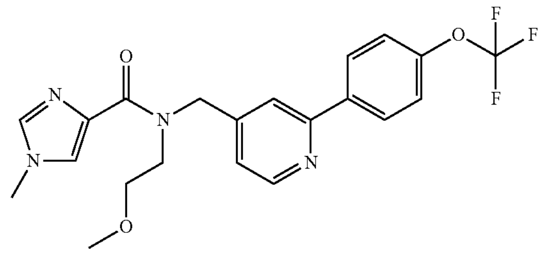 [SMILES: COCCN(Cc1ccnc(-c2ccc(OC(F)(F)F)cc2)c1)C(=O)c1cn(C)cn1] | 2HCl | 1H NMR (600 MHz, DMSO-d6) d ppm 3.22 (s, 3 H) 3.41-5.31 (m, 9 H) 7.26-9.05 (m, 9 H) | 435([M + H]+) |
| 198 | 3 | 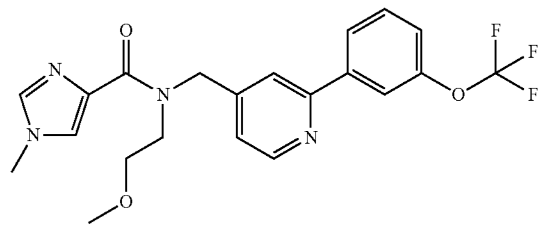 [SMILES: COCCN(Cc1ccnc(-c2cccc(OC(F)(F)F)c2)c1)C(=O)c1cn(C)cn1] | 2HCl | 1H NMR (600 MHz, DMSO-d6) d ppm 3.22 (s, 3 H) 3.50-5.29 (m, 9 H) 7.25-9.01 (m, 9 H) | 435([M + H]+) |

TABLE 1-19

| Compound | Example | Structure | Salt | NMR | (ESI pos.) m/z (ESI neg.) m/z |
|---|---|---|---|---|---|
| 199 | 9 | 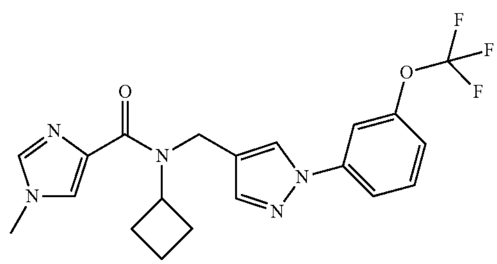 [SMILES: Cn1cnc(C(=O)N(Cc2cnn(-c3cccc(OC(F)(F)F)c3)c2)C2CCC2)c1] | | | 420([M + H]+) |
| 200 | 6 | 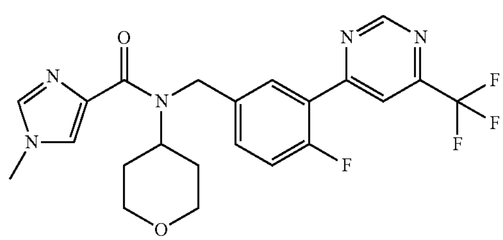 [SMILES: Cn1cnc(C(=O)N(Cc2ccc(F)c(-c3cc(C(F)(F)F)ncn3)c2)C2CCOCC2)c1] | 1HCl | Determined as free form 1H NMR (600 MHz, CHLOROFORM-d) d ppm 1.56-1.94 (m, 4 H), 3.35-3.53 (m, 2 H), 3.61-3.82 (m, 3 H), 3.87-4.06 (m, 2 H), 4.56-5.70 (m, 3 H), 7.02-7.64 (m, 5 H), 8.15 (s, 1 H), 9.41 (s, 1 H) | 464([M + H]+) |
| 201 | 6 | 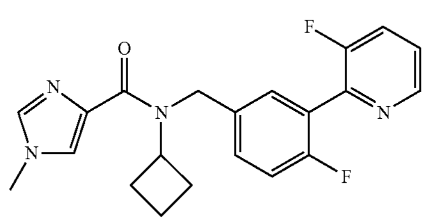 [SMILES: Cn1cnc(C(=O)N(Cc2ccc(F)c(-c3ncccc3F)c2)C2CCC2)c1] | 1HCl | Determined as free form 1H NMR (600 MHz, CHLOROFORM-d) d ppm 1.55-1.71 (m, 2 H), 2.04-2.24 (m, 4 H), 3.56-3.81 (m, 4 H), 4.38-5.68 (m, 2 H), 7.00-7.54 (m, 7 H), 8.46-8.58 (m, 1 H) | 383([M + H]+) |

TABLE 1-19-continued

| Compound | Example | Structure | Salt | NMR | (ESI pos.) m/z (ESI neg.) m/z |
|---|---|---|---|---|---|
| 202 | 6 | 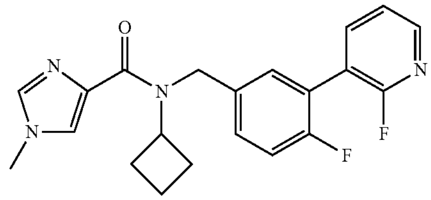 [SMILES: Cn1cnc(C(=O)N(Cc2ccc(F)c(-c3cccnc3F)c2)C2CCC2)c1] | 1HCl | Determined as free form 1H NMR (600 MHz, CHLOROFORM-d) d ppm 1.55-1.74 (m, 2 H), 2.00-2.25 (m, 4 H), 3.56-3.83 (m, 4 H), 4.25-5.91 (m, 2 H), 6.85-8.28 (m, 8 H) | 383([M + H]+) |
| 203 | 6 | 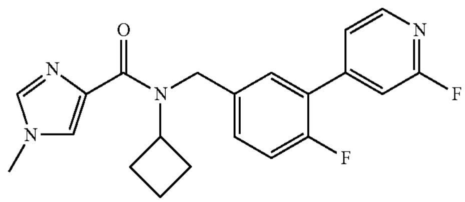 [SMILES: Cn1cnc(C(=O)N(Cc2ccc(F)c(-c3ccnc(F)c3)c2)C2CCC2)c1] | 1HCl | Determined as free form 1H NMR (600 MHz, CHLOROFORM-d) d ppm 1.55-1.74 (m, 2 H), 1.99-2.27 (m, 4 H), 3.54-3.87 (m, 4 H), 4.43-6.00 (m, 2 H), 6.86-7.60 (m, 7 H), 8.19-8.34 (m, 1 H) | 383([M + H]+) |
| 204 | 5 | 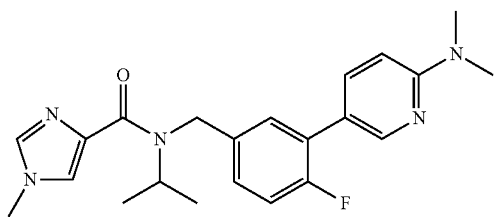 | 2HCl | 1H NMR (600 MHz, DMSO-d6) d ppm 1.01-1.31 (m, 6 H) 3.22 (s, 6 H) 3.57-5.17 (m, 6 H) 7.07-8.76 (m, 8 H) | 396([M + H]+) |
| 205 | 5 | 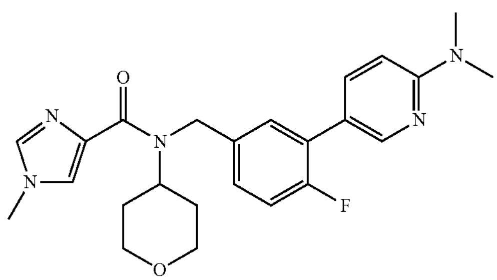 | 2HCl | 1H NMR (600 MHz, DMSO-d6) d ppm 1.43-1.87 (m, 4 H) 3.06-5.19 (m, 10 H) 3.22 (s, 6 H) 7.04-8.73 (m, 8 H) | 438([M + H]+) |
| 206 | 15 | 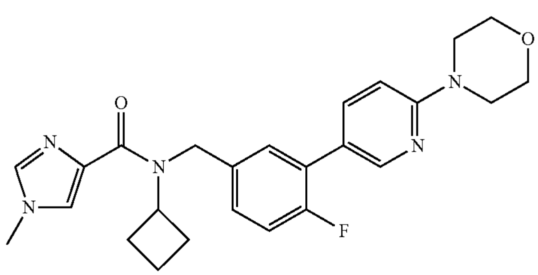 [SMILES: Cn1cnc(C(=O)N(Cc2ccc(F)c(-c3ccc(N4CCOCC4)nc3)c2)C2CCC2)c1] | | 1H NMR (600 MHz, CHLOROFORM-d) d ppm 1.35-1.74 (m, 2 H), 1.97-2.30 (m, 4 H), 3.53-3.58 (m, 4 H), 3.70 (s, 3 H), 3.81-3.87 (m, 4 H), 4.33-5.79 (m, 3 H), 6.69 (s, 1 H), 6.95-7.81 (m, 6 H), 8.35 (s, 1 H) | 450([M + H]+) |
| 207 | 8 | 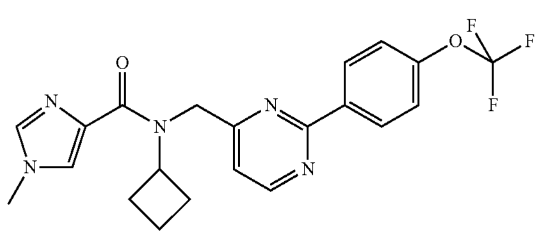 [SMILES: Cn1cnc(C(=O)N(Cc2ccnc(-c3ccc(OC(F)(F)F)cc3)n2)C2CCC2)c1] | | 1H NMR (600 MHz, CHLOROFORM-d) d ppm 1.39-2.33 (m, 6 H), 3.27-3.91 (m, 3 H), 4.81-5.98 (m, 3 H), 7.04-7.66 (m, 5 H), 8.50 (d, J = 9.2 Hz, 2 H), 8.67 (d, J = 5.0 Hz, 1 H) | 432([M + H]+) |

TABLE 1-19-continued

| Compound | Example | Structure | Salt | NMR | (ESI pos.) m/z (ESI neg.) m/z |
|---|---|---|---|---|---|
| 208 | 6 | 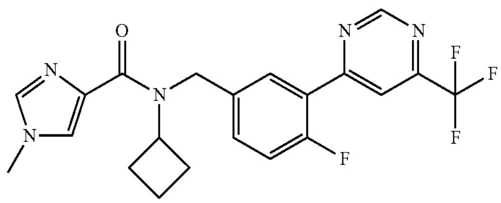 [SMILES: Cn1cnc(C(=O)N(Cc2ccc(F)c(-c3cc(C(F)(F)F)ncn3)c2)C2CCC2)c1] | | 1H NMR (600 MHz, CHLOROFORM-d) d ppm 1.52-1.70 (m, 2 H) 2.06-2.22 (m, 4 H) 3.70 (br. s., 3 H) 4.50-5.96 (m, 3 H) 7.10-8.19 (m, 6 H) 9.42 (s, 1 H) | 434([M + H]+) |
| 209 | 6 | 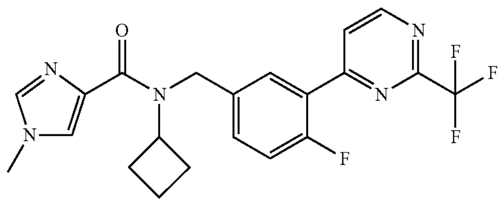 [SMILES: Cn1cnc(C(=O)N(Cc2ccc(F)c(-c3ccnc(C(F)(F)F)n3)c2)C2CCC2)c1] | | 1H NMR (600 MHz, CHLOROFORM-d) d ppm 1.50-1.71 (m, 2 H) 2.04-2.23 (m, 4 H) 3.71 (s, 3 H) 4.47-5.92 (m, 3 H) 7.04-8.26 (m, 6 H) 8.91 (d, J = 5.50 Hz, 1 H) | 434([M + H]+) |

TABLE 1-20

| Compound | Example | Structure | Salt | NMR | (ESI pos.) m/z (ESI neg.) m/z |
|---|---|---|---|---|---|
| 210 | 6 | 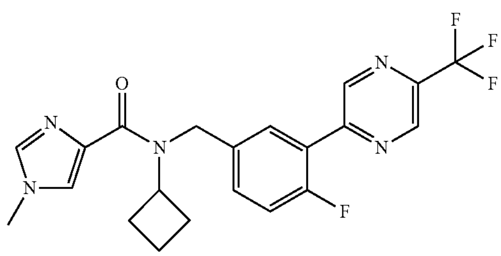 [SMILES: Cn1cnc(C(=O)N(Cc2ccc(F)c(-c3cnc(C(F)(F)F)cn3)c2)C2CCC2)c1] | | | 434([M + H]+) |
| 211 | 6 | 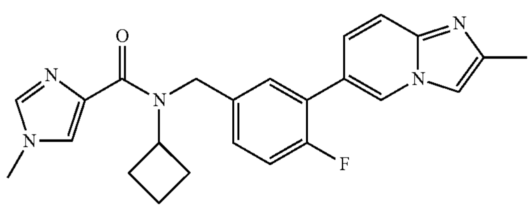 | | 1H NMR (200 MHz, CHLOROFORM-d) d ppm 1.44-1.85 (m, 2 H), 2.00-2.28 (m, 4 H), 2.47 (s, 3 H), 3.38-5.84 (m, 6 H), 6.99-7.64 (m, 8 H), 8.23 (s, 1 H) | 418([M + H]+) |
| 212 | 9 | 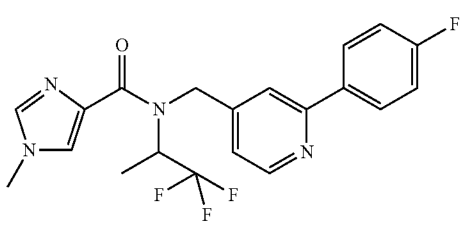 [SMILES: CC(N(Cc1ccnc(-c2ccc(F)cc2)c1)C(=O)c1cn(C)cn1)C(F)(F)F] | 2HCl | | 407([M + H]+) |
| 213 | 16 | 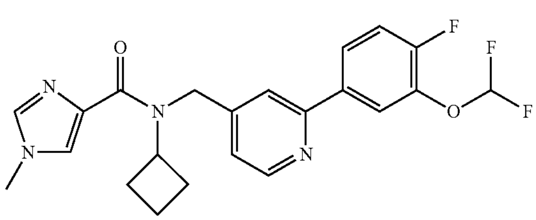 [SMILES: Cn1cnc(C(=O)N(Cc2ccnc(-c3ccc(F)c(OC(F)F)c3)c2)C2CCC2)c1] | 2HCl | 1H NMR (600 MHz, DMSO-d6) d ppm 1.78-2.58 (m, 6 H), 3.71-5.42 (m, 6 H), 7.09-9.10 (m, 9 H) | 431([M + H]+) |

TABLE 1-20-continued

| Compound | Example | Structure | Salt | NMR | (ESI pos.) m/z (ESI neg.) m/z |
|---|---|---|---|---|---|
| 214 | 3 | 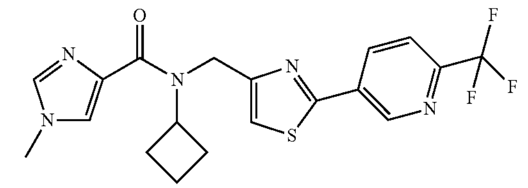 [SMILES: Cn1cnc(C(=O)N(Cc2csc(-c3ccc(C(F)(F)F)nc3)n2)C2CCC2)c1] | | 1H NMR (600 MHz, CHLOROFORM-d) d ppm 1.14-2.47 (m, 6 H), 3.71 (br. s., 3 H), 4.64-5.91 (m, 3 H), 7.02-7.83 (m, 4 H), 8.39 (d, J = 8.3 Hz, 1 H), 9.24 (s, 1 H) | 422([M + H]+) |
| 215 | 3 | 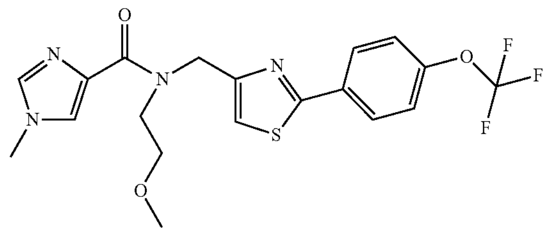 [SMILES: COCCN(Cc1csc(-c2ccc(OC(F)(F)F)cc2)n1)C(=O)c1cn(C)cn1] | | | 441([M + H]+) |
| 216 | 5 | 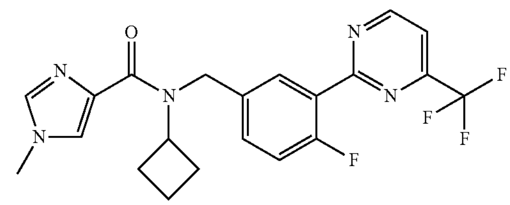 [SMILES: Cn1cnc(C(=O)N(Cc2ccc(F)c(-c3nccc(C(F)(F)F)n3)c2)C2CCC2)c1] | | 1H NMR (600 MHz, CHLOROFORM-d) d ppm 0.94-2.29 (m, 6 H), 3.51-3.83 (m, 3 H), 4.39-5.59 (m, 3 H), 7.02-7.63 (m, 5 H), 7.99 (br. s., 1 H), 9.10 (d, J = 5.0 Hz, 1 H) | 434([M + H]+) |
| 217 | 2 | 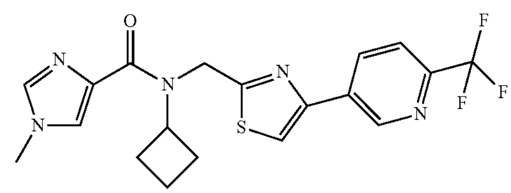 [SMILES: Cn1cnc(C(=O)N(Cc2nc(-c3ccc(C(F)(F)F)nc3)cs2)C2CCC2)c1] | | | 422([M + H]+) |
| 218 | 3 | 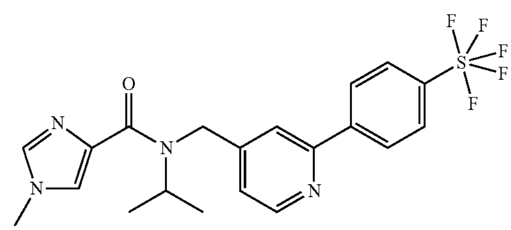 [SMILES: CC(C)N(Cc1ccnc(-c2ccc(S(F)(F)(F)(F)F)cc2)c1)C(=O)c1cn(C)cn1] | | | 461([M + H]+) |
| 219 | 16 | 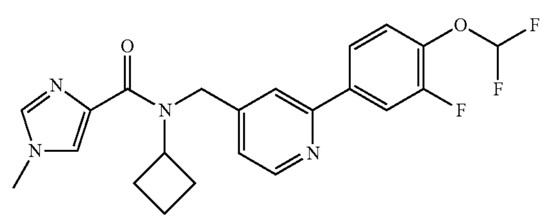 [SMILES: Cn1cnc(C(=O)N(Cc2ccnc(-c3ccc(OC(F)F)c(F)c3)c2)C2CCC2)c1] | | 1H NMR (600 MHz, CHLOROFORM-d) d ppm 1.59-1.74 (m, 2 H), 1.97-2.29 (m, 4 H), 3.43-3.90 (m, 3 H), 4.63-6.03 (m, 3 H), 6.39-6.78 (m, 1 H), 7.02-7.90 (m, 7 H), 8.57 (d, J = 5.0 Hz, 1 H) | 431([M + H]+) |
| 220 | 3 | 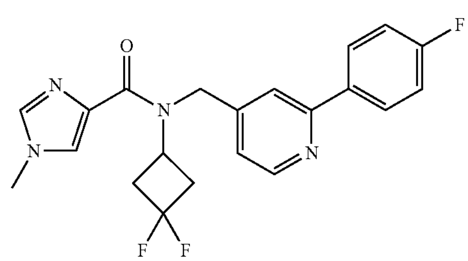 [SMILES: Cn1cnc(C(=O)N(Cc2ccnc(-c3ccc(F)cc3)c2)C2CC(F)(F)C2)c1] | | | 401([M + H]+) |

TABLE 1-21

| Compound | Example | Structure | Salt | NMR | (ESI pos.) m/z (ESI neg.) m/z |
|---|---|---|---|---|---|
| 221 | 2 | 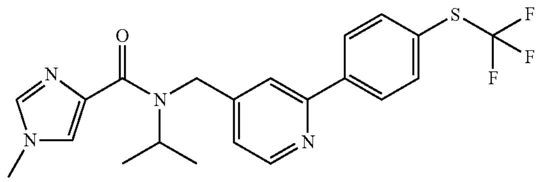 [SMILES: CC(C)N(Cc1ccnc(-c2ccc(SC(F)(F)F)cc2)c1)C(=O)c1cn(C)cn1] | 2HCl | 1H NMR (600 MHz, DMSO-d6) d ppm 1.23 (br. s., 6 H), 3.38-5.18 (m, 6 H), 7.19-8.94 (m, 9 H) | 435([M + H]+) |
| 222 | 8 | 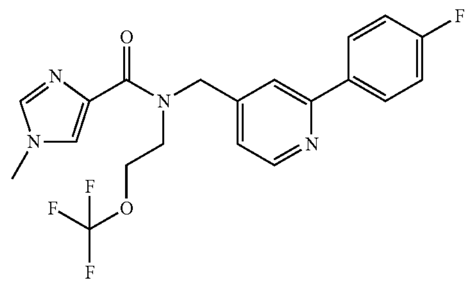 [SMILES: Cn1cnc(C(=O)N(CCOC(F)(F)F)Cc2ccnc(-c3ccc(F)cc3)c2)c1] | | | 423([M + H]+) |
| 223 | 5 | 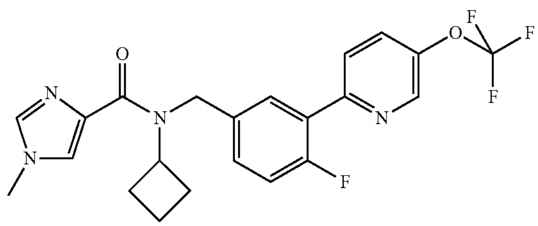 [SMILES: Cn1cnc(C(=O)N(Cc2ccc(F)c(-c3ccc(OC(F)(F)F)cn3)c2)C2CCC2)c1] | | 1H NMR (600 MHz, CHLOROFORM-d) d ppm 1.49-1.72 (m, 2 H), 1.99-2.24 (m, 4 H), 3.57-3.79 (m, 3 H), 4.32-5.92 (m, 3 H), 6.90-7.89 (m, 7 H), 8.63 (d, J = 2.8 Hz, 1 H) | 449([M + H]+) |
| 224 | 5 | 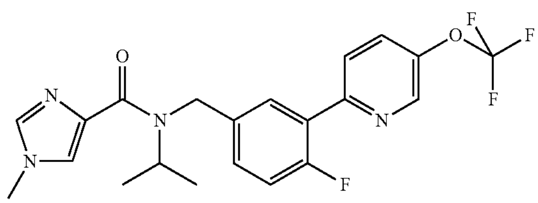 [SMILES: CC(C)N(Cc1ccc(F)c(-c2ccc(OC(F)(F)F)cn2)c1)C(=O)c1cn(C)cn1] | | | 437([M + H]+) |

Test Example 1

Glycine Uptake Inhibition Experiment

A glycine uptake inhibition experiment was conducted in accordance with the method described in Neuron, 8, 927-935, 1992. Used in the experiment were T98G cells (glioma cells) developing a human type 1 glycine transporter of (GlyT1). The T98G cells were seeded in a 96-well plate at a density of $2.0 \times 10^4$ cells per well and cultured overnight in a $CO_2$ incubator. The test substance was first dissolved in a 100% DMSO solution and then dissolved in a 10 mM HEPES buffer solution (pH 7.4) supplemented with 150 mM sodium chloride, 1 mM calcium chloride, 5 mM potassium chloride, 1 mM magnesium chloride, 10 mM glucose, and 0.2% bovine serum albumin. After removing the cell culture medium, the test substance was subjected to a 10-min pretreatment. Thereafter, the test substance and [$^3$H] glycine (final concentration: 250 nM) were added to the cells and reaction was performed at room temperature for 15 minutes. After the end of the reaction, the extracellular fluid was aspirated with a manifold to remove the excess marker glycine present outside of the cells; thereafter, the cells were lysed with an aqueous solution of 0.5 M sodium hydroxide. The glycine content in the cells was determined by measuring the radioactivity in the cell lysate with a liquid scintillation counter. With the amount of glycine uptake in the presence of 10 μM ALX5407 being referred to as the nonspecific uptake, the amount of specific uptake was calculated by subtracting the amount of nonspecific uptake from the total amount of uptake in the absence of 10 μM ALX5407. In addition, glycine uptake inhibiting activity ($IC_{50}$) was calculated from an inhibition curve for the concentration of the test substance ranging from $10^{-9}$ to $10^{-5}$ M.

It should be noted that ALX5407 is a HCl salt of N-[(3R)-3-([1,1'-biphenyl]-4-yloxy)-3-(4-fluorophenyl)propyl]-N-methylglycine.

The compounds of the present invention were found to have $IC_{50}$ values of 10 μM or less. Compounds 5, 24, 25, 29, 42, 52, 63, 111, 132, 137, 138, 141, 146 and 168 had $IC_{50}$ values of 1 μM or more, and the other compounds had $IC_{50}$ values smaller than 1 μM. For example, Compounds 5, 14, 30, 74, 107, 120, 121, 143, 153, 155, 160, 161, 191, 208 and 213 were found to have $IC_{50}$ values of 1.4 μM, 0.018 μM, 0.0073 μM, 0.015 μM, 0.0035 μM, 0.0080 μM, 0.16 μM, 0.064 μM, 0.030 μM, 0.0058 μM, 0.33 μM, 0.012 μM, 0.016 μM, 0.014 μM and 0.0037 μM, respectively.

Incidentally, Compound 56 which is recited as 2HCl salt in the above Table 1-6 was subjected to measurement as its free form in the Glycine Uptake Inhibition Experiment.

Test Example 2

Membrane Permeability Experiment

In the development of pharmaceuticals, membrane permeability is an important factor to consider from the viewpoint of relationship with the bodily absorption of a medicament to be administered orally. Compounds having high membrane permeability are expected to feature satisfactory absorption by the intestinal tract (see Pharmaceutical Research (2002) Vol. 19, No. 7, 921-925.)

A membrane permeability test was conducted using PAMPA Evolution™ (pION INC.) in accordance with a modified version of the recommended protocol of pION INC. To be more specific, solutions of an assay compound (i.e., a DMSO solution of the compound as diluted by being added to system solutions that had been adjusted to prescribed pHs (4.0, 5.0, 6.2, and 7.4)) were prepared and added to the lower compartment (donor) of a sandwich plate having a lipid bilayer membrane formed of an artificial lipid (GIT-0). An acceptor sink buffer was added to the upper compartment (acceptor) and after the lapse of a prescribed period, the cumulative permeation of the compound was measured by performing UV spectroscopy on the solutions in the donor and acceptor, and the membrane permeability coefficient Pe ($\times 10^{-6}$ cm/sec) was calculated to assay the membrane permeability of the compound. As it turned out, all the subject application compounds that were tested in the experiment, i.e. compound Nos. 1, 4, 9-11, 13-15, 21-23, 30, 31, 34, 36, 37, 39, 40, 50, 53-56, 61, 62, 64, 65, 67-70, 73, 74, 77-84, 88, 89, 92, 94, 95, 99-102, 104-110, 112-117, 119, 120, 122-124, 126, 127, 129, 133-135, 143-145, 147, 149, 150, 152, 154-158, 161-164, 166, 167, 169, 170, 176-181, 187-189, 191, 195, 197, 198, 204, 206-209, 211, 213, 214, 216, 221 and 223 were found to be "high" at pH 5 or more in accordance with the criteria described in the protocol by pION INC., thus indicating their satisfactory membrane permeability.

Test Example 3

Test for Recognizability of P-gp Substrate

In order that drugs acting on the central nervous system will develop their efficacy, their passage from the blood to the brain is generally important. While various efflux transporters are present at the blood-brain barrier to control this passage of drugs, P-glylcoprotein (P-gp) is a typical example and inhibits the passage to the brain of any drugs that serve as the substrate for P-gp. Therefore, in the development of pharmaceuticals, nonrecognizability of a candidate drug as the substrate for P-gp is the key to its passage to the brain.

A test for recognizability of P-gp substrate was performed in accordance with a modified version of the methods described in J Pharmacol. Exp. Ther. (1992) Vol. 263, No. 2, 840-845 and J Biol. Chem. (1992) Vol. 267, No. 34, 24248-24252. To be more specific, LLC-GAS-COL 300 cells (Human MDR1 expressing system derived from pig kidney derived, cultured renal epithelial cell line LLC-PK$_1$) were cultured for 4 days on a Transwell and replaced by a Hank's balanced salt solution (HBSS) in each well just before the test. A solution of an assay compound (a DMSO solution of the compound as diluted with HBSS and adjusted to a final concentration of 10 μM) was added to the donor side of the LLC-GAS-COL 300 cells and a prescribed amount of HBSS was collected from the acceptor side at given time intervals and the concentration of the assay compound in the collected sample was measured by LC-MS/MS.

From the cumulative amount of the compound's permeation into the acceptor, the membrane permeability coefficient ($\times 10^{-6}$ cm/sec) was calculated for each of apical→basal mode and basal→apical mode and the recognizability of P-gp substrate was assessed in terms of the ratio between the two modes (efflux ratio).

As it turned out, among the subject application compounds that were tested in the experiment, compound Nos. 9, 14, 15, 30, 31, 36, 54, 56, 62, 69, 73, 124, 158 and 198 were found to be not recognizable as the substrate for P-gp according to the criteria described in Nature Reviews Drug Discovery (2010), Vol. 9, 215-236, and that suggested the possibility of their satisfactory passage to the brain (see Pharmaceutical Research (2001), Vol. 18, No. 12, 1660-1668.) Incidentally, compounds 14, 15 and 158 which are recited as the free form in the above Table 1 were determined as HCl salt in the Test for Recognizability of P-gp Substrate. From this result, it is expected that the subject application compounds will be effectively used as drugs that act on the central nervous system.

INDUSTRIAL APPLICABILITY

The invention compounds have a glycine transporter (GlyT1) inhibiting action and, hence, is effective in the prevention or treatment of diseases associated with the glycine transporter, which specifically include schizophrenia, Alzheimer's disease, cognitive dysfunction, dementia, anxiety disorders (generalized anxiety disorder, panic disorder, obsessive-compulsive disorder, social anxiety disorder, posttraumatic stress disorder, specific phobia, acute stress disorder, etc.), depression, drug addiction, spasm, tremor, pain, sleep disorder and the like.

The invention claimed is:

1. A compound of the formula [I] or a pharmaceutically acceptable salt thereof:

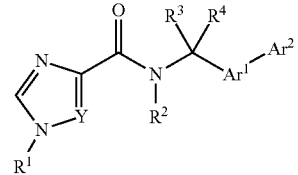

wherein
$R^1$ represents a hydrogen atom or a $C_{1-6}$ alkyl group,
$R^2$ represents a $C_{1-6}$ alkyl group optionally substituted by 1 to 3 substituents selected from among Group 1 of substituents, or represents a $C_{3-6}$ cycloalkyl group or a haloC$_{3-6}$ cycloalkyl group,
Group 1 of substituents is a group consisting of a $C_{1-6}$ alkoxyl group, a halogen atom, a $C_{3-6}$ cycloalkyl group, and a haloC$_{1-6}$ alkoxy group,
$R^3$ and $R^4$ are the same or different, and each represent a hydrogen atom or a $C_{1-6}$ alkyl group,
Y represents a nitrogen atom or the formula CH,
Ar$^1$ represents a phenylene group or a divalent monocyclic heteroaryl group, provided that the phenylene group or the divalent monocyclic heteroaryl group may be substituted by 1 to 3 substituents selected from Group 2 of substituents,
Group 2 of substituents is a group consisting of a $C_{1-6}$ alkoxyl group, a halogen atom, a $C_{1-6}$ alkyl group, a haloC$_{1-6}$ alkoxy group, and a haloC$_{1-6}$ alkyl group, Ar² represents a phenyl group, a naphthyl group, a monocyclic or bicyclic heteroaryl group, a pyridonyl group, or a group of the formula [III]

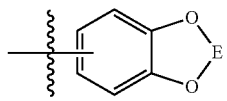

[III]

E represents a C₁₋₃ alkylene group, provided that the phenyl group, the naphthyl group, the monocyclic or bicyclic heteroaryl group, the pyridonyl group, or the group of the formula [III] may be substituted by 1 to 5 substituents selected from Group 3 of substituents, Group 3 of substituents is a group consisting of a $C_{1-6}$ alkyl group (which $C_{1-6}$ alkyl group may be substituted by 1 to 3 substituents selected from among a $C_{1-6}$ alkoxy group, a halogen atom, and a hydroxy group), a $C_{1-6}$ alkoxy group, a halogen atom, a halo$C_{1-6}$ alkoxy group, a $C_{1-6}$ alkylthio group, a halo$C_{1-6}$ alkylthio group, a cyano group, a carbamoyl group, the formula —SF₅, and the formula —NR⁹R¹⁰ (where R⁹ and R¹⁰ are the same or different, and each represent a hydrogen atom or a $C_{1-6}$ alkyl group or, taken together with the nitrogen atom to which they bind, represent a 4- to 6-membered cyclic structure), when Ar¹ is the phenylene group which may be substituted by 1 to 3 substituents selected from Group 2 of substituents, Ar² is the monocyclic or bicyclic heteroaryl group which may be substituted by 1 to 5 substituents selected from Group 3 of substituents, the pyridonyl group which may be substituted by 1 to 4 substituents selected from Group 3 of substituents, or the group of the formula [III] which may be substituted by 1 to 5 substituents selected from Group 3 of substituents (with the exception of 1-methyl-N-[3-(pyridin-2-yl)benzyl]-N-(tetrahydro-2H-pyran-4-yl)-1H-1,2,4-triazole-3-carboxamide, 1-methyl-N-[3-(pyridin-3-yl)benzyl]-N-(tetrahydro-2H-pyran-4-yl)-1H-1,2,4-triazole-3-carboxamide, 1-methyl-N-[3-(pyridin-4-yl)benzyl]-N-(tetrahydro-2H-pyran-4-yl)-1H-1,2,4-triazole-3-carboxamide, N-[3-(1H-imidazol-1-yl)benzyl]-1-methyl-N-(tetrahydro-2H-pyran-4-yl)-1H-1,2,4-triazole-3-carboxamide, and 1-methyl-N-[3-(1H-pyrazol-4-yl)benzyl]-N-(tetrahydro-2H-pyran-4-yl)-1H-1,2,4-triazole-3-carboxamide).

2. The compound or the pharmaceutically acceptable salt thereof according to claim 1, wherein R² is a $C_{1-6}$ alkyl group optionally substituted by 1 to 3 substituents selected from Group 1 of substituents, or represents a $C_{3-6}$ cycloalkyl group or a halo$C_{3-6}$ cycloalkyl group, Ar¹ is a phenylene group, a pyridine-diyl group, a pyrimidine-diyl group, an isoxazole-diyl group, an oxadiazole-diyl group, a thiazole-diyl group, or a pyrazole-diyl group, provided that the phenylene group, the pyridine-diyl group, the pyrimidine-diyl group, the isoxazole-diyl group, the oxadiazole-diyl group, the thiazole-diyl group, or the pyrazole-diyl group may be substituted by 1 to 3 halogen atoms, and Ar² is a phenyl group, a naphthyl group, a pyridyl group, a pyrimidyl group, a pyrazyl group, a pyrazolyl group, a thiazolyl group, an imidazolyl group, an isoxazolyl group, a thienyl group, a triazolyl group, an indolyl group, a benzofuryl group, a quinolyl group, an isoquinolyl group, a pyridonyl group, an imidazopyridyl group, or the group of the formula [III], provided that the phenyl group, the naphthyl group, the pyridyl group, the pyrimidyl group, the pyrazyl group, the pyrazolyl group, the thiazolyl group, the imidazolyl group, the isoxazolyl group, the thienyl group, the triazolyl group, the indolyl group, the benzofuryl group, the quinolyl group, the isoquinolyl group, the pyridonyl group, the imidazopyridyl group, or the group of the formula [III] may be substituted by 1 to 5 substituents selected from Group 3 of substituents.

3. The compound or the pharmaceutically acceptable salt thereof according to claim 1, wherein
R² is
a) a $C_{1-6}$ alkyl group optionally substituted by 1 to 3 substituents selected from among a $C_{1-6}$ alkoxyl group, a halogen atom, and a $C_{3-6}$ cycloalkyl group, or
b) a $C_{3-6}$ cycloalkyl group.

4. The compound or the pharmaceutically acceptable salt thereof according to claim 1, wherein
R² is a $C_{3-6}$ branched chain alkyl group, or a $C_{4-6}$ cycloalkyl group.

5. The compound or the pharmaceutically acceptable salt thereof according to claim 1, wherein Y is the formula CH.

6. The compound or the pharmaceutically acceptable salt thereof according to claim 1, wherein Ar¹ is a phenylene group optionally substituted by 1 to 3 substituents selected from Group 2 of substituents.

7. The compound or the pharmaceutically acceptable salt thereof according to claim 1, wherein Ar¹ is a 1,3-phenylene group which may be substituted by a halogen atom, a pyridine-2,4-diyl group (with the carbon atom adjacent to the nitrogen atom binding to Ar²), a pyrimidine-2,4-diyl group, an isoxazole-3,5-diyl group, an oxadiazole-3,5-diyl group, a thiazole-2,4-diyl group, or a pyrazole-1,4-diyl group.

8. The compound or the pharmaceutically acceptable salt thereof according to claim 1, wherein Ar¹ is a 1,3-phenylene group which has been substituted by a halogen atom, or a pyridine-2,4-diyl group (with the carbon atom adjacent to the nitrogen atom binding to Ar²).

9. The compound or the pharmaceutically acceptable salt thereof according to claim 1, wherein Ar² is a phenyl group, a naphthyl group, a pyridyl group, a pyrimidyl group, a pyrazyl group, a pyrazolyl group, an imidazolyl group, a thienyl group, an imidazo[1,2-a]pyridyl group, or a quinolyl group, provided that the phenyl group, the naphthyl group, the pyridyl group, the pyrimidyl group, the pyrazyl group, the pyrazolyl group, the imidazolyl group, the thienyl group, the imidazo[1,2-a]pyridyl group, or the quinolyl group may be substituted by 1 to 5 substituents selected from Group 3 of substituents.

10. The compound or the pharmaceutically acceptable salt thereof according to claim 1, wherein Ar² is a phenyl group which may be substituted by 1 to 5 substituents selected from Group 3 of substituents.

11. The compound or the pharmaceutically acceptable salt thereof according to claim 1, wherein Ar² is a phenyl group optionally substituted by 1 to 5 substituents selected from Group 4 of substituents, a pyridyl group optionally substituted by 1 to 4 substituents selected from Group 5 of substituents, a pyrimidyl group optionally substituted by 1 to 3 substituents selected from Group 5 of substituents, or a pyrazyl group optionally substituted by 1 to 3 substituents selected from Group 5 of substituents, Group 4 of substituents is a group consisting of a C$_{1-6}$ alkyl group optionally substituted by 1 to 3 halogen atoms, a halogen atom, and a haloC$_{1-6}$ alkoxy group, and Group 5 of substituents is a group consisting of a C$_{1-6}$ alkyl group optionally substituted by 1 to 3 halogen atoms, a C$_{1-6}$ alkoxy group, a halogen atom, a haloC$_{1-6}$ alkoxy group, a cyano group, and the formula —NR$^9$R$^{10}$.

12. The compound or the pharmaceutically acceptable salt thereof according to claim 1, wherein Ar$^2$ is a phenyl group optionally substituted by 1 to 5 substituents selected from the group 4 of substituents, or a pyridyl group optionally substituted by 1 to 4 substituents selected from Group 5 of substituents.

13. The compound or the pharmaceutically acceptable salt thereof according to claim 1, wherein Ar$^2$ is a phenyl group substituted by 1 to 5 haloC$_{1-6}$ alkoxy groups.

14. The compound or the pharmaceutically acceptable salt thereof according to claim 1, wherein R$^1$ is a C$_{1-6}$ alkyl group, and R$^3$ and R$^4$ are each a hydrogen atom.

15. The compound or the pharmaceutically acceptable salt thereof according to claim 1, which is selected from the following group of compounds:

N-[4-fluoro-3-(6-fluoropyridin-3-yl)benzyl]-1-methyl-N-(propan-2-yl)-1H-imidazole-4-carboxamide
N-[4-fluoro-3-(pyridin-2-yl)benzyl]-1-methyl-N-(propan-2-yl)-1H-imidazole-4-carboxamide
1-Methyl-N-(propan-2-yl)-N-({2-[4-trifluoromethoxy)phenyl]pyridin-4-yl}methyl)-1H-imidazole-4-carboxamide
N-{[2-(4-fluorophenyl)pyridin-4-yl]methyl}-1-methyl-N-(propan-2-yl)-1H-imidazole-4-carboxamide
1-Methyl-N-(propan-2-yl)-N-({2-[4-(trifluoromethyl)phenyl]pyridin-4-yl}methyl)-1H-imidazole-4-carboxamide
1-Methyl-N-[(2-phenylpyridin-4-yl)methyl]-N-(propan-2-yl)-1H-imidazole-4-carboxamide
N-{[2-(3-fluorophenyl)pyridin-4-yl]methyl}-1-methyl-N-(propan-2-yl)-1H-imidazole-4-carboxamide
N-cyclobutyl-N-{[2-(4-fluorophenyl)pyridin-4-yl]methyl}-1-methyl-1H-imidazole-4-carboxamide
N-{[2-(3,4-difluorophenyl)pyridin-4-yl]methyl}-1-methyl-N-(propan-2-yl)-1H-imidazole-4-carboxamide
N-{[2-(3,5-difluorophenyl)pyridin-4-yl]methyl}-1-methyl-N-(propan-2-yl)-1H-imidazole-4-carboxamide
1-Methyl-N-(propan-2-yl)-N-({2-[3-(trifluoromethoxy)phenyl]pyridin-4-yl}methyl)-1H-imidazole-4-carboxamide
N-{[2-(2,4-difluorophenyl)pyridin-4-yl]methyl}-1-methyl-N-(propan-2-yl)-1H-imidazole-4-carboxamide
1-Methyl-N-(propan-2-yl)-N-{[2-(3,4,5-trifluorophenyl)pyridin-4-yl]methyl}-1H-imidazole-4-carboxamide
1-Methyl-N-(propan-2-yl)-N-{[2-(2,3,4-trifluorophenyl)pyridin-4-yl]methyl}-1H-imidazole-4-carboxamide
N-{[2-(4-chlorophenyl)pyridin-4-yl]methyl}-1-methyl-N-(propan-2-yl)-1H-imidazole-4-carboxamide
N-[4-fluoro-3-(1H-pyrazol-1-yl)benzyl]-1-methyl-N-(propan-2-yl)-1H-imidazole-4-carboxamide
N-{[2-(2-fluorophenyl)pyridin-4-yl]methyl}-1-methyl-N-(propan-2-yl)-1H-imidazole-4-carboxamide
N-{[2-(3-chlorophenyl)pyridin-4-yl]methyl}-1-methyl-N-(propan-2-yl)-1H-imidazole-4-carboxamide
N-{[2-(2,3-difluorophenyl)pyridin-4-yl]methyl}-1-methyl-N-(propan-2-yl)-1H-imidazole-4-carboxamide
N-[4-fluoro-3-(3-fluoropyridin-2-yl)benzyl]-1-methyl-N-(propan-2-yl)-1H-imidazole-4-carboxamide
N-{[2-(3-chloro-4-fluorophenyl)pyridin-4-yl]methyl}-1-methyl-N-(propan-2-yl)-1H-imidazole-4-carboxamide
N-{[2-(3-fluoro-4-methylphenyl)pyridin-4-yl]methyl}-1-methyl-N-(propan-2-yl)-1H-imidazole-4-carboxamide
N-{[2-(4-fluoro-3-methylphenyl)pyridin-4-yl]methyl}-1-methyl-N-(propan-2-yl)-1H-imidazole-4-carboxamide
N-{[2-(3-chloro-5-fluorophenyl)pyridin-4-yl]methyl}-1-methyl-N-(propan-2-yl)-1H-imidazole-4-carboxamide
N-{[2-(2,5-difluorophenyl)pyridin-4-yl]methyl}-1-methyl-N-(propan-2-yl)-1H-imidazole-4-carboxamide
1-Methyl-N-(propan-2-yl)-N-{[2-(2,4,5-trifluorophenyl)pyridin-4-yl]methyl}-1H-imidazole-4-carboxamide
N-cyclobutyl-1-methyl-N-({2-[3-(trifluoromethoxy)phenyl]pyridin-4-yl}methyl)-1H-imidazole-4-carboxamide
N-cyclobutyl-1-methyl-N-({2-[4-(trifluoromethoxy)phenyl]pyridin-4-yl}methyl)-1H-imidazole-4-carboxamide
N-{[2-(3-fluoro-5-methylphenyl)pyridin-4-yl]methyl}-1-methyl-N-(propan-2-yl)-1H-imidazole-4-carboxamide
1-Methyl-N-(propan-2-yl)-N-({2-[3-trifluoromethyl)phenyl]pyridin-4-yl}methyl)-1H-imidazole-4-carboxamide
N-{[2-(3,4-dichlorophenyl)pyridin-4-yl]methyl}-1-methyl-N-(propan-2-yl)-1H-imidazole-4-carboxamide
N-{[2-(3,5-dichlorophenyl)pyridin-4-yl]methyl}-1-methyl-N-(propan-2-yl)-1H-imidazole-4-carboxamide
N-{[2-(2-chlorophenyl)pyridin-4-yl]methyl}-1-methyl-N-(propan-2-yl)-1H-imidazole-4-carboxamide
N-cyclobutyl-N-[4-fluoro-3-(6-fluoropyridin-3-yl)benzyl]-1-methyl-11H-imidazole-4-carboxamide
N-({2-[4-(difluoromethoxy)phenyl]pyridin-4-yl}methyl)-1-methyl-N-(propan-2-yl)-1H-imidazole-4-carboxamide
N-({2-[3-fluoro-4-(trifluoromethoxy)phenyl]pyridin-4-yl}methyl)-1-methyl-N-(propan-2-yl)-1H-imidazole-4-carboxamide
N-({2-[3-(difluoromethoxy)phenyl]pyridin-4-yl}methyl)-1-methyl-N-(propan-2-yl)-1H-imidazole-4-carboxamide
N-({2-[4-fluoro-3-(trifluoromethoxy)phenyl]pyridin-4-yl}methyl)-1-methyl-N-(propan-2-yl)-1H-imidazole-4-carboxamide
N-cyclobutyl-N-{[2-(3,4-difluorophenyl)pyridin-4-yl]methyl}-1-methyl-1H-imidazole-4-carboxamide
N-cyclobutyl-N-{[2-(3,5-difluorophenyl)pyridin-4-yl]methyl}-1-methyl-1H-imidazole-4-carboxamide
N-cyclobutyl-N-({2-[4-(difluoromethoxy)phenyl]pyridin-4-yl}methyl)-1-methyl-1H-imidazole-4-carboxamide
N-cyclobutyl-N-({2-[3-(difluoromethoxy)phenyl]pyridin-4-yl}methyl)-1-methyl-1H-imidazole-4-carboxamide
N-cyclobutyl-1-methyl-N-({2-[4-(trifluoromethoxy)phenyl]pyridin-4-yl}methyl)-1H-1,2,4-triazole-3-carboxamide
N-cyclobutyl-1-methyl-N-({2-[3-(trifluoromethoxy)phenyl]pyridin-4-yl}methyl)-1H-1,2,4-triazole-3-carboxamide
N-cyclobutyl-1-methyl-N-{[2-(2,4,5-trifluorophenyl)pyridin-4-yl]methyl}-1H-imidazole-4-carboxamide
N-cyclobutyl-N-{[2-(2,3-difluorophenyl)pyridin-4-yl]methyl}-1-methyl-1H-imidazole-4-carboxamide
N-cyclobutyl-N-{[2-(2,4-difluorophenyl)pyridin-4-yl]methyl}-1-methyl-1H-imidazole-4-carboxamide
N-cyclobutyl-N-{[2-(2,5-difluorophenyl)pyridin-4-yl]methyl}-1-methyl-1H-imidazole-4-carboxamide N-cyclobutyl-N-[4-fluoro-3-(3-fluoropyridin-2-yl)benzyl]-1-methyl-11H-imidazole-4-carboxamide N-cyclobutyl-N-({2-[3-(difluoromethoxy)-4-fluorophenyl]pyridin-4-yl}methyl)-1-methyl-1H-imidazole-4-carboxamide N-cyclobutyl-N-({2-[4-(difluoromethoxy)-3-fluorophenyl]pyridin-4-yl}methyl)-1-methyl-1H-imidazole-4-carboxamide.

16. A pharmaceutical composition comprising, as an active ingredient, the compound or the pharmaceutically acceptable salt thereof according to claim 1 and a pharmaceutically acceptable carrier.

17. A method for inhibiting glycine uptake by cells, which comprises administering to a subject an effective amount of the compound or the pharmaceutically acceptable salt thereof according to claim 1.

* * * * *